US007875272B2

(12) United States Patent
Messina et al.

(10) Patent No.: US 7,875,272 B2
(45) Date of Patent: Jan. 25, 2011

(54) TREATMENT OF STROKE AND OTHER ACUTE NEURALDEGENERATIVE DISORDERS USING POSTPARTUM DERIVED CELLS

(75) Inventors: Darin J. Messina, Downingtown, PA (US); Sanjay Mistry, Downingtown, PA (US); L. S. Klaudyne Hong, Jersey City, NJ (US); Brian C. Kramer, Plainfield, NJ (US); Michael J. Romanko, New Hope, PA (US); Anna Gosiewska, Skillman, NJ (US)

(73) Assignee: Ethicon, Incorporated, Somerville, NJ (US)

( * ) Notice: Subject to any disclaimer, the term of this patent is extended or adjusted under 35 U.S.C. 154(b) by 324 days.

(21) Appl. No.: 11/315,898

(22) Filed: Dec. 22, 2005

(65) Prior Publication Data

US 2006/0233765 A1    Oct. 19, 2006

Related U.S. Application Data

(63) Continuation-in-part of application No. 10/877,269, filed on Jun. 25, 2004.

(60) Provisional application No. 60/483,264, filed on Jun. 27, 2003, provisional application No. 60/638,966, filed on Dec. 23, 2004.

(51) Int. Cl.
*C12N 5/00* (2006.01)
*C12N 5/071* (2006.01)

(52) U.S. Cl. .................. 424/93.1; 435/325; 435/366; 435/368

(58) Field of Classification Search .............. None
See application file for complete search history.

(56) References Cited

U.S. PATENT DOCUMENTS

| | | | |
|---|---|---|---|
| 4,352,883 A | 10/1982 | Lim | 435/178 |
| 4,882,162 A | 11/1989 | Ikada et al. | 424/444 |
| 4,963,489 A | 10/1990 | Naughton et al. | 435/240.1 |
| 5,004,681 A | 4/1991 | Boyse et al. | 435/2 |
| 5,192,553 A | 3/1993 | Boyse et al. | 424/529 |
| 5,286,632 A | 2/1994 | Jones | 435/91.2 |
| 5,320,962 A | 6/1994 | Stiles et al. | 435/252.3 |
| 5,342,761 A | 8/1994 | MacLeod | 435/69.1 |
| 5,437,994 A | 8/1995 | Emerson et al. | 435/373 |
| 5,443,950 A | 8/1995 | Naughton et al. | 435/1.1 |
| 5,466,233 A | 11/1995 | Weiner et al. | 604/890.1 |
| 5,486,359 A | 1/1996 | Caplan et al. | 424/93.7 |

(Continued)

FOREIGN PATENT DOCUMENTS

EP    0 333 328 B1    12/1993

(Continued)

OTHER PUBLICATIONS

Schouten et al., Journal of Neurotrauma. Nov. 1, 2004, 21(11): 1501-1538.*

(Continued)

*Primary Examiner*—David S Romeo
*Assistant Examiner*—Daniel C Gamett
(74) *Attorney, Agent, or Firm*—Patton Boggs LLP

(57) ABSTRACT

Cells derived from postpartum tissue such as the umbilical cord and placenta, and methods for their use to regenerate, repair, and improve neural tissue, and to improve behavior and neurological function in stroke patients are disclosed.

20 Claims, 4 Drawing Sheets

U.S. PATENT DOCUMENTS

| | | | |
|---|---|---|---|
| 5,580,777 A | 12/1996 | Bernard et al. | |
| 5,589,376 A | 12/1996 | Anderson et al. | 435/240.2 |
| 5,670,483 A | 9/1997 | Zhang et al. | 514/14 |
| 5,677,181 A | 10/1997 | Parish | 435/332 |
| 5,684,032 A * | 11/1997 | Elliott et al. | 514/414 |
| 5,693,332 A | 12/1997 | Hansbrough | |
| 5,698,518 A | 12/1997 | Carson et al. | 514/12 |
| 5,707,643 A | 1/1998 | Ogura et al. | 424/428 |
| 5,718,922 A | 2/1998 | Herrero-Vanrell et al. | |
| 5,736,516 A | 4/1998 | Louis | 514/12 |
| 5,811,094 A | 9/1998 | Caplan et al. | 424/93.7 |
| 5,827,735 A | 10/1998 | Young et al. | 435/325 |
| 5,834,308 A | 11/1998 | Peck et al. | 435/325 |
| 5,840,580 A | 11/1998 | Terstappen et al. | 435/372 |
| 5,843,780 A | 12/1998 | Thomson | 435/363 |
| 5,843,781 A | 12/1998 | Ballermann et al. | |
| 5,869,079 A | 2/1999 | Wong et al. | 424/426 |
| 5,902,598 A | 5/1999 | Chen et al. | 424/423 |
| 5,902,741 A | 5/1999 | Purchio et al. | |
| 5,906,934 A | 5/1999 | Grande et al. | 435/325 |
| 5,919,702 A | 7/1999 | Purchio et al. | 435/378 |
| 5,942,225 A | 8/1999 | Bruder et al. | 424/93.7 |
| 5,955,343 A | 9/1999 | Holmes et al. | 435/240.1 |
| 5,962,325 A | 10/1999 | Naughton et al. | 435/395 |
| 5,994,094 A | 11/1999 | Hötten et al. | 435/69.1 |
| 6,001,647 A | 12/1999 | Peck et al. | 435/325 |
| 6,022,743 A | 2/2000 | Naughton et al. | 435/395 |
| 6,140,039 A | 10/2000 | Naughton et al. | 435/1.1 |
| 6,171,610 B1 | 1/2001 | Vacanti et al. | 424/426 |
| 6,179,872 B1 | 1/2001 | Bell et al. | |
| 6,200,606 B1 | 3/2001 | Peterson | 424/574 |
| 6,200,806 B1 | 3/2001 | Thomson | 435/366 |
| 6,214,369 B1 | 4/2001 | Grande et al. | 424/423 |
| 6,251,090 B1 | 6/2001 | Avery et al. | 604/9 |
| 6,291,240 B1 | 9/2001 | Mansbridge et al. | |
| 6,323,188 B1 | 11/2001 | Weissman | 514/52 |
| 6,326,201 B1 | 12/2001 | Fung et al. | 435/377 |
| 6,331,313 B1 | 12/2001 | Wong et al. | 424/427 |
| 6,333,029 B1 | 12/2001 | Vyakarnam et al. | |
| 6,355,239 B1 | 3/2002 | Bruder et al. | 424/93.1 |
| 6,355,699 B1 | 3/2002 | Vyakarnam et al. | 521/61 |
| 6,358,737 B1 | 3/2002 | Bonewald et al. | |
| 6,372,494 B1 | 4/2002 | Naughton et al. | |
| 6,375,972 B1 | 4/2002 | Guo et al. | 424/423 |
| 6,387,367 B1 | 5/2002 | Davis-Sproul et al. | 424/93.1 |
| 6,391,297 B1 | 5/2002 | Halvorsen | 424/93.7 |
| 6,429,013 B1 | 8/2002 | Halvorsen et al. | 435/377 |
| 6,436,704 B1 | 8/2002 | Roberts et al. | 435/366 |
| 6,497,875 B1 | 12/2002 | Sorrell et al. | 424/93.7 |
| 6,528,245 B2 | 3/2003 | Sanchez-Ramos et al. | 435/1.1 |
| 6,534,084 B1 | 3/2003 | Vyakarnam et al. | |
| 6,555,374 B1 | 4/2003 | Gimble et al. | 435/371 |
| 6,599,323 B2 | 7/2003 | Melican et al. | 623/23.72 |
| 6,610,535 B1 | 8/2003 | Lu et al. | 435/325 |
| 6,638,765 B1 | 10/2003 | Rosenberg | 435/377 |
| 6,673,606 B1 | 1/2004 | Tennekoon et al. | 435/372 |
| 6,680,198 B1 | 1/2004 | Snyder et al. | 435/368 |
| 6,686,198 B1 | 2/2004 | Melton et al. | 435/377 |
| 6,699,837 B2 * | 3/2004 | Nakamura | 514/12 |
| 6,703,017 B1 | 3/2004 | Peck et al. | 424/93.7 |
| 6,916,655 B2 | 7/2005 | Yasumoto et al. | 435/371 |
| 2001/0024824 A1 | 9/2001 | Moss et al. | 435/366 |
| 2001/0031256 A1 | 10/2001 | Edge | 424/93.7 |
| 2001/0046489 A1 | 11/2001 | Habener et al. | 424/93.21 |
| 2002/0022676 A1 | 2/2002 | He et al. | 523/113 |
| 2002/0028510 A1 | 3/2002 | Sanberg et al. | 435/368 |
| 2002/0062151 A1 | 5/2002 | Altman et al. | 623/13.7 |
| 2002/0081725 A1 | 6/2002 | Tsang et al. | 435/366 |
| 2002/0098584 A1 | 7/2002 | Palmer et al. | 435/366 |
| 2002/0119565 A1 | 8/2002 | Clarke et al. | 435/366 |
| 2002/0123141 A1 | 9/2002 | Hariri | 435/366 |
| 2002/0150986 A1 | 10/2002 | Lau | 435/69.1 |
| 2002/0151056 A1 | 10/2002 | Sasai et al. | 435/368 |
| 2002/0160471 A1 | 10/2002 | Kisiday et al. | 435/177 |
| 2002/0160510 A1 * | 10/2002 | Hariri | 435/368 |
| 2002/0164307 A1 | 11/2002 | Habener et al. | 424/93.7 |
| 2002/0164791 A1 | 11/2002 | Van Der Kooy et al. | 435/366 |
| 2002/0168763 A1 | 11/2002 | Yan et al. | 435/325 |
| 2002/0182728 A1 | 12/2002 | Ramiya et al. | 435/366 |
| 2002/0187550 A1 | 12/2002 | Dinsmore et al. | 435/377 |
| 2002/0192816 A1 | 12/2002 | Roberts et al. | 435/366 |
| 2003/0003574 A1 | 1/2003 | Toma et al. | 435/368 |
| 2003/0007954 A1 | 1/2003 | Naughton et al. | |
| 2003/0008820 A1 * | 1/2003 | Kwan et al. | 514/12 |
| 2003/0022369 A1 | 1/2003 | Fillmore et al. | 435/371 |
| 2003/0031657 A1 | 2/2003 | Habener et al. | 424/93.21 |
| 2003/0032179 A1 | 2/2003 | Hariri | 435/366 |
| 2003/0032183 A1 | 2/2003 | Sheridan | 435/370 |
| 2003/0049837 A1 | 3/2003 | Weiss et al. | 435/368 |
| 2003/0059939 A1 | 3/2003 | Page et al. | 435/366 |
| 2003/0082155 A1 | 5/2003 | Habener et al. | 424/93.21 |
| 2003/0082160 A1 | 5/2003 | Yu et al. | 424/93.21 |
| 2003/0096409 A1 | 5/2003 | Yasumoto et al. | 435/371 |
| 2003/0104997 A1 | 6/2003 | Black et al. | 514/12 |
| 2003/0109036 A1 | 6/2003 | Wu | 435/366 |
| 2003/0113910 A1 | 6/2003 | Levanduski | 435/325 |
| 2003/0118566 A1 | 6/2003 | Neuman et al. | 424/93.21 |
| 2003/0124721 A1 | 7/2003 | Cheatham et al. | 435/366 |
| 2003/0138948 A1 | 7/2003 | Fisk et al. | 435/366 |
| 2003/0138951 A1 | 7/2003 | Yin | 435/370 |
| 2003/0148513 A1 | 8/2003 | Sugaya et al. | 435/368 |
| 2003/0161818 A1 * | 8/2003 | Weiss et al. | 424/93.21 |
| 2003/0162290 A1 | 8/2003 | Inoue et al. | 435/366 |
| 2003/0170215 A1 | 9/2003 | Tsang et al. | 424/93.21 |
| 2003/0175963 A1 | 9/2003 | Rosenberg | 435/375 |
| 2003/0180269 A1 | 9/2003 | Hariri | 424/93.21 |
| 2003/0186439 A1 | 10/2003 | Nakauchi et al. | 435/370 |
| 2003/0199447 A1 | 10/2003 | Goldman et al. | 514/12 |
| 2003/0203483 A1 | 10/2003 | Seshi | 435/366 |
| 2003/0203484 A1 | 10/2003 | Black et al. | 435/368 |
| 2003/0207450 A1 | 11/2003 | Young et al. | 435/368 |
| 2003/0211087 A1 | 11/2003 | Goldman | 424/93.21 |
| 2003/0211603 A1 | 11/2003 | Earp et al. | 435/366 |
| 2003/0211605 A1 | 11/2003 | Lee et al. | 435/368 |
| 2003/0212024 A1 | 11/2003 | Keating et al. | 514/44 |
| 2003/0219894 A1 | 11/2003 | Seino et al. | 435/370 |
| 2003/0228295 A1 | 12/2003 | Svendsen | 424/93.21 |
| 2003/0235563 A1 | 12/2003 | Strom et al. | 424/93.21 |
| 2003/0235909 A1 | 12/2003 | Hariri et al. | 435/372 |
| 2004/0005704 A1 | 1/2004 | Csete et al. | 435/368 |
| 2004/0009593 A1 | 1/2004 | Keirstead et al. | 435/368 |
| 2004/0014206 A1 | 1/2004 | Robl et al. | 435/325 |
| 2004/0014210 A1 | 1/2004 | Jessell et al. | 435/368 |
| 2004/0014211 A1 | 1/2004 | Ogle et al. | 435/368 |
| 2004/0014662 A1 | 1/2004 | Lindquist et al. | 514/12 |
| 2004/0028660 A1 * | 2/2004 | Hariri et al. | 424/93.7 |
| 2004/0029269 A1 | 2/2004 | Goldman et al. | 435/368 |
| 2004/0033597 A1 | 2/2004 | Toma et al. | 435/368 |
| 2004/0037818 A1 | 2/2004 | Brand et al. | 424/93.21 |
| 2004/0048372 A1 | 3/2004 | Hariri | 435/366 |
| 2004/0058412 A1 | 3/2004 | Ho et al. | 435/69.1 |
| 2004/0063202 A1 | 4/2004 | Petersen et al. | 435/368 |
| 2004/0072344 A1 | 4/2004 | Inoue et al. | 435/366 |
| 2004/0136967 A1 | 7/2004 | Weiss et al. | 424/93.7 |
| 2005/0019865 A1 | 1/2005 | Kihm et al. | 435/69.1 |
| 2005/0032209 A1 | 2/2005 | Messina et al. | 435/366 |
| 2005/0037491 A1 | 2/2005 | Mistry et al. | 435/366 |
| 2005/0054098 A1 | 3/2005 | Mistry et al. | 435/372 |
| 2005/0058629 A1 | 3/2005 | Harmon et al. | 424/93.7 |
| 2005/0058630 A1 | 3/2005 | Harris et al. | 424/93.7 |
| 2005/0058631 A1 | 3/2005 | Kihm et al. | 424/93.7 |
| 2005/0074435 A1 | 4/2005 | Casper et al. | 424/93.7 |
| 2005/0148074 A1 | 7/2005 | Davies et al. | 435/372 |
| 2005/0249731 A1 | 11/2005 | Aslan et al. | 424/144.1 |

| | | | |
|---|---|---|---|
| 2006/0153815 A1 | 7/2006 | Seyda et al. | |
| 2006/0153816 A1 | 7/2006 | Brown et al. | 424/93.7 |
| 2006/0153817 A1 | 7/2006 | Kihm et al. | 424/93.7 |
| 2006/0153818 A1 | 7/2006 | Dhanaraj et al. | 424/93.7 |
| 2006/0154366 A1 | 7/2006 | Brown et al. | 435/366 |
| 2006/0154367 A1 | 7/2006 | Kihm et al. | 435/366 |
| 2006/0166361 A1 | 7/2006 | Seyda et al. | |
| 2006/0171930 A1 | 8/2006 | Seyda et al. | |
| 2006/0188983 A1 | 8/2006 | Harris et al. | 435/366 |
| 2006/0223177 A1 | 10/2006 | Harris et al. | 435/325 |
| 2006/0233766 A1 | 10/2006 | Messina et al. | 424/93.7 |
| 2006/0234376 A1 | 10/2006 | Mistry et al. | 435/366 |
| 2007/0009494 A1 | 1/2007 | Mistry et al. | 424/93.7 |
| 2007/0014771 A1 | 1/2007 | Mistry et al. | 424/93.7 |
| 2007/0036767 A1 | 2/2007 | Mistry et al. | 424/93.7 |
| 2007/0141700 A1 | 6/2007 | Harmon | |
| 2007/0160588 A1 | 7/2007 | Kihm | 424/93.21 |
| 2007/0264269 A1 | 11/2007 | Harmon et al. | |
| 2007/0264713 A1 | 11/2007 | Terstegge et al. | |
| 2007/0275362 A1 | 11/2007 | Edinger et al. | 435/1.2 |
| 2008/0112939 A1 | 5/2008 | Colter et al. | |
| 2008/0145934 A1 | 6/2008 | Harris et al. | |
| 2008/0166328 A1 | 7/2008 | Harmon et al. | |

FOREIGN PATENT DOCUMENTS

| | | |
|---|---|---|
| EP | 1 216 718 | 6/2002 |
| EP | 1 264 877 | 12/2002 |
| EP | 1 302 535 | 4/2003 |
| EP | 1 312 669 | 5/2003 |
| EP | 1 316 322 | 6/2003 |
| EP | 1 405 649 | 4/2004 |
| JP | 2003-235549 | 8/2003 |
| WO | 90/11354 A1 | 10/1990 |
| WO | 92/03917 A1 | 3/1992 |
| WO | 93/04169 A1 | 3/1993 |
| WO | 94/25584 A1 | 11/1994 |
| WO | 95/17911 A1 | 7/1995 |
| WO | 96/01316 A1 | 1/1996 |
| WO | 96/05309 A2 | 2/1996 |
| WO | 98/17791 A1 | 4/1998 |
| WO | 98/51317 | 11/1998 |
| WO | WO 99/03973 | 1/1999 |
| WO | WO 99/28444 | 6/1999 |
| WO | 00/09666 | 2/2000 |
| WO | WO 00/38762 | 7/2000 |
| WO | WO 00/46351 | 8/2000 |
| WO | 00/73421 A3 | 12/2000 |
| WO | 01/11011 A2 | 2/2001 |
| WO | 01/19379 A3 | 3/2001 |
| WO | 01/34775 A1 | 5/2001 |
| WO | 02/29971 A1 | 4/2002 |
| WO | WO 02/36751 | 5/2002 |
| WO | 02/46373 A1 | 6/2002 |
| WO | 02/059278 A2 | 8/2002 |
| WO | 02/062969 A2 | 8/2002 |
| WO | 02/063962 A1 | 8/2002 |
| WO | 02/064748 A2 | 8/2002 |
| WO | 02/064755 A2 | 8/2002 |
| WO | WO 02/061053 | 8/2002 |
| WO | 02/086107 A2 | 10/2002 |
| WO | 03/023020 A1 | 3/2003 |
| WO | 03/025149 A2 | 3/2003 |
| WO | 03/029443 A1 | 4/2003 |
| WO | 03/029445 A1 | 4/2003 |
| WO | 03/039489 A3 | 5/2003 |
| WO | 03/042405 A2 | 5/2003 |
| WO | 03/048336 A2 | 6/2003 |
| WO | 03/055992 A2 | 7/2003 |
| WO | 03/064601 A2 | 8/2003 |
| WO | 03/066832 A2 | 8/2003 |
| WO | 03/068937 A2 | 8/2003 |
| WO | 03/070922 A1 | 8/2003 |
| WO | 03/072728 A2 | 9/2003 |
| WO | 03/080822 A1 | 10/2003 |
| WO | 03/087333 A2 | 10/2003 |
| WO | 03/087392 A2 | 10/2003 |
| WO | 03/089619 A2 | 10/2003 |
| WO | 03/010038 A1 | 12/2003 |
| WO | 03/102134 A2 | 12/2003 |
| WO | 03/104442 A1 | 12/2003 |
| WO | WO 03/102151 A2 | 12/2003 |
| WO | 2004/011012 A2 | 2/2004 |
| WO | 2004/011621 A2 | 2/2004 |
| WO | 2004/016747 A2 | 2/2004 |
| WO | 2004/023100 A2 | 3/2004 |
| WO | 2004/072273 A1 | 8/2004 |
| WO | 2005/001076 A2 | 1/2005 |
| WO | 2005/001077 A2 | 1/2005 |
| WO | 2005/001078 A2 | 1/2005 |
| WO | 2005/001079 A2 | 1/2005 |
| WO | 2005/001080 A2 | 1/2005 |
| WO | 2005/003334 A2 | 1/2005 |
| WO | WO 2005/021738 | 3/2005 |
| WO | 2005/038012 A2 | 4/2005 |
| WO | 2005/042703 A2 | 5/2005 |
| WO | WO 2006/027229 | 3/2006 |
| WO | WO 2006/036826 | 4/2006 |
| WO | 2006/071773 A2 | 7/2006 |
| WO | 2006/071777 A2 | 7/2006 |
| WO | 2006/071778 A2 | 7/2006 |
| WO | 2006/071794 A2 | 7/2006 |
| WO | 2006/071802 A2 | 7/2006 |
| WO | WO 2006/105152 | 10/2006 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |

OTHER PUBLICATIONS

"Cell Lysis, p. 2" http://www.piercenet.com/Objects/view.cfm?type= Page&Id=1904ED25-8FA4-475C-8068-C2EB13D5F4E7; accessed Aug. 7, 2008.*
Yamashima, (2000) Progress in Neurobiology 62:273-295.*
Weiss et al., Stem Cells. Mar. 2006; 24(3):781-792.*
Medicetty et al. 2003, BIOSIS accession No. PREV200400197685.*
Aboody, K.S., et al., "Neural stem cells display extensive tropism for pathology in adult brain: evidence from intracranial gliomase," *PNAS*, 2000, 97(23), 12846-12851.
Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, *Arch. Ophthalmal*, 2001, 119, 1417-1436.
Allcock, H.R., et al., "Synthesis of poly[amino acid alkyl ester)phosphazenes]$^{1-3}$," *Macromolecule*, 1977, 10(4), 824-830.
Altman, G.H., et al., "Advanced bioreactor with controlled application of multi-dimensional strain for tissue engineering," *J. Biomech. Eng.*, 2002, 124, 742-749.
Altman, R.D., et al., "Radiographic assessment of progression in osteoarthritis," *Arthritis & Rheum.*, 1987, 30(11), 1214-1225.
Anseth, K.S., et al., "In situ forming degradable netrks and their application in tissue engineering and drug delivery," *J. of Control Release*, 2002, 78, 199-209.
Avital, I., et al., "Isolation, characterization, and transplantation of bone marrow-derived hepatocyte stem cells," *Biochem. & Biophys. Res. Comm.*, 2001, 288, 156-164.
Azizi, S.A., et al., "Engraftment and migration of human bone marrow stromal cells implanted in the brains of albino rats—similarities to astrocyte grafts," *Proc. Natl. Acad. Sci. USA*, 1998, 95, 3908-3913.
Baker, K.A., et al., "Intrastriatal and intranigral grafting of hNT neurons in the 6-OHDA rat model of Parkinson's Disease," *Exper. Neurol.*, 2000, 162, 350-360.

Balis, F., et al., "Central nervous system pharmacology of antileukemic drugs," *Am. J. of Pediatric. Hematol. Oncol.*, 1989, 11(1), 74-86.

Balkema, G.W., et al., "Impaired visual thresholds in hypopigmented animals," *Visual Neuroscience*, 1991, 6, 577-585.

Barberi, T., et al., "Neural subtype specification of fertilization and nuclear transfer embryonic stem cells and application in parkinsonian mice," *Nature Biotechnology*, 2003, 21(10), 1200-1207.

Beck, R.W., et al., "A clinical comparison of visual field testing with a new automated perimeter, the Humphrey field analyzer, and the Goldmann perimeter," *Ophthalmology*, 1985, 92(1), 77-82.

Björklund, L.M., et al., "Embryonic stem cells develop into functional dopaminergic neurons after transplantation in a Parkinson rat model," *PNAS*, 2002, 99(4), 2344-2349.

Brodsky, S.V., et al., "Coagulation, fibrinolysis and angiogenesis: new insights from knockout mice," *Exp. Nephrol.*, 2002, 10, 299-306.

Brooks, P., "Inflammation as an important feature of osteoarthritis," *Bull. rld Health Org.*, 2003, 81(9), 689-690.

Brown, J.A., et al., "Blockade of programmed death-1 ligands on dendritic cells enhances T cell activation and cytokine production," *The J. of Immunology*, 2003, 170, 1257-1266.

Burnstein, R.M., et al., "Differentiation and migration of long term expanded human neural progenitors in a partial lesion model of Parkinson's disease," *Intern. J. of Biochem. & Cell Biology*, 2004, 36, 702-713.

Caballero, S., et al., "The many possible roles of stem cells in age-related macular degeneration," *Graefe's Arch Clin. Exp. Ophthalmol*, 2004, 242, 85-90.

Campbell, I.K., et al., "Human articular cartilage and chondrocytes produce hemopoietic colony-stimulating factors in culture in response to IL-1$^1$," *J. of Immun.*, 1991, 147, 1238-1246.

Cao, Q., et al., "Stem cell repair of central nervous system injury," *J. of Neuroscience Res.*, 2002, 68, 501-510.

Caplan, A.I., et al., "Mesenchymal stem cells: building blocks for molecular medicine in the 21$^{st}$ century," *Trends in Molecular Med.*, 2001, 7(6), 259-264.

Chagracui, J., et al., "Fetal liver stroma consists of cells in epithelial-to-mesenchymal transition," *Blood*, 2003, 101, 2973-2982.

Chen, D., et al., "Differential roles for bone morphogenic protein (BMP) receptor type IB and IA in differentiation and specification of mesenchymal precursor cells to osteoblast and adipocyte lineages," *J. Cell Biol.*, 1998, 142(1), 295-305.

Cheng, A., et al., "Nitric oxide acts in a positive feedback loop with BDNF to regulate neural progenitor cell proliferation and differentiation in the mammalian brain," *Dev. Biol.*, 2003, 258, 319-333.

Coumans, B., et al., "Lymphoid cell apoptosis induced by trophoblastic cells: a model of active foeto-placental tolerance," *J. of Immunological Methods*, 1999, 224, 185-196.

D'Cruz, P.M., et al., "Mutation of the receptor tyrosine kinase gene Mertk in the retinal dystrophic RCS rat," *Hum. Mol. Genet.*, 2000, 9(4), 645-651.

Danon, D., et al., "Macrophage treatment of pressure sores in paraplegia," *J. of und Care*, 1998, 7(6), 281-283.

Danon, D., et al., "Treatment of human ulcers by application of macrophages prepared from a blood unit," *Exp. Gerontol.*, 1997, 32(6), 633-641.

Dimri, G.P., et al., "A biomarker that identifies senescent human cells in culture and in aging skin in vivo," *Proc. Natl. Acad. Sci. USA*, 1995, 92, 9363-9367.

Domb, A., et al., "Degradable polymers for site-specific drug delivery," *Polymers for Advanced Technologies*, 1992, 3, 279-292.

Doshi, S.N., et al., "Evolving role of tissue factor and its pathway inhibitor," *Critical Care Med.*, 2002, 30(5), S241-S250.

Du, Y., et al., "Functional reconstruction of rabbit corneal epithelium by human limbal cells cultured on amniotic membrane," *Molecular Vision*, 2003, 9, 635-643.

Eblenkamp, M. et al., "Umbilical cord stromal cells (UCSC). Cells featuring osteogenic differentiation potential," *Der Orthopade*, Dec. 2004, 33(12), 1338-1345.

Edlund, H., "Pancreatic organogenesis—developmental mechanisms and implications for therapy," *Nat. Rev. Genet.*, 2002, 3, 524-532.

Efrat, S., et al., "Cell replacement therapy for type 1 diabetes," *TRENDS in Molecular Medicine*, 2002, 8(7), 334-339.

Ehtesham, M., et al., "Induction of glioblastoma apoptosis using neural stem cell-mediated delivery of tumor necrosis factor-related apoptosis-inducing ligand," *Cancer Res.*, 2002, 62, 7170-7174.

Ehtesham, M., et al., "The use of interleukin 12-secreting neural stem cells for the treatment of intracranial glioma," *Cancer Res.*, 2002, 5657-5663.

Ende, N., et al., "Parkinson's disease mice and human umbilical cord blood," *J. Med.*, 2002, 33(1-4), 173-180, 1 page (Abstract).

Engstad, C.S., et al., "The effect of soluble β-1,3-glucan and lipopolysaccharide on cytokine production and coagulation activation in whole blood," *Int. Immunopharmacol.*, 2002, 2, 1585-1597.

Enzmann, V., et al., "Enhanced induction of RPE lineage markers in pluripotent neural stem cells engrafted into the adult rat subretinal space," *Investig. Ophthalmol. Visual Sci.*, 2003, 44, 5417-5422.

Fazeabas, A.T., et al., "Endometrial function: cell specific changes in the uterine environment," *Mol. & Cellular. Endo.*, 2002, 186, 143-147.

Fiegel, H.C., et al., "Liver-specific gene expression in cultured human hematopoietic stem cells," *Stem Cells*, 2003, 21, 98-104.

Fischer, D., et al., "Lens-injury-stimulated axonal regeneration throughout the optic pathway of adult rats," *Exp. Neurol.*, 2001, 172, 257-272.

Freed, C.R., et al., "Transplantation of embryonic dopamine neurons for severe Parkinson's disease," *N. Engl. J. Med.*, 2001, 344(10), 710-719.

Frenkel, O., et al., "Activated macrophages for treating skin ulceration: gene expression in human monocytes after hypo-osmotic shock," *Clin. Exp. Immunol.*, 2002, 128, 59-66.

Friedman, J.A., et al., "Biodegradable polymer grafts for surgical repair of the injured spinal cord," *Neurosurgery*, 2002, 51(3), 742-751.

Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.

Fukuda, K., et al., "Reprogramming of bone marrow mesenchymal stem cells into cardiomyocytes," *C.R. Biol.*, 2002, 325, 1027-1038.

Gerdes, D., et al., "Cloning and tissue expression of t putative steroid membrane receptors," *Biol. Chem.*, 1998, 379, 907-911.

Gellersen, B., et al., "Cyclic AMP and progesterone receptor cross-talk in human endometrium: a decidualizing affair," *J. of Endocrinol.*, 2003, 178, 357-372.

Gökhan, S. et al., "Basic and clinical neuroscience applications of embryonic stem cells," *Anat. Rec. (New Anat)*, 2001, 265, 142-156.

Gosiewska, A., et al., "Development of a three-dimensional transmigration assay for testing cell-polymer interactions for tissue engineering applications," *Tissue Eng.*, 2001, 7(3), 267-277.

Gottleib, D.I., "Large-scale sources of neural stem cells," *Ann. Rev. Neurosci.*, 2002, 25, 381-407.

Halvorsen, Y.D., et al., "Extracellular matrix mineralization and osteoblast gene expression by human adipose tissue-derived stromal cells," *Tissue Eng.*, 2001, 7, 729-741.

Hanahan, D., "Heritable formation of pancreatic β-cell tumours in transgenic mice expressing recombinant insulin/simian virus 40 oncogenes," *Nature*, 1985, 315, 115-122.

Haruta, M., et al., "In vitro and in vivo characterization of pigment epithelial cells differentiated from primate embryonic stem cells," *Investig. Ophthalmol. & Visual Sci.*, 2004, 45(3), 1020-1025.

Hayflick, L., "The longevity of cultured human cells," *J. Am. Geriatr. Soc.*, 1974, 22(1), 1-12.

Hayflick, L., "The strategy of senescence," *Gerontologist*, 1974, 14(1), 37-45.

Hongpaisan, J., "Inhibition of proliferation of contaminating fibroblasts by D-valine in cultures of smooth muscle cells from human myometrium," *Cell Biol. Int.*, 2000, 24, 1-7.

Hu, A., et al., "Hepatic differentiation from embryonic stem cells in vitro," *Chin. Med. J.*, 2003, 116(12), 1893-1897.

Hughes, G.C., et al., "Therapeutic angiogenesis in chronically ischemic porcine myocardium: comparative effects of bFGF and VEGF," *Ann. Thorac. Surg.*, 2004, 77, 812-818.

Hutmacher, D.W., "Scaffold design and fabrication technologies for engineering tissues—state of the art and future perspectives," *J. Biomater. Sci. Polymer Edn.*, 2001, 12(1), 107-124.

Isacson, O., et al., "Specific axon guidance factors persist in the adult brain as demonstrated by pig neuroblasts transplanted to the rat," *Neurosci.*, 1996, 75(3), 827-837.

Isacson, O., "The production and use of cells as therapeutic agents in neurodegenerative diseases," *The Lancet (Neurology)*, 2003, 2, 417-424.

Ito, Y., et al., "A quantitative assay using basement membrane extracts to study tumor angiogenesis in vivo," *Int. J. Cancer*, 1996, 67, 148-152.

Jackson, J.A., et al., "Regeneration of ischemic cardiac muscle and vascular endothelium by adult stem cells," *J. Clin. Invest.*, 2001, 107, 1395-1402.

Janderova, L., et al., "Human mesenchymal stem cells as an in vitro model for human adipogenesis," *Obes. Res.*, 2003, 11(1), 65-74.

Jang, Y.K., et al., "Retinoic acid-mediated induction of neurons and glial cells from human umbilical cord-derived hematopoietic stem cells," *J. of Neurosci. Res.*, 2004, 75, 573-584.

Johe, K.K., et al., "Single factors direct the differentiation of stem cells from the fetal and adult central nervous system," *Genes & Devel.*, 1996, 10, 3129-3140.

Johnstone, B., et al., "In vitro chondrogenesis of bone-marrow-derived mesenchymal stem cells," *Exp. Cell Res.*, 1998, 238, 265-272.

Jones-Villeneuve, E.M., et al., "retinoic acid-induced neural differentiation of embryonal carcinoma cells," *Mol. & Cellu. Biol.*, 1983, 3(12), 2271-2279.

Kadiyala, S., et al., "Culture expanded canine mesenchymal stem cells possess osteochondrogenic potential in vivo and in vitro," *Cell Transplant*, 1997, 6(2), 125-134.

Kicic, A., et al., "Differentiation of marrow stromal cells into photoreceptors in the rat eye," *J. of Neurosci.*, 2003, 23(21), 7742-7749.

Kim, S.K., et al., "Intercellular signals regulating pancreas development and function," *Genes Dev.*, 2001, 15, 111-127.

Kim, J.-H., et al., "Dopamine neurons derived from embryonic stem cells function in an animal model of Parkinson's disease," *Nature*, 2002, 418, 50-56.

Kim, J.Y., et al., "Ocular surface reconstruction: limbal stem cell transplantation," *Ophthal. Clin. N Am.*, 2003, 16, 67-77.

Lang, K.J.D., et al., "Differentiation of embryonic stem cells to a neural fate: a route to re-building the nervous system," *J. of Neurosci. Res.*, 2004, 76, 184-192.

Le Belle, J.E., et al., "Stem cells for neurodegenerative disorders: where can we go from here?," *BioDrugs*, 2002, 16, 389-401.

Le Bouteiller, P., et al., "Soluble HLA-G1 at the materno-foetal interface—a review," *Placenta*, 2003, 24 (Suppl. A), S10-S15.

Li, A., et al., "IL-8 directly enhanced endothelial cell survival, proliferation, and matrix metalloproteinases production and regulated angiogenesis," *J. Immunol.*, 2003, 170(6), 3369-3376.

Li, L.X., et al., "Inherited retinal dystrophy in the RCS rat: prevention of photoreceptor degeneration by pigment epithelial cell transplantation," *Exp. Eye Res.*, 1988, 47, 911-917.

Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.

Li, Y., et al., "Transplanted olfactory ensheathing cells promote regeneration of cut adult rat optic nerve axons," *J. of Neuro.*, 2003, 23(21), 7783-7788.

Liu, Y.-J., et al., "Molecular and genetic mechanisms of obesity: implications for future management," *Curr. Mol. Med.*, 2003, 3, 325-340.

Lockhart, et al., "Expression monitoring by hybridization to high-density oligonucleotide arrays," *Nat. Biotechnol.*, 1996, 14(13), 1675-1680.

Lund, R.D., et al., "Subretinal transplantation of genetically modified human cell lines attenuates loss of visual function in dystrophic rats," *Proc. Natl. Acad. Sci. USA*, 2001, 98(17), 9942-9947.

Lund, R.D., et al., "Cell transplantation as a treatment for retinal disease," *Progress in Retinal and Eye Research*, 2001, 20(4), 415-449.

Lund, R.L., et al., "Retinal transplantation: progress and problems in clinical application," *J. Leukocyte Biol.*, 2003, 74, 151-160.

Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.

Mason, A.J., et al., "The hypogonadal mouse: reproductive functions restored by gene therapy," *Science*, 1986, 234, 1372-1378.

Mayer-Proschel, M., et al., "Isolation of lineage-restricted neuronal precursors from multipotent neuroepithelial stem cells," *Neuron.*, 1997, 19, 773-785.

McDonald, J.A., et al., "Diminished responsiveness of male homosexual chronic hepatitis B virus carriers with HTLV-III antibodies to recombinant α-interferon," *Hepatology*, 1987, 7(4), 719-723.

Messina, D.J., et al., "Comparison of pure and mixed populations of human fetal-derived neural progenitors transplanted into intact and adult rat brain," *Exper. Neurol.*, 2003, 184, 816-829.

Mitchell, et al., "Matrix cells from Wharton's jelly form neurons and glia," *Stem Cells*, 2003, 21, 50-60.

Moll, S., et al., "Monitoring warfarin therapy in patients with lupus anticoagulants," *Ann. Intern. Med.*, 1997, 127(3), 177-185.

Mombaerts, et al., "Creation of a large genomic deletion at the T-cell antigen receptor β-subunit locus in mouse embryonic stem cells by gene targeting," *Proc. Nat. Acad. Sci. USA*, 1991, 88, 3084-3087.

Nakamura, T., et al., "Ocular surface reconstruction using cultivated mucosal epithelial stem cells," *Cornea*, 2003, 22(Supp. I), S75-S80.

Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.

Nishida K., et al., "Functional bioengineered corneal epithelial sheet grafts from corneal stem cells expanded ex vivo on a temperature-responsive cell culture surface," *Transplantation*, 2004, 77(3), 379-385.

Nixon, P.J., et al., "The contribution of cone responses to rat electroretinograms," *Clin. Experiment Ophthalmol.*, 2001, 29(3), 193-196.

Nusinowitz, S., et al., "Rod multifocal electroretinograms in mice," *Invest Ophthalmol Vis. Sci.*, 1999, 40(12), 2848-2858.

Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.

Okumoto, K., et al., "Differentiation of bone marrow cells into cells that express liver-specific genes in vitro: implication of the notch signals in differentiation," *Biochem. & Biophys. Res. Commun.*, 2003, 304, 691-695.

Orlic, D., et al., "Stem cells for myocardial regeneration," *Circ. Res.*, 2002, 91, 1092-1102.

Ornitz, D.M., et al., "Elastase I promoter directs expression of human growth hormone and SV40 T antigen genes to pancreatic acinar cells in transgenic mice," *Cold Spring Harbor Symp.Quant. Biol.*, 1985, vol. L, 399-409.

Osborne, N.N., et al., "Some current ideas on the pathogenesis and the role of neuroprotection in glaucomatous optic neuropathy," *Eur. J. Ophthalmol.*, 2003, 13(Supp. 3), S19-526.

Rabbany, S.Y., et al., "Molecular pathways regulating mobilization of marrow-derived stem cells for tissue revascularization," *Trends in Molecular Med.*, 2003, 9(3), 109-117.

Rafii, S., et al., "Therapeutic stem and progenitor cell transplantation for organ vascularization and regeneration," *Nature Med.*, 2003, 9(6), 702-712.

Raman-Cueto, A., et al., "Functional recovery of paraplegic rats and motor axon regeneration in their spinal cords by olfactory ensheathing glia," *Neuron*, 2000, 25, 425-435.

Readhead, C., et al., "Expression of a myelin basic protein gene in transgenic shiverer mice: correction of the dysmyelinating phenotype," *Cell*, 1987, 48, 703-712.

Refaie, A., et al., "Experimental islet cell transplantation in rats: optimization of the transplantation site," *Trans. Proc.*, 1998, 30, 400-403.

Reubinoff, B.E., et al., "Neural progenitors from human embryonic stem cells," *Nature Biotechnology*, 2001, 19, 1134-1140.

Rickard, D.J., et al., "Induction of rapid osteoblast differentiation in rat bone marrow stromal cell cultures by dexamethasone and BMP-2" *Dev. Biol.*, 1994, 161, 218-228.

Romanov, Y.A., et al., "Searching for alternative sources of postnatal human mesenchymal stem cells," *Stem Cells*, 2003, 21, 105-110.

Rosen, E.M., et al., "HGF/SF in angiogenesis," *Ciba Found. Symp.*, 1997, 212, 215-229.

Rutherford, A., et al., "Eyeing-up stem cell transplantation," *Trends in Molecular Medicine*, 2003, 7(1), p. 11.

Sahn, D.J., et al., "Recommendations regarding quantitation in M-Mode echocardiography: results of a survey of echocardiographic measurements," *Circulation*, 1978, 58, 1072-1083.

Sakariassen, K.S., et al., "Methods and models to evaluate shear-dependent and surface reactivity-dependent antithrombotic efficacy," *Thromb. Res.*, 2001, 104, 149-174.

Salcedo, et al., "Human endothelial cells express CCR2 and respond to MCP-1: direct role of MCP-1 in angiogenesis and tumor progression," *Blood*, 2000, 96(1), 34-40.

Sauve, Y., et al., "The relationship between full field electroretinogram and perimetry-like visual thresholds in RCS rats during photoreceptor degeneration and rescue by cell transplants," *Vision Res.*, 2004, 44(1), 9-18.

Schraermeyer, U., et al., "Subretinally transplanted embryonic stem cells rescue photoreceptor cells from degeneration in the RCS rats," *Cell Transplantation*, 2001, 10, 673-680.

Schwartz, R.E., et al., "Multipotent adult progenitor cells from bone marrow differentiate into functional hepatocyte-like cells," *J. of Clin. Invest.*, 2002, 109(10), 1291-1302.

Sebire, G., et al., "In vitro production of IL-6,IL-1 $\beta$, and tumor necrosis factor-alpha by human embryonic microglial and neural cells," *J. Immunol.*, 1993, 150, 1517-1523.

Shani, M., "Tissue-specific expression of rat myosin light-chain 2 gene in transgenic mice," *Nature*, 1985, 314, 283-286.

Shimizu, T., et al., "Cell sheet engineering for myocardial tissue reconstruction," *Biomaterials*, 2003, 24, 2309-2316.

Siminoff, R., et al., "Properties of reptilian cutaneous mechanoreceptors," *Exp. Neurol.*, 1968, 20(3), 403-414.

Sordillo, L.M., et al., "Culture of bovine mammary epithelial cells in D-valine modified medium: selective removal of contaminating fibroblasts," *Cell Biol. Int. Rep.*, 1988, 12, 355-364.

Storch, T.G., "Oxygen concentration regulates 5-azacytidine-induced myogenesis in $C_3H/10T1/2$ cultures," *Biochim. Biophys. Acta*, 1990, 1055, 126-129.

Street, C.N., et al., "Stem cells: a promising source of pancreatic islets for transplantation in type 1 diabetes," *Curr. Top Dev. Biol.*, 2003, 58, 111-136.

Svendsen, C.N., et al., "Long-term survival of human central nervous system progenitor cells transplanted into a rat model of Parkinson's disease," *Experim. Neurol.*, 1997, 148, 135-146.

Svendsen, C.N., "The amazing astrocyte," *Nature*, 2002, 417, 29-32.

Swit, G.H., et al., "Tissue-specific expression of the rat pancreatic elastase I gene in transgenic mice," *Cell*, 1984, 38, 639-646.

Tomita, M., et al., "Bone marrow-derived stem cells can differentiate into retinal cells in injured rat retina," *Stem Cells*, 2002, 20, 279-283.

Tresco, P.A., et al., "Cellular transplants as sources for therapeutic agents," *Advanced Drug Delivery Reviews*, 2000, 42, 3-27.

Tsonis, P.A., et al., "Lens and retina regeneration: transdifferentiation, stem cells and clinical applications," *Experim. Eye Res.*, 2004, 78, 161-172.

Turner, J.F., "Inherited retinal dystrophy in the RCS rat: prevention of photoreceptor degeneration by pigment epithelial cell transplantation," *Exp. Eye Res.*, 1988, 47, 911-917.

Tusher, Vg., et al., "Significance analysis of microarrays applied to the ionizing radiation response," *Proc. Natl. Acad. Sci. USA*, 2001, 98(9), 5116-5121.

Van Hoffelen, S.J., et al., "Incorporation of murine brain progenitor cells into the developing mammalian retina," *Invest. Ophthalmol. Vis. Sci.*, 2003, 44, 426-434.

Vassliopoulos, G., et al., "Transplanted bone marrow regenerates liver by cell fusion," *Nature*, 2003, 422, 901-904.

Villegas-Perez, M.P., et al., "Influences of peripheral nerve grafts on the survival and regrowth of axotomized retinal ganglion cells in adult rats," *J. of Neurosci.*, 1988, 8(1), 265-280.

Von Koskull, H., et al., "Induction of cytokeratin expression in human mesenchymal cells," *J. Cell Physiol.*, 1987, 133, 321-329.

Walboomers, X.F., et al., "Cell and tissue behavior on micro-grooved surfaces," *Odontology*, 2001, 89, 2-11.

Wang, D., et al., "Synthesis and characterization of a novel degradable phosphate-containing hydrogel," *Biomaterials*, 2003, 24, 3969-3980.

Wang, X., et al., "Cell fusion is the principal source of bone-marrow-derived hepatocytes," *Nature*, 2003, 422, 897-900.

Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.

Weiss, M.L., et al., "Transplantation of porcine umbilical cord matrix cells into the rat brain," *Exp. Neur.*, 2003, 182, 288-299.

Bus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539, Wobus.

Odbury, D., et al., "Adult rat and human bone marrow stromal cells differentiate into neurons," *J. of Neurosci. Res.*, 2000, 61, 364-370, Woodbury.

Wulf, G. G. et al., "Mesengenic Progenitor Cells Derived From Human Placenta," *Tissue Engineering*, Larchmont, NY, Jul. 2004, 10(7/8), 1136-1147.

Xu, C., et al., "Characterization and enrichment of cardiomyocytes derived from human embryonic stem cells," *Circ. Res.*, 2002, 91, 501-508.

Yang, H., et al., "Region-specific differentiation of neural tube-derived neuronal restricted progenitor cells after heterotopic transplantation," *PNAS*, 2000, 97(24), 13366-13371.

Yip, H.K., et al., "Axonal regeneration of retinal ganglion cells: effect of trophic factors," *Prog. Retin Eye Res.*, 2000, 19(5), 559-575.

Yu, M., et al., "Mid-trimester fetal blood-derived adherent cells share characteristics similar to mesenchymal stem cells but full-term umbilical cord blood does not," *British J. of Haematology*, 2004, 124, 666-675.

Zangani, D., et al., "Multiple differentiation pathways of rat mammary stromal cells in vitro: acquisition of a fibroblast, adipocyte or endothelial phenotype is dependent on hormonal and extracellular matrix stimulation," *Differentiation*, 1999, 64, 91-101.

Zeng, B.Y., et al., "Regenerative and other responses to injury in the retinal stump of the optic nerve in adult albino rats: transaction of the intracranial optic nerve," *J. Anat.*, 1995, 186, 495-508.

Zhang, S.-C., et al., "In vitro differentiation of transplantable neural precursors from human embryonic stem cells," *Nature Biotechnology*, 2001, 19, 1129-1133.

Auda-Boucher, G., et al., "Staging of the commitment of murine cardiac cell progenitors," *Dev. Bio.*, 2000, 225(1), 214-225 (Abstract 2 pages).

Bao, Z.Z., et al., "Regulation of chamber-specific gene expression in the developing heart by Irx4," *Science*, 1999, 283(5405), 1161-1164 (Abstract 1 page).

Constantini, S., et al., "The effects of methylprednisolone and the ganglioside GM1 on acute spinal cord injury in rats," *J. Neurosurg.*, 1994, 80(1), 97-111 (Abstract 2 pages).

Dawson, T.M., et al., "Neuroprotective and neurorestorative strategies for Parkinson's disease," *Nat. Neurosci.*, 2002, 5 Suppl., 1058-1061 (Abstract 1 page).

Eisenhofer, G., et al., "Tyrosinase: a developmentally specific major determinant of peripheral dopamine," *FASEB J.*, 17, 248-255.

Klassen H., et al., "Stem cells and retinal repair," *Prog. Retin. Eye Res.*, 2004, 23(2), 149-181 (Abstract 1 page).

Laface, D., et al., "Gene transfer into hematopoietic progenitor cells mediated by an adeno-associated virus vector," *Virology*, 1998, 162, 483-486.

MacDonald, R.J., "Expression of the pancreatic elastase I gene in transgenic mice," *Hepatology*, 1987, 7(1), 42S-51S.

Morgenstern, J.P., et al., "Advanced mammalian gene transfer: high titre retroviral vectors with multiple drug selection markers and a complementary helper-free packaging cell line," *Nucleic Acids Res.*, 1990, 18(12), 3587-3596.

Reyes, M., et al., "Purification and ex vivo expansion of postnatal human marrow mesodermal progenitor cells," *Blood*, 2001, 98(9), 2615-2625.

Rezai et al., "Iris pigment epithelium transplantation," *Graefes Arch. Clin. Ophthalmol.*, 1997, 235(9), 558-562.

Xu, Y., et al., "Dopamine, in the presence of tyrosinase, covalently modifies and inactivates tyrosine hydroxylase," *J. Neurosci. Res.*, 1998, 54(5), 691-697 (Abstract 3 pages).

Hoynowski, S. M. et al., Characterization and differentiation of equine umbilical cord-derived matrix cells. Biochemical and Biophysical Research Communications, Aug. 2007, 362, 347-353.

Merriam-Webster Medline Plus Online Medical Dictionary, definitions of "iliac", "ilium" ileal/ileac and "ileum". [online] [retrieved on Feb. 13, 2008]. Retrieved from the Internet: URL://www.nlm.nih.gov/medlineplus/mplusdictionary.html.

Abbas, A.K., Lichtman, A.H., *Cellular and Molecular Immunology*, 5th Ed. (2003) Saunders, Philadelphia, p. 171.

Agbulut, O. et al., "Comparison of Human Skeletal Myoblasts and Bone Marrow-Derived CD 133+ Progenitors for the Repair of Infarcted Myocardium," *Journal of the American College of Cardiology*, 2004, 44(2), 458-463.

Aldskogius, H. et al., "Strategies for repair of the deafferented spinal cord," *Brain Res. Rev.*, 2002, 20, 301-308.

Armulik A et al., "Endothelial/Pericyte Interactions," *Circ. Res.*, 2005, 97, 512-23.

Bergers G. et al., "The role of pericytes in blood-vessel formation and maintenance," *Neuro-Oncology*, 7, 452-464.

Bhindi, R. et al., "Rat models of mycocardial infarction," *Thromb Haemost*, 2006, 96, 602-610.

Blakemore, W. F. et al., "Modelling Large Areas of Demyelination in the Rat Reveals the Potential and Possible Limitations of Transplanted Glial Cells for Remyelination in the CNS," *GLIA*, 2002, 38, 155-168.

Daley, G. Q. et al., "Realistic Prospects for Stem Cell Therapeutics," *Hematol.*, 2003, 398-418.

Doyle, J., "Spiraling complexity, robustness, and fragility in biology," http://www.cds.caltech.edu/~doyle/CmplxNets/Biol.pdf, available online Feb. 28, 2004.

Eagle, H., "The specific amino acid requirements of a mammalian cell (strain L) in tissue culture," *J. Biol. Chem.*, Jun. 1995, 214(2), 839-852.

Edelstein, M. L. et al., "Gene therapy clinical trials worldwide 1989-2004—an overview," *J. Gene Med.*, Jun. 2004, 6(6), 597-602.

Foley, A. et al., "Heart induction: embryology to cardiomyocyte regeneration," *Trends Cardiovasc Med.*, Apr. 2004, 14(3), 121-125.

Goodwin, H. S. et al., "Multilineage differentiation activity by cells isolated from umbilical cord blood: Expression of bone, fat and neural markers," *Biology of Blood and Marrow Transplantation*, 2001, 7, 581-588.

Hill, M. et al., "Treatment for swallowing difficulties (dysphagia) in chronic muscle disease," *Cochrane Database Syst Rev.*, 2004, (2):CD004303.

Holz, F. G. et al., "Intraocular microablation of choroidal tissue by a 308 nm AIDA excimer laser for RPE-transplantation in patients with age-related macular degeneration," *Biomed Tech* (Berlin), Apr. 2003, 48(4), 82-85.

Ishii, M. et al., "Molecular markers distinguish bone marrow mesenchymal stem cells from fibroblasts," *Biochemical and Biophysical Research Communications*, Jun. 24, 2005, 332(1), 297-303.

Jaffe, E. A. et al., "Culture of human endothelial cells derived from umbilical veins," *J Clin Invest*, 1973, 52, 2745-2756.

Jikuhara, T. et al., "Left atrial function as a reliable predictor of exercise capacity in patients with recent myocardial infarction," *Chest*, Apr. 1997, 111(4), 922-928.

Jomura, S., et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Joussen, A. M., "Cell transplantation in age related macular degeneration: current concepts and future hopes," *Graefe's Arch. Clin. Exp. Ophthalmol.*, 2004, 242, 1-2.

Kawata, M. et al., "Transcriptional control of HLA-A,B,C antigen in human placental cytotrophoblast isolated using trophoblast- and HLA-specific monoclonal antibodies and the fluorescence-activated cell sorter," *J. Exp. Med.*, Sep. 1984, 160, 633-651.

Kirschstein, R. et al., "Can stem cells repair a damaged heart?" *Stem Cells: Scientific Progress and Future Research Directions*, 2001, 87-92.

Langeggen, H. et al., "HUVEC take up opsonized zymosan particles and secrete cytokines IL-6 and IL-8 in vitro," *FEMS Immunol. Med. Microbiol.*, 2003, 36, 55-61.

Lindvall, O. et al., "Stem cell therapy for human neurodegenerative disorders—how to make it work," *Nature Medicine*, Jul. 2004, 542-550.

Lodie, T. A. et al., "Systematic Analysis of Reportedly Distinct Populations of Mulitpotent Bone Marrow-Derived Stem Cells Reveals a Lack of Distinction," *Tissue Engineering*, Oct. 2002, 8(5), 739-751.

Luo, D. et al., "Synthetic DNA delivery systems," *Nat. Biotechnol.*, Jan. 2000, 18(1), 33-36.

Luyten, F. P. et al., "Skeletal tissue engineering: opportunities and challenges," *Best Pract. Res. Clin. Rheumatol.*, Dec. 2001, 15(5), 759-769.

Medicetty, S. et al., "Transplantation of Human Umbilical Cord Matrix Stem Cells Alleviates Apomorphine-Induced Rotations in Parkinsonian Rats", 2003, XP-002383776, 1 page.

Medline Plus Online Medical Dictionary, definitions of "undifferentiated," and "differentiate," and "differentiation" Retrieved online Mar. 6, 2007. URL:www.nlm.nih.gov/medlineplus/mplusdictionary.html.

Merx, M. W. et al., "Transplantation of human umbilical vein endothelial cells improves left ventricular function in a rat model of myocardial infarction," *Basic Res. Cardiol.*, 2005, 100, 208-216.

Moulder, J. E., "Pharmacological intervention to prevent or ameliorate chronic radiation injuries," *Semin. Radiat. Oncol.*, 2003, 13, 73-84.

Nishishita, T. et al., "A potential pro-angiogenic cell therapy with human placenta-derived mesenchymal cells," *Biochemical and Biophysical Research Communications*, 2004, 325, 24-31.

Nork, T. M. et al., "Swelling and Loss of Photoreceptors in Chronic and Experimental Glaucomas," *Arch. Ophthalmol.*, 2000, 118, 235-245.

Palu, G. et al., "In pursuit of new developments for gene therapy of human disease," *J. Biotechnol.*, Feb. 1999, 68(1), 1-13.

Phipps, J. A. et al., "Paired-flash identification of rod and cone dysfunction in the diabetic rat," *Investigative Ophthalmology & Visual Science*, 2004, 45(12), 4592-4600.

Pittenger, M. F. et al., "Multilineage potential of adult human mesenchymal stem cells," *Science*, 1999, 284, 143-147 and seven pages of online supplementary material.

Pittenger, M. F. et al., "Mesenchymal Stem Cells and Their Potential as Cardiac Therapeutics," *Circ. Res.*, 2004, 95, 9-20.

Qian Ye et al., "Recovery of Placental-Derived Adherent Cells with Mesenchymal Stem Cell Characteristics", *Blood*, 2001, 98(11 Part 2), p. 147B, Abstract No. 4260.

Rehman, J. et al., "Secretion of Angiogenic and Antiapoptotic Factors by Human Adipose Stromal Cells," *Circulation*, 2004, 109, 1292-1298.

Rios, M., et al., "Catecholamine Synthesis is Mediated by Tyrosinase in the Absence of Tyrosine Hydroxylase," *J. Neurosci.*, 1999, 3519-3526.

Roskams, A. J. et al., "Directing stem cells and progenitor cells on the stage of spinal cord injury," *Exp. Neurol.*, 2005, 193, 267-272.

Salgado, A. J. et al., "Bone Tissue Engineering: State of the Art and Future Trends," *Macromol. Biosci.*, Aug. 2004, 4, 743-765.

Sethe, S. et al., "Aging of mesenchymal stem cells," *Ageing Research Reviews*, 2006, 5, 91-116.

Taylor, D. A. et al., "Regenerating functional myocardium: Improved performance after skeletal myoblast transplantation," *Nature Medicine*, Aug. 1998, 4(8), 929-933. Erratum in *Nature Medicine*, 4(10), 1200.

Taylor, D. A. et al., "Cardiac chimerism as a mechanism for self-repair: does it happen and if so to what degree?" *Circulation*, Jul. 2002, 106(1), 2-4.

Timmermans et al., "Stem cells for the heart, are we there yet?" *Cardiology*, 2003, 100(4), 176-185.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001, 19, 408-418.

Unigene entry for Hs.522632, *Homo sapiens* TMP metallopeptidase inhibitor 1 (TIMP1), printed from http://www.ncbi.nlm.nih.gov/UniGene on Oct. 12, 2006.

Urbich, C. et al., "Endothelial Progenitor Cells,", *Circ. Res.*, 2004, 95, 343-353.

Vajsar, J. et al., "Walker-Warburg syndrome," *Orphanet Journal of Rare Diseases*, 2006, 1, 29.

Verma, I. M. et al., "Gene therapy—promises, problems and prospects," *Nature*, Sep. 1997, 389(6648), 239-242.

Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.

Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.

Woodbury, D., et al., "Adult rat and human bone marrow stromal cells differentiate into neurons," *J. of Neurosci. Res.*, 2000, 61, 364-370.

Yang Chen et al., "Enhancement of neovascularization with cord blood CD133+ cell-derived endothelial progenitor cell transplantation," *Thrombosis and Haemostasis*, Jun. 2004, 91(6), 1202-1212.

Yokoo, T. et al., "Stem cell gene therapy for chronic renal failure," *Curr Gene Ther.*, 2003, 3, 387-394.

Zimmermann, S. et al., "Lack of telomerase activity in human mesenchymal stem cells," *Leukemia*, 2003, 17, 1146-1149.

Zuloff-Shani, A. et al., "Macrophage suspensions prepared from a blood unit for treatment of refractory human ulcers," *Transfus Apheresis Sci.* 2004, 30(2), 163-167.

Franc, S. et al., "Microfibrillar composition of umbilical cord matrix: characterization of fibrillin, collagen VI and intact collagen V," *Placenta*, 1988, 19, 95-104.

Mackay et al., "Chondrogenic differentiation of cultured human mesenchymal stem cells from marrow," *Tissue Engineering*, 1998, 4(4), 415-428.

Aggarwal et al., "Human Mesenchymal Stem Cells Modulate Allogeneic Immune Cell Responses," *Blood*, 2005; 105(4):1815-22.

Aston, J. E., et al., "Repair of Articular Surfaces by Allografts of Articular and Growth-Plate Cartilage," *Journal of Bone and Joint Surgery*, 1986; 68-B(1):29-35.

Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-10.

Bradley, B.A., "The Role of HLA Matching in Transplantation," *Immunol. Lett.*, 1991; 29:55-59.

Bussolati et al., "Isolation of Renal Progenitor Cells from Adult Human Kidney," *American Journal of Pathology*, 2005; 166(2):545-55.

Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.

Chen, H. et al., "The Effect of Hypothermia on Transient Middle Cerebral Artery Occlusion in the Rat," *J. Cereb. Blood Flow Metab.*, 1992; 12(4):621-28.

Chen, J. et al., "Therapeutic Benefit of Intravenous Administration of Bone Marrow Stromal Cells after Cerebral Ischemia in Rats," *Stroke*, 2001; 32(4):1005-11.

del Monte, F. et al., "Improvement In Survival And Cardiac Metabolism After Gene Transfer Of Sarcoplasmic Reticulum Ca $^{2+}$-ATPase In A Rat Model Of Heart Failure," *Circulation*, 2001;104:1424-29.

Dickinson, A.M. et al., "Non-HLA Immunogenetics in Hematopoietic Stem Cell Transplantation," *Curr. Opin. Immunol.*, 2005; 17(5):517-25.

Fernandes;A.M. et al., "Mouse Embryonic Stem Cell Expansion in a Microcarrier-based Stirred Culture System," *Journal of Biotechnology*, 2007; 132(2): 227-36.

Gröhn, P. et al., "Collagen-Coated BA$^{2+}$-Alginate Microcarriers for the Culture of Anchorage-Depndent Mammalian Cells," *BioTechniques*, 1997; 22(5): 970-75.

Gupta, S. et al., "Isolation and Characterization of Kidney-Derived Stem Cells," *J. of Am. Soci. of Nephrol.*, 2006; 17(11):3028-40.

Hartgerink, J.D. et al., "Peptide-Amphiphile Nanofibers: A Versatile Scaffold for the Preparation of Self-Assembling Materials," *PNAS*, 2002; 99(8):5133-38.

Herrera, M.B. et al., "Mesenchymal Stem Cells Contribute to the Renal Repair of Acute Tubular Epithelial Injury," *Int J. Mol. Med.*, 2004; 14(6):1035-41.

Hill, D.P. et al., "Screening for Novel Pattern Formation Genes Using Gene Trap Approaches," *Methods in Enzymology*, 1993; 225:664-81.

Hishikawa, K. et al., "Musculin/MyoR is Expressed in Kidney Side Population Cells and Can Regulate Their Function," *Journal of Cell Biology*, 2005; 169(6):921-28.

In't Anker, P., et al., "Isolation of Mesenchymal Stem Cells of Fetal or Maternal Origin from Human Placenta," *Stem Cells*, 2004; 22:1338-45.

Jo,Y.W. et al., "Use of Pharmasep Unit for Processing Microspheres," *AAPS PharmSciTech*, 2001; 2(1):Technical Note 2.

Jones, J. et al., "Insulin-Like Growth Factors and their Binding Proteins: Biological Actions," *Endocrine Review*, 1995; 16(1):3-34.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-80.

Kisiday, J. et al., "Self-Assembling Peptide Hydrogel Fosters Chondrocyte Extracellular Matrix Production And Cell Division: Implications For Cartilage Tissue Repair," *PNAS*, 2002; 99(15):9996-10001.

Kokufuta, E. et al., "Effects of Surfactants on the Phase Transition of Poly(N-isopropylacrylamide) Gel," *Macromolecules*, 1993; 26:1053-59.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-48.

Kushida, A., et al., "Decrease in Culture Temperature Releases Monolayer Endothelial Cell Sheets Together with Deposited Fibronectin Matrix from Temperature-Responsive Culture Surfaces," *J. of Biomedical Materials Research*, 1999; 45(4):355-62.

Li, C.D. et al, "Mesenchymal Stem Cells Derived From Human Placenta Suppress Allogeneic Umbilical Cord Blood Lymphocyte Proliferation," *Cell Research*, 2005; 15(7):539-47.

Li, Y. et al., "Intact, Injured, Necrotic and Apoptotic Cells after Focal Cerebral Ischemia in the Rat," *J. Neurol. Sci.*, 1998; 156(2):119-32.

Li, Y. et al., "Ultrastructural and Light Microscopic Evidence of Apoptosis after Middle Cerebral Artery Occlusion in the Rat," *Am. J. Pathol.*, 1995; 146(5):1045-51.

Lindenlaub, T. et al., "Partial Sciatic Nerve Transection as a Model of Neuropathic Pain: A Qualitative and Quantitative Study," *Pain*, 2000; 89(1): 97-106.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-93.

Ma, P.X . et al., "Synthetic Nano-Scale Fibrous Extracellular Matrix ," *J. Biomed Mater Res.*, 1999; 46(1):60-72.

Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-98.

Melero-Martin, J. et al., "Optimal In-Vitro Expansion of Chondroprogenitor Cells in Monolayer Culture," *Biotechnology and Bioengineering*, 2006; 93(3):519-33.

*Merriam-Webster Online Dictionary 10$^{th}$ Edition*, Definition Of "Scaffold" (retrieved Sep. 12, 2008).

Moore, A.E. et al., "Parkinsonian Motor Deficits are Reflected by Proportional A9/A10 Dopamine Neuron Degeneration in the Rat," *Exp. Neurol.*, 2001; 172(2):363-76.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-06.

Newman, K.D. et al., "Poly(D,L lactic-co-glycolic acid) Microspheres as Biodegradable Microcarriers for Pluripotent Stem Cells," *Biomaterials*, 2004; 25:5763-71.

Oliver, J.A. et al., "The Renal Papilla is a Niche for Adult Kidney Stem Cells," *J. Clin Invest.*, 2004, 114(6):795-804.

Panepucci, R.A. et al., "Comparison of Gene Expression of Umbilical Cord Vein and Bone Marrow-Derived Mesenchymal Stem Cells," *Stem Cells*, 2004; 22(7):1263-78.

Pera, M.F. et al., "Human Embryonic Stem Cells", *J. Cell Science*, 2000; 113:5-10.

Petersdorf, E.W., "HLA Matching in Allogeneic Stem Cell Transplantation," *Curr. Op. Hematol.*, 2004; 11(6):386-91.

Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-33.

Plaia, T., et al., "Characterization Of A New NIH-Registered Variant Human Embryonic Stem Cell Line, BG01V: A Tool For Human Embryonic Stem Cell Research," *Stem Cells*, 2006: 24(3): 531-46.

Pountos, I. et al., "Mesenchymal Stem Cell Tissue Engineering: Techniques for Isolation, Expansion and Application," *Injury*, 2007; 38(Supp. 4):S23-33.

Quaini, F. et al., "Chimerism Of The Transplanted Heart," *NEJM*, 2002; 346:5-15.

Russo, E., Cultivating Policy from Cell Types, *The Scientist*, 2001; 15(11):6 (printout is numbered 1-6).

Sagrinati, C. et al., "Isolation and Characterization of Multipotent Progenitor Cells from the Bowman's Capsule of Adult Human Kidney," *Journal of American Society of Nephrology*, 2006; 17(9)2443-56.

Schallert, T. et al., "Use-Dependent Structural Events in Recovery of Function," *Brain Plasticity, Adv. Neurol.*, 1997; 73:229-38.

Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.

Shuto, T. et al., "Dexamethasone Stimulates Osteoclast-Like Cell Formation By Inhibiting Granulocyte-Macrophage Colony-Stimulating Factor Production In Mouse Bone Marrow Cultures," *Endocrinology*, 1994; 134(3):1121-26.

Song, H. et al., "Astroglia Induce Neurogenesis From Adult Neural Stem Cells," *Nature*, 2002; 417(6884):39-44.

Swanson, R.A. et al., "A Semiautomated Method for Measuring Brain Infarct Volume," *J. Cereb. Blood Flow Metab.*, 1990; 10(2):290-93.

Tao, W., "Application Of Encapsulated Cell Technology For Retinal Degenerative Disease", *Expert. Opin. Biol. Ther.*, 2006; 6(7): 717-26.

Toma, C. et al., "Human Mesenchymal Stem Cells Differentiate To A Cardiomyocyte Phenotype In The Adult Murine Heart," *Circulation* 2002; 105:93-98.

Trenka-Benthin, S., "Cell Therapy of Stroke Study: Rat #B-31," *Testicular Lesion Histology Report and Photomicropgraph Indexes*, 2005; pp. 1-3.

Turner, D., "The Human Leucocyte Antigen (HLA) System," *Vox Sang.*, 2004; 87(Suppl 1):S87-S90.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

Webster, T.J. et al., "Nanoceramic Surface Roughness Enhances Osteoblast And Osteoclast Functions For Improved Orthopaedic/Dental Implant Efficacy," *Scripta Materialia*, 2001; 44(8/9):1639-42.

Wenning, G.K. et al., "Neural Transplantation in Animal Models of Multiple System Atrophy: A Review," *J. Nueral Transm.*, 1999; Suppl.(55):103-13.

*Wikipedia*, Definition of "Iliac crest" provided by Wikipedia, the free encyclopedia; retrieved from the Internet at URL: http://en.wikipedia.org/wiki/Iliac_crest; downloaded on Dec. 18, 2007.

Williams, J.T. et al., "Cells Isolated From Adult Human Skeletal Muscle Capable Of Differentiating Into Multiple Mesodermal Phenotypes," *Am. Surg.* Jan. 1999:65(I):22-26.

Wolford, L.M. et al., "Considerations In Nerve Repair," *BUMC Proceedings*, 2003; 16:152-56.

Xu, A. et al., "Soft, Porous Poly(D,L lactide-co-glycotide) Microcarriers Designed for Ex Vivo Studies and for Transplantation of Adherent Cell Types including Progenitors," *Annals of the New York Academy of Sciences*, 2001; 944:144-59.

Zhang, L. et al., "A Test for Detecting Long-Term Sensorimotor Dysfunction in the Mouse after Focal Cerebral Ischemia," *J. Neurosci. Methods*, 2002; 117(2):207-14.

Zhang, X. et al., "Efficient Adeno-Associated Virus-Mediated Gene Expression in Human Placenta-Derived Mesenchymal Cells," *Microbiol. Immunol.*, 2003; 47(1):109-16.

Zhang, Y. et al., "Comparison of Mesenchymal Stem Cells from Human Placenta and Bone Marrow," *Chinese Medical Journal*, 2004; 117(6):882-87.

Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-92.

In the U.S. Patent and Trademark Office, Non-Final Office Action in re: U.S. Appl. No. 10/877,012, dated Sep. 24, 2007, 18 pages.

In the U.S. Patent and Trademark Office, Final Office Action in re: U.S. Appl. No. 10/877,012, dated Mar. 15, 2007, 13 pages.

In the U.S. Patent and Trademark Office, Non-Final Office Action in re: U.S. Appl. No. 10/877,012, dated Jul. 18, 2006, 26 pages.

In the U.S. Patent and Trademark Office, Non-Final Office Action in re: U.S. Appl. No. 11/315,897, dated Jun. 13, 2008, 12 pages.

In the U.S. Patent and Trademark Office, Non-Final Office Action in re: U.S. Appl. No. 10/877,446, dated Feb. 28, 2008, 19 pages.

In the U.S. Patent and Trademark Office, Final Office Action in re: U.S. Appl. No. 10/877,446, dated Jun. 27, 2007, 24 pages.

In the U.S. Patent and Trademark Office, Non-Final Office Action in re: U.S. Appl. No. 10/877,446, dated Nov. 20, 2006, 24 pages.

In the U.S. Patent and Trademark Office, Non-Final Office Action in re: U.S. Appl. No. 10/877,269, dated Jan. 17, 2008, 10 pages.

In the U.S. Patent and Trademark Office, Final Office Action in re: U.S. Appl. No. 10/877,269, dated Aug. 14, 2007, 6 pages.

In the U.S. Patent and Trademark Office, Non-Final Office Action in re: U.S. Appl. No. 10/877,269, dated May 3, 2007, 12 pages.

In the U.S. Patent and Trademark Office, Final Office Action in re: U.S. Appl. No. 11/315,943, dated Aug. 20, 2008, 7 pages.

In the U.S. Patent and Trademark Office, Non-Final Office Action in re: U.S. Appl. No. 11/315,943, dated Feb. 12, 2008, 11 pages.

In the U.S. Patent and Trademark Office, Non-Final Office Action in re: U.S. Appl. No. 10/877,445, dated Jul. 11, 2008, 12 pages.

In the U.S. Patent and Trademark Office, Non-Final Office Action in re: U.S. Appl. No. 10/877,445, dated Mar. 19, 2008, 12 pages.

In the U.S. Patent and Trademark Office, Final Office Action in re: U.S. Appl. No. 10/877,445, dated Nov. 5, 2007, 17 pages.

In the U.S. Patent and Trademark Office, Non-Final Office Action in re: U.S. Appl. No. 10/877,445, dated May 17, 2007, 20 pages.

In the U.S. Patent and Trademark Office, Final Office Action in re: U.S. Appl. No. 10/877,445, dated Sep. 11, 2006, 30 pages.

In the U.S. Patent and Trademark Office, Non-Final Office Action in re: U.S. Application No. 10/877,445, dated Nov. 21, 2005, 17 pages.

In the U.S. Patent and Trademark Office, Non-Final Office Action in re: U.S. Application No. 11/322,372, dated Sep. 3, 2008, 13 pages.

In the U.S. Patent and Trademark Office, Non-Final Office Action in re: U.S. Appl. No. 10/877,541, dated Jul. 25, 2007, 13 pages.

In the U.S. Patent and Trademark Office, Advisory Office Action in re: U.S. Appl. No. 10/877,541, dated Apr. 18, 2007, 4 pages.

In the U.S. Patent and Trademark Office, Final Office Action in re: U.S. Appl. No. 10/877,541, dated Jan. 10, 2007, 19 pages.

In the U.S. Patent and Trademark Office, Non-Final Office Action in re: U.S. Appl. No. 10/877,541, dated Feb. 22, 2006, 13 pages.

In the U.S. Patent and Trademark Office, Advisory Office Action in re: U.S. Appl. No. 11/317,574, dated Jun. 4, 2008, 3 pages.

In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091 dated Feb. 23, 2007, 9 pages.
In the United States Patent and Trademark Office, Non-Final Office Action in re: U.S. Appl. No. 11/323,372, dated Sep. 3, 2008, 45 pages.
In the United States Patent and Trademark Office, Non-Final Office Action, in re: U.S. Appl. No. 11/297,156, dated Oct. 10, 2008, 36 pages.
In the United States Patent and Trademark Office, Non-Final Office Action in re: U.S. Appl. No. 11/317,574, dated Sep. 30, 2008, 28 pages.
In the U. S. Patent and Trademark Office, Non-Final Office Action in re: U.S. Appl. No. 11/315,969, dated Dec. 23, 2008, 18 pages.
In the U. S. Patent and Trademark Office, Non-Final Office Action in re: U.S. Appl. No. 10/951,357, dated Nov. 26, 2008, 25 pages.
In the U. S. Patent and Trademark Office, Non-Final Office Action in re: U.S. Appl. No. 11/321,864, dated Jan. 8, 2009, 34 pages.
In the U. S. Patent and Trademark Office, Final Office Action in re: U.S. Appl. No. 11/321,863, dated Feb. 12, 2009, 24 pages.
In the U. S. Patent and Trademark Office, Non-Final Office Action in re: U.S. Appl. No. 11/315,943, dated Feb. 20, 2009, 17 pages.
In the U. S. Patent and Trademark Office, Non-Final Office Action in re: U.S. Appl. No. 11/611,602, dated Mar. 3, 2009, 18 pages.
In the U. S. Patent and Trademark Office, Non-Final Office Action in re: U.S. Appl. No. 11/297,778, dated Mar. 9, 2009, 12 pages.
In the U. S. Patent and Trademark Office, Non-Final Office Action in re: U.S. Appl. No. 10/877,445, dated Mar. 19, 2009, 23 pages.
In the U. S. Patent and Trademark Office, Non-Final Office Action in re: U.S. Appl. No. 11/481,481, dated Mar. 20, 2009, 48 pages.
In the U. S. Patent and Trademark Office, Final Office Action in re: U.S. Appl. No. 11/315,897, dated Mar. 20, 2009, 21 pages.
In the U. S. Patent and Trademark Office, Non-Final Office Action in re: U.S. Appl. No. 11/481,480, dated Mar. 20, 2009, 50 pages.
In the U. S. Patent and Trademark Office, Final Office Action in re: U.S. Appl. No. 11/322,003 dated Feb. 13, 2009, 24 pages.
In the U. S. Patent and Trademark Office, Final Office Action in re: U.S. Appl. No. 10/876,998 dated Feb. 13, 2009, 18 pages.
In the U. S. Patent and Trademark Office, Final Office Action in re: U.S. Appl. No. 11/322,372 dated Feb. 13, 2009, 22 pages.
In the U. S. Patent and Trademark Office, Non-Final Office Action in re: U.S. Appl. No. 11/304,091 dated Feb. 27, 2009, 36 pages.
In the U. S. Patent and Trademark Office, Non-Final Office Action in re: U.S. Appl. No. 11/481,456 dated Apr. 16, 2009, 50 pages.
In the U. S. Patent and Trademark Office, Non-Final Office Action in re: U.S. Appl. No. 11/317,574dated Apr. 29, 2009, 29 pages.
In the U. S. Patent and Trademark Office, Non-Final Office Action in re: U.S. Appl. No. 11/817,045 dated Apr. 27, 2009, 12 pages.
In the U. S. Patent and Trademark Office, Non-Final Office Action in re: U.S. Appl. No. 11/297,156 dated Apr. 28, 2009, 40 pages.
In the U.S. Patent and Trademark Office, Non-Final Office Action in re: U.S. Appl. No. 11/315,943 dated Feb. 19, 2010, 15 pages.
European Office Action issued Sep. 7, 2009 in European Patent Application No. 05855443.7.

* cited by examiner

TREATMENT OF STROKE AND OTHER ACUTE NEURALDEGENERATIVE DISORDERS USING POSTPARTUM DERIVED CELLS

CROSS-REFERENCE TO RELATED APPLICATIONS

This is a continuation-in-part of U.S. application Ser. No. 10/877,269, filed Jun. 25, 2004, which claims benefit of U.S. Provisional Application No. 60/483,264, filed Jun. 27, 2003, the entire contents of both of which are incorporated by reference herein. This also claims benefit of U.S. Provisional Application 60/638,966, filed Dec. 23, 2004, the entire contents of which are incorporated by reference herein.

FIELD OF THE INVENTION

This invention relates to the field of cell based or regenerative therapy for stroke patients. In particular, the invention provides cells derived from postpartum tissue having the capability to regenerate, repair, and improve neural tissue and to improve behavior and neurological function in stroke patients or patients suffering from other forms of acute neurological stress or damage, and methods for using such postpartum tissue-derived cells to regenerate, repair, and improve neural tissue and to improve behavior and neurological function in such individuals.

BACKGROUND OF THE INVENTION

Various publications, including patents, published applications, technical articles and scholarly articles are cited throughout the specification. Each of these cited publications is incorporated by reference herein, in its entirety.

In the United States, strokes strikes 700,000 people annually. Of these stroke patients, 40% will die, the equivalent of one death every three minutes. Fifty percent of stroke-related deaths occur in the hospital.

Two of the most common strokes are ischemic and hemorrhagic strokes. In ischemic strokes, a lack of oxygen flow to the brain can result in apoptosis and necrosis of brain tissue leading to an infarction. Similar to cardiovascular ischemia, brain ischemia can be caused by various factors such as blood clots, thrombosis, embolism, blockage by atherosclerotic plaques, or other obstructions in the vasculature. Hypercholesterolemia, hypertension, diabetes, and obesity, among other things, have been identified as risk factors for ischemic strokes. Ischemic strokes are a leading cause of death of human beings worldwide. Hemorrhagic strokes, which account for between about 10 and 20 percent of all strokes, are typically caused by a ruptured blood vessel in the brain. The rupture causes bleeding into the brain, where the accumulating blood can damage surrounding neural tissues.

The stroke episode, regardless of its cause, results in neural cell death, especially at the location of the obstruction or hemorrhage. In addition, biochemical reactions that occur subsequent to the stroke episode in the vasculature may lead to edema, hemorrhagic transformation, and a further compromise in neurological tissue. The neurological damage and neuron cell death that result from a stroke can be physically and mentally debilitating to an individual. Among other things, a stroke can result in problems with emotional control, awareness, sensory perception, speech, hearing, vision, cognition, movement and mobility, and can cause paralysis.

Neurological damage and neurodegenerative diseases were long thought to be irreversible because of the inability of neurons and other cells of the nervous system to grow in the adult body. However, the recent advent of stem cell-based therapy for tissue repair and regeneration provides promising treatments for a number of neurodegenerative pathologies and other neurological disorders. Stem cells are capable of self-renewal and differentiation to generate a variety of mature neural cell lineages. Transplantation of such cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of biotherapeutic agents to a target location via exogenously supplied living cells or cellular components that produce or contain those agents (For a review, see Tresco, P. A. et al., (2000) *Advanced Drug Delivery Reviews* 42:2-37). The identification of stem cells has stimulated research aimed at the selective generation of specific cell types for regenerative medicine.

Cell transplantation to replace lost neurons is a new approach to the treatment of the neurological damage that results from a stroke. One obstacle to realization of the therapeutic potential of stem cell technology has been the difficulty of obtaining sufficient numbers of stem cells. Embryonic, or fetal tissue, is one source of stem cells. Embryonic stem and progenitor cells have been isolated from a number of mammalian species, including humans, and several such cell types have been shown capable of self-renewal and expansion, as well differentiation into all neurological cell lineages (Svendsen, C. V. et al. (1997) *Exp. Neurol.* 148:135-146; Freed, C. R. et al. (2001) *New Engl J. Med* 344(10):-719; Burnstein, R. M. et al. (2003) *Int. J. Biochem. Cell Biol.* 36:702-713; Zhang, S-C. et al. (2001) *Nat. Biotechnol.* 19:1129-1133; Reubinoff, B. E. et al. (2001) *Nat. Biotechnol.* 19:1134-1140; Björklund, L. M. et al. (2002) *Proc. Natl. Acad. Sci. USA* 99(4):2344-2349). But the derivation of stem cells from embryonic or fetal sources has raised many ethical and moral issues that are desirable to avoid by identifying other sources of multipotent or pluripotent cells.

Stem cells with neural potency also have been isolated from adult tissues. Neural stem cells exist in the developing brain and in the adult nervous system. These cells can undergo expansion and can differentiate into neurons, astrocytes and oligodendrocytes. However, adult neural stem cells are rare, as well as being obtainable only by invasive procedures, and may have a more limited ability to expand in culture than do embryonic stem cells.

Other adult tissue may also yield progenitor cells useful for cell-based neural therapy. For instance, it has been reported recently that adult stem cells derived from bone marrow and skin can be expanded in culture and give rise to multiple lineages, including some neural lineages (Azizi, S. A. et al. (1998) *Proc. Natl. Acad. Sci. USA* 95:3908-3913; Li, Y. et al. (2001) *Neurosci. Lett.* 315:67-70). Intrastriatal and intranigral grafting of other cell types, such as neurons derived from human teratocarcinoma, and human umbilical cord blood mononuclear cells have also been tested in animal models of Parkinson's disease (Baker, K. A. et al. (2000) *Exp. Neurol.* 162:350-360; Ende, N. and R. Chen (2002) *J. Med.* 33(1-4): 173-180).

Postpartum tissues, such as the umbilical cord and placenta, have generated interest as an alternative source of stem cells. For example, methods for recovery of stem cells by perfusion of the placenta or collection from umbilical cord blood or tissue have been described. A limitation of stem cell procurement from these methods has been an inadequate volume of cord blood or quantity of cells obtained, as well as heterogeneity in, or lack of characterization of, the populations of cells obtained from those sources.

Thus, alternative sources of adequate supplies of cells having the ability to differentiate into an array of neural cell lineages remain in great demand. Further, no satisfactory method exists to repair the neural, neurological, and behavioral damage caused by strokes. Strokes can affect the motor system, rendering the patient with symptoms of hemiparesis or paralysis. Thus, a reliable, well-characterized and plentiful supply of substantially homogeneous populations of cells having the ability to differentiate into an array of neural cell lineages would be an advantage in a variety of diagnostic and therapeutic applications for neural repair, regeneration, and improvement, as well as applications for improvements in behavior and neurological function, particularly in stroke patients.

SUMMARY OF THE INVENTION

One aspect of the invention features a method of treating a patient having an acute neurodegenerative condition, which comprises administering to the patient postpartum-derived cells in an amount effective to treat the neurodegenerative condition, wherein the postpartum-derived cells are derived from human placental or umbilical cord tissue substantially free of blood, wherein the cells are capable of self-renewal and expansion in culture and have the potential to differentiate into cells of at least a neural phenotype; wherein the cells require L-valine for growth and can grow in at least about 5% oxygen; wherein the cells further comprise at least one of the following characteristics: (a) potential for at least about 40 doublings in culture; (b) attachment and expansion on a coated or uncoated tissue culture vessel, wherein the coated tissue culture vessel comprises a coating of gelatin, laminin, collagen, polyornithine, vitronectin, or fibronectin; (c) production of at least one of tissue factor, vimentin, and alpha-smooth muscle actin; (d) production of at least one of CD10, CD13, CD44, CD73, CD90, PDGFr-alpha, PD-L2 and HLA-A,B,C; (e) lack of production of at least one of CD31, CD34, CD45, CD80, CD86, CD117, CD141, CD178, B7-H2, HLA-G, and HLA-DR,DP,DQ, as detected by flow cytometry; (f) expression of a gene, which relative to a human cell that is a fibroblast, a mesenchymal stem cell, or an iliac crest bone marrow cell, is increased for at least one of a gene encoding: interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; downregulated in ovarian cancer 1; and *Homo sapiens* gene from clone DKFZp547k1113; (g) expression of a gene, which relative to a human cell that is a fibroblast, a mesenchymal stem cell, or an iliac crest bone marrow cell, is reduced for at least one of a gene encoding: short stature homeo box 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; cytochrome c oxidase subunit VIIa polypeptide 1 (muscle); similar to neuralin 1; B cell translocation gene 1; hypothetical protein FLJ23191; and DKFZp586L151; (h) secretion of at least one of MCP-1, IL-6, IL-8, GCP-2, HGF, KGF, FGF, HB-EGF, BDNF, TPO, MIP1a, RANTES, and TIMP1; and (i) lack of secretion of at least one of TGF-beta2, ANG2, PDGFbb, MIP1b, I309, MDC, and VEGF, as detected by ELISA.

In one embodiment, the acute neurodegenerative condition results from ischemic stroke, while in another embodiment, it results from hemorrhagic stroke.

In certain embodiments, the cells are induced in vitro to differentiate into a neural lineage cells prior to administration. In other embodiments, the cells are genetically engineered to produce a gene product that promotes treatment of the neurodegenerative condition.

In certain embodiments, the cells are administered with at least one other cell type, which may include an astrocyte, oligodendrocyte, neuron, neural progenitor, neural stem cell, genetically engineered cell, or other multipotent or pluripotent stem cell. The other cell type can be administered simultaneously with, or before, or after, the postpartum-derived cells. In other embodiments, the cells are administered with at least one other agent, which can be administered simultaneously with, or before, or after, the postpartum-derived cells.

In one embodiment, the cells are administered at a predetermined site in the central or peripheral nervous system of the patient, where they may exert one or more effects, including trophic effects on the nervous system of the patient.

The cells may be administered by injection or infusion, or they can be encapsulated within an implantable device, or they may be administered by implantation of a matrix or scaffold containing the cells.

Another aspect of the invention features a pharmaceutical composition for treating a patient having an acute neurodegenerative condition, comprising a pharmaceutically acceptable carrier and the above-described postpartum-derived cells. In certain embodiments, the composition is used to treat an acute neurodegenerative condition results from ischemic or hemorrhagic stroke.

The cells may be induced in vitro to differentiate into a neural lineage cells prior to formulation of the composition, or they may be genetically engineered to produce a gene product that promotes treatment of the neurodegenerative condition.

In certain embodiments, the pharmaceutical composition contains at least one other cell type, which may an astrocyte, oligodendrocyte, neuron, neural progenitor, neural stem cell, genetically engineered cell, or other multipotent or pluripotent stem cell. In other embodiments, the pharmaceutical composition contains at least one other agent.

The pharmaceutical composition may be formulated for administration by injection or infusion, or encapsulated within an implantable device, or contained within a matrix or scaffold.

Another aspect of the invention features a method of treating a patient having an acute neurodegenerative condition, which comprises administering to the patient a preparation made from the above-described postpartum-derived cells, in an amount effective to treat the neurodegenerative condition, wherein the preparation comprises a cell lysate of the postpartum-derived cells, an extracellular matrix of the postpartum-derived cells, or a conditioned medium in which the postpartum-derived cells were grown.

Yet another aspect of the invention features a pharmaceutical composition for treating a patient having an acute neurodegenerative condition, which comprises a pharmaceutically acceptable carrier and the above-described preparation containing a cell lysate of the postpartum-derived cells, an extracellular matrix of the postpartum-derived cells or a conditioned medium in which the postpartum-derived cells were grown.

Another aspect of the invention features a method of treating stroke in a patient in need thereof comprising administering to the patient a therapeutically effective amount of a cell preparation wherein the cell preparation comprises isolated postpartum-derived cell comprising a cell derived from human placental or umbilical cord tissue, as described above. In one embodiment, the cells are induced in vitro to differentiate into a neural lineage cells prior to administration to the patient. In another embodiment, the cells are genetically engineered to produce a gene product that promotes treatment of stroke. In various embodiments, the cell preparation further comprises at least one other cell type, such as an astrocyte, oligodendrocyte, neuron, neural progenitor, neural stem cell or other multipotent or pluripotent stem cell, or it further comprises at least one other agent for treatment of stroke.

In one embodiment, the cell preparation comprises unfractionated cell lysate, while in another embodiment it comprises a membrane-free cell lysate. In other embodiments, the cell preparation comprises an extracellular matrix of the postpartum-derived cells or a conditioned medium in which the postpartum-derived cells were grown. The cell preparation may be formulated for administration by injection or infusion, or it may be encapsulated within an implantable device or contained within a matrix or scaffold.

Other features and advantages of the invention will be understood by reference to the drawings, detailed description and examples that follow.

DETAILED DESCRIPTION OF ILLUSTRATIVE EMBODIMENTS

Definitions

Figure 1:
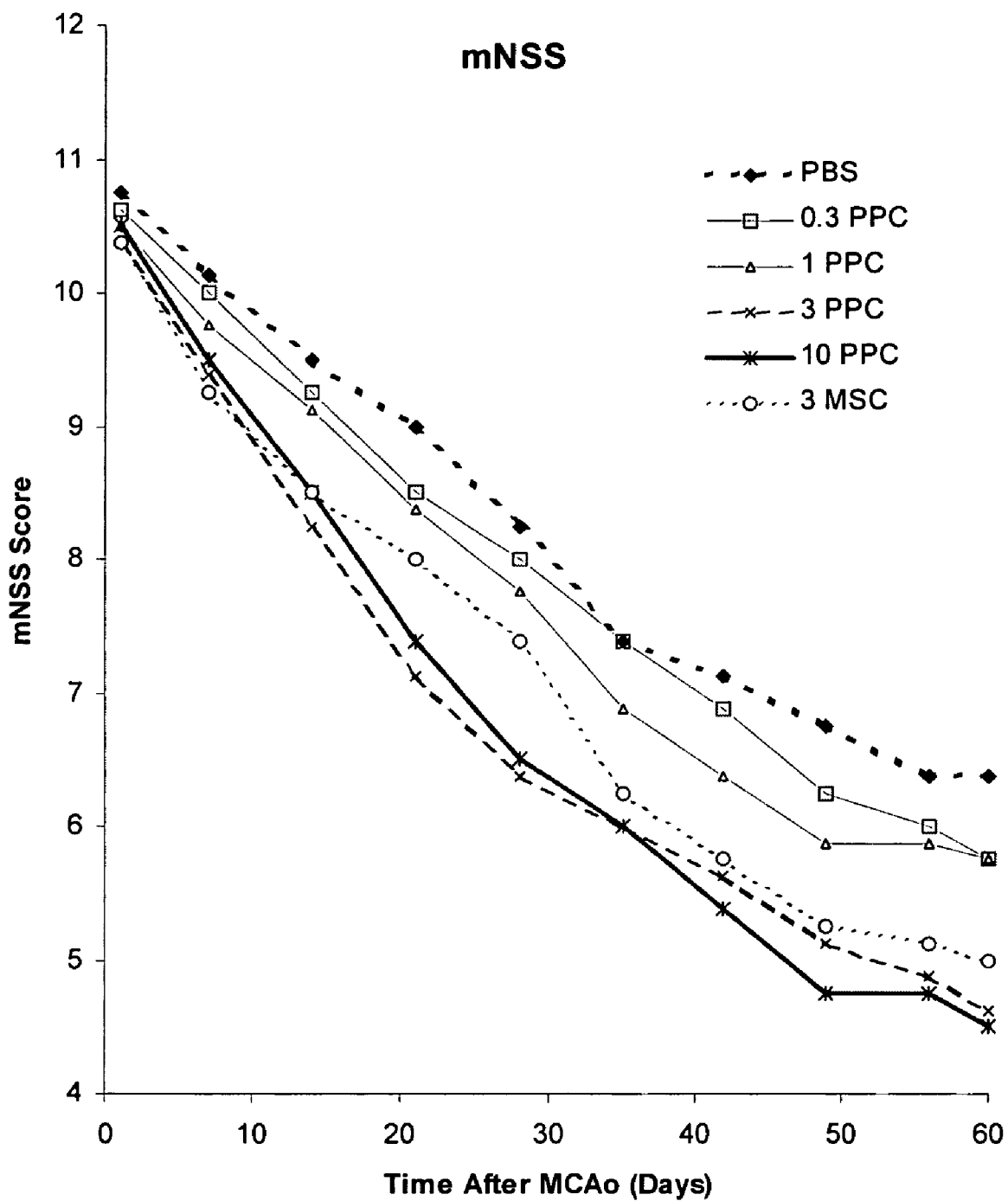
FIG. 1. Graph showing results of Modified Neurological Severity Score (mNSS) Test following middle cerebral artery occlusion (MCAo) in rats (PPC=postpartum-derived cells; MSC=mesenchymal stem cells).

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

The cells of the present invention are generally referred to as postpartum cells or postpartum-derived cells (PPDCs). They also may sometimes be referred to more specifically as umbilicus-derived cells (UDCs) or placenta-derived cells (PDCs). In addition, the cells may be described as being stem or progenitor cells, the latter term being used in the broad sense. The term derived is used to indicate that the cells have been obtained from their biological source and grown or otherwise manipulated in vitro (e.g., cultured in a Growth Medium to expand the population and/or to produce a cell line). The in vitro manipulations of umbilical stem cells and the unique features of the umbilicus-derived cells of the present invention are described in detail below.

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a Growth Medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Growth Medium generally refers to a medium sufficient for the culturing of PPDCs. In particular, one presently preferred medium for the culturing of the cells of the invention in comprises Dulbecco's Modified Eagle Media (also known as Dulbecco's Minimal Essential Media)(DMEM). Particularly preferred is DMEM-low glucose (also DMEM-LG herein) (Invitrogen, Carlsbad, Calif.). The DMEM-low glucose is preferably supplemented with 15% (v/v) fetal bovine serum (e.g., defined fetal bovine serum, Hyclone, Logan Utah), antibiotics and antimycotics (preferably, 50-100 Units/milliliter penicillin, 50-100 microgram/milliliter streptomycin, and 0-0.25 microgram/milliliter amphotericin B; Invitrogen, Carlsbad, Calif.), and 0.001% (v/v) 2-mercaptoethanol (Sigma, St. Louis Mo.).

The term standard growth conditions refers to culturing of cells at 37° C., in a standard humidified atmosphere comprising 5% $CO_2$. While such conditions are useful for culturing, it is to be understood that such conditions are capable of being varied by the skilled artisan who will appreciate the options available in the art for culturing cells.

Generally, a trophic factor is defined as a substance that promotes survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

The term neurodegenerative condition (or disorder) is an inclusive term encompassing acute and chronic conditions, disorders or diseases of the central or peripheral nervous system. A neurodegenerative condition may be age-related, or it may result from injury or trauma, or it may be related to a specific disease or disorder. Acute neurodegenerative conditions include, but are not limited to, conditions associated with neuronal cell death or compromise including cerebrovascular insufficiency, e.g., due to stroke, focal or diffuse brain trauma, diffuse brain damage, spinal cord injury or peripheral nerve trauma, e.g., resulting from physical or chemical burns, deep cuts or limb severance. Examples of acute neurodegenerative disorders are: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), as well as whiplash and shaken infant syndrome. Chronic neurodegenerative conditions include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Sträussler-Scheinker disease, Kuru and fatal familial insomnia), demyelination diseases and disorders including multiple sclerosis and hereditary diseases such as leukodystrophies.

The term stroke refers to any condition arising from a disruption, decrease, or stoppage of blood or oxygen flow to any part of the brain. "Ischemic stroke" refers to a stroke resulting from any disruption, decrease or stoppage in the blood supply to any part of the brain caused from any constriction or obstruction of the vasculature. The obstruction of vasculature may be either temporal or permanent. "Hemorrhagic stroke" refers a stroke resulting from any rupture in any of the vasculature of the brain. Examples of acute neurodegenerative disorders that include stroke or involve etiology or symptoms such as those observed with stroke are listed above, and include: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), as well as whiplash and shaken infant syndrome.

Other neurodegenerative conditions include tumors and other neoplastic conditions affecting the CNS and PNS. Though the underlying disease is considered proliferative (rather than neurodegenerative), surrounding tissues may be compromised. Furthermore, cell therapy may be utilized to deliver apoptotic or other antineoplastic molecules to the tumor site, e.g., via delivery of genetically modified cells producing such agents.

Other neurodegenerative conditions include various neuropathies, such as multifocal neuropathies, sensory neuropathies, motor neuropathies, sensory-motor neuropathies, infection-related neuropathies, autonomic neuropathies, sensory-autonomic neuropathies, demyelinating neuropathies (including, but not limited to, Guillain-Barre syndrome and chronic inflammatory demyelinating polyradiculoneuropathy), other inflammatory and immune neuropathies, neuropathies induced by drugs, neuropathies induced by pharmacological treatments, neuropathies induced by toxins, traumatic neuropathies (including, but not limited to, compression, crush, laceration and segmentation neuropathies), metabolic neuropathies, endocrine and paraneoplastic neuropathies, among others.

Other neurodegenerative conditions include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia.

The term treating (or treatment of) a neurodegenerative condition refers to ameliorating the effects of, or delaying, halting or reversing the progress of, or delaying or preventing the onset of, a neurodegenerative condition as defined herein.

The term effective amount refers to a concentration or amount of a compound, material, or composition, as described herein that is effective to achieve a particular biological result. Such results include, but are not limited to, the regeneration, repair, or improvement of neural tissue, and/or the improvement of behavior and neurological function in stroke patients. Such effective activity may be achieved, for example, by administering the cells and/or compositions of the present invention to a stroke patient. With respect to PPDCs as administered to a patient in vivo, an effective amount may range from as few as several hundred or fewer to as many as several million or more. In specific embodiments, an effective amount may range from $10^3$-$10^{11}$, more specifically at least about $10^4$ cells. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the skilled artisan.

The terms effective period (or time) and effective conditions refer to a period of time or other controllable conditions (e.g., temperature, humidity for in vitro methods), necessary or preferred for an agent or pharmaceutical composition to achieve its intended result.

The terms patient or subject are used interchangeably herein, and refer to animals, preferably mammals, and more preferably humans, who are treated with the pharmaceutical or therapeutic compositions or in accordance with the methods described herein.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Several terms are used herein with respect to cell or tissue transplantation. The terms autologous transfer, autologous transplantation, autograft and the like refer to transplantation wherein the transplant donor is also the transplant recipient. The terms allogeneic transfer, allogeneic transplantation, allograft and the like refer to transplantation wherein the transplant donor is of the same species as the transplant recipient, but is not the same individual. A cell transplant in which the donor's cells and have been histocompatibility matched with a recipient is sometimes referred to as a syngeneic transfer. The terms xenogeneic transfer, xenogeneic transplantation, xenograft and the like refer to transplantation wherein the transplant donor is of a different species than the transplant recipient.

Description:

Neurodegenerative conditions, which encompass acute, chronic and progressive disorders and diseases having widely divergent causes, have as a common feature the dysfunction or loss of a specific or vulnerable group of neural cells. This commonality enables development of similar therapeutic approaches for the repair and regeneration of vulnerable or damaged neural tissue, one of which is cell-based therapy. In its various embodiments described herein, the present invention features methods and pharmaceutical compositions for neural repair and regeneration that utilize progenitor cells and cell populations derived from postpartum tissues. The invention is applicable to any neurodegenerative condition, but is expected to be particularly suitable for the treatment of strokes.

As summarized above, the invention, in one of its aspects is generally directed to isolated postpartum-derived cells (PPDCs), which are derived from placental or umbilical cord tissue that has been rendered substantially free of blood. The PPDCs are capable of self-renewal and expansion in culture and have the potential to differentiate into cells of neural phenotypes. Certain embodiments features populations comprising such cells, pharmaceutical compositions comprising the cells or components or products thereof, and methods of using the pharmaceutical compositions for treatment of stroke patients. The postpartum-derived cells have been characterized by their growth properties in culture, by their cell surface markers, by their gene expression, by their ability to produce certain biochemical trophic factors, and by their immunological properties.

Preparation of PPDCs

According to the methods described herein, a mammalian placenta and umbilical cord are recovered upon or shortly after termination of either a full-term or pre-term pregnancy, for example, after expulsion after birth. The postpartum tissue may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM)(also known as Dulbecco's Minimal Essential Medium) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of PPDCs. It is even more preferable that the tissue not be frozen prior to extraction of PPDCs.

Isolation of PPDCs preferably occurs in an aseptic environment. The umbilical cord may be separated from the placenta by means known in the art. Alternatively, the umbilical cord and placenta are used without separation. Blood and debris are preferably removed from the postpartum tissue prior to isolation of PPDCs. For example, the postpartum tissue may be washed with buffer solution, such as but not limited to phosphate buffered saline. The wash buffer also may comprise one or more antimycotic and/or antibiotic agents, such as but not limited to penicillin, streptomycin, amphotericin B, gentamicin, and nystatin.

Postpartum tissue comprising a whole placenta or a fragment or section thereof is disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Ranging from weakly digestive (e.g. deoxyribonucleases and the neutral protease, dispase) to strongly digestive (e.g. papain and trypsin), such enzymes are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE Blendzyme (Roche) series of enzyme combinations are suitable for use in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, postpartum tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome.

Isolated cells or postpartum tissue from which PPDCs grow out may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. PPDCs are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, and CELL-GRO-FREE. The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth Medium as defined in the Examples below.

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25 to about 40° C. and more preferably are cultured at 37° C. The cells are preferably cultured in an incubator. The medium in the culture vessel can be static or agitated, for example, using a bioreactor. PPDCs preferably are grown under low oxidative stress (e.g., with addition of glutathione, Vitamin C, Catalase, Vitamin E, N-Acetylcysteine). "Low oxidative stress," as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

After culturing the isolated cells or tissue fragments for a sufficient period of time, PPDCs will have grown out, either as a result of migration from the postpartum tissue or cell division, or both. In some embodiments of the invention, PPDCs are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in postpartum tissue are fractionated into subpopulations from which the PPDCs can be isolated. This may be accomplished using standard techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS). For a review of clonal selection and cell separation techniques, see Freshney, 1994, CULTURE OF ANIMAL CELLS: A MANUAL OF BASIC TECHNIQUES, 3rd Ed., Wiley-Liss, Inc., New York, which is incorporated herein by reference.

The culture medium is changed as necessary, for example, by carefully aspirating the medium from the dish, for example, with a pipette, and replenishing with fresh medium. Incubation is continued until a sufficient number or density of cells accumulate in the dish. The original explanted tissue sections may be removed and the remaining cells trypsinized using standard techniques or using a cell scraper or non-enzmatic means of cell removal such as solutions containing chelators or on cell culture dishes coated with polymers allowing easy detachment. After trypsinization, the cells are collected, removed to fresh medium and incubated as above. In some embodiments, the medium is changed at least once at approximately 24 hours post-trypsinization to remove any floating cells. The cells remaining in culture are considered to be PPDCs.

PPDCs may be cryopreserved. Accordingly, in a preferred embodiment described in greater detail below, PPDCs for autologous transfer (for either the mother or child) may be derived from appropriate postpartum tissues following the birth of a child, then cryopreserved so as to be available in the event they are later needed for transplantation.

Characteristics of PPDCs

PPDCs may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of PPDCs derived from placental tissue were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079. Examples of PPDCs derived from umbilicus tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the PPDCs possess one or more of the following growth features (1) they require L-valine for growth in culture; (2) they are capable of growth in atmospheres containing oxygen from about 5% to at least about 20% (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyornithine, vitronectin or fibronectin.

In certain embodiments the PPDCs possess a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the PPDCs may be characterized by production of certain proteins, including (1) production of at least one of tissue factor, vimentin, and alpha-smooth muscle actin; and (2) production of at least one of CD10, CD13, CD44, CD73, CD90, PDGFr-alpha, PD-L2 and HLA-A,B,C cell surface markers, as detected by flow cytometry. In other embodiments, the PPDCs may be characterized by lack of production of at least one of CD31, CD34, CD45, CD80, CD86, CD117, CD141, CD178, B7-H2, HLA-G, and HLA-DR,DP,DQ cell surface markers, as detected by flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the PPDCs may be characterized by gene expression, which relative to a human cell that is a fibroblast, a mesenchymal stem cell, or an iliac crest bone marrow cell, is increased for a gene encoding at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; downregulated in ovarian cancer 1; and *Homo sapiens* gene from clone DKFZp547k1113.

In yet other embodiments, the PPDCs may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the PPDCs may be characterized by secretion of at least one of MCP-1, IL-6, IL-8, GCP-2, HGF, KGF, FGF, HB-EGF, BDNF, TPO, MIP1 alpha, RANTES, and TIMP1. In alternative embodiments, the PPDCs may be characterized by lack of secretion of at least one of TGF-beta2, ANG2, PDGFbb, MIP1 beta, I309, MDC, and VEGF, as detected by ELISA.

In preferred embodiments, the cell comprises two or more of the above-listed growth, protein/surface marker production, gene expression or substance-secretion characteristics. More preferred are those cells comprising, three, four, or five or more of the characteristics. Still more preferred are PPDCs comprising six, seven, or eight or more of the characteristics. Still more preferred presently are those cells comprising all of above characteristics.

Among cells that are presently preferred for use with the invention in several of its aspects are postpartum cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by flow cytometry.

Certain cells having the potential to differentiate along lines leading to various phenotypes are unstable and thus can spontaneously differentiate. Presently preferred for use with the invention are cells that do not spontaneously differentiate, for example along neural lines. Preferred cells, when grown in Growth Medium, are substantially stable with respect to the cell markers produced on their surface, and with respect to the expression pattern of various genes, for example as determined using an Affymetrix GENECHIP. The cells remain substantially constant, for example in their surface marker characteristics over passaging, through multiple population doublings.

However, one feature of PPDCs is that they may be deliberately induced to differentiate into neural lineage phenotypes by subjecting them to differentiation-inducing cell culture conditions. This may be accomplished by one or more methods known in the art. For instance, as exemplified herein, PPDCs may be plated on flasks coated with laminin in Neurobasal-A medium (Invitrogen, Carlsbad, Calif.) containing B27 (B27 supplement, Invitrogen), L-glutamine and Penicillin/Streptomycin, the combination of which is referred to herein as Neural Progenitor Expansion (NPE) medium. NPE media may be further supplemented with bFGF and/or EGF. Alternatively, PPDCs may be induced to differentiate in vitro by (1) co-culturing the PPDCs with neural progenitor cells, or astrocytes, or (2) growing the PPDCs in neural progenitor cell-conditioned medium.

Differentiation of the PPDCs may be demonstrated by a bipolar cell morphology with extended processes. The induced cell populations may stain positive for the presence of nestin. Differentiated PPDCs may be assessed by detection of nestin, TuJ1 (BetaIII tubulin), GFAP, tyrosine hydroxylase, GABA, O4 and/or MBP. In some embodiments, PPDCs have exhibited the ability to form three-dimensional bodies characteristic of neuronal stem cell formation of neurospheres.

PPDC Populations, Modifications, Components and Products

Another aspect of the invention features populations of the PPDCs described above. In some embodiments, the cell population is heterogeneous. heterogeneous cell population of the invention may comprise at least about 5%, 10%, 20%, 30%, 40%, 50%, 60%, 70%, 80%, 90%, or 95% PPDCs of the invention. The heterogeneous cell populations of the invention may further comprise stem cells or other progenitor cells, such as neural progenitor cells, or it may further comprise fully differentiated neural cells. In some embodiments, the population is substantially homogeneous, i.e., comprises substantially only PPDCs (preferably at least about 96%, 97%, 98%, 99% or more PPDCs). The homogeneous cell population of the invention may comprise umbilicus- or placenta-derived cells. Homogeneous populations of umbilicus-derived cells are preferably free of cells of maternal lineage. Homogeneous populations of placenta-derived cells may be of neonatal or maternal lineage. Homogeneity of a cell population may be achieved by any method known in the art, for example, by cell sorting (e.g., flow cytometry) or by clonal expansion in accordance with known methods. Thus, preferred homogeneous PPDC populations may comprise a clonal cell line of postpartum-derived cells. Such populations are particularly useful when a cell clone with highly desirable functionality has been isolated.

Also provided herein are populations of cells incubated in the presence of one or more factors, or under conditions, that stimulate stem cell differentiation along a neurogenic pathway. Such factors are known in the art and the skilled artisan will appreciate that determination of suitable conditions for differentiation can be accomplished with routine experimentation. Optimization of such conditions can be accomplished by statistical experimental design and analysis, for example response surface methodology allows simultaneous optimization of multiple variables, for example in a biological culture. Presently preferred factors include, but are not limited to factors, such as growth or trophic factors, demethylating agents, co-culture with neural lineage cells or culture in neural lineage cell-conditioned medium, as well other conditions known in the art to stimulate stem cell differentiation along a neurogenic pathway or lineage (see, e.g., Lang, K J D et al., 2004, *J. Neurosci. Res.* 76:184-192; Johe, K K et al., (1996) *Genes Devel.* 10:3129-3140; Gottleib, D., (2002) *Ann. Rev. Neurosci.* 25:381-407).

PPDCs may also be genetically modified to produce neurotherapeutically useful gene products, or to produce antineoplastic agents for treatment of tumors, for example. Genetic modification may be accomplished using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Cells are preferably transformed or transfected with DNA controlled by or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV 40, papillomavirus, Epstein-Barr virus or elastin gene promoter. In some embodiments, the control elements used to control expression of the gene of interest can allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a neuron or glial cell can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, Proc. Nat. Acad. Sci. U.S.A. 88:3084-3087). Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, Basic Methods in Molecular Biology, 2nd ed., Appleton & Lange, Norwalk, Conn.

In other aspects, the invention provides cell derivatives and cell soluble fractions prepared from PPDCs, or heterogeneous or homogeneous cell populations comprising PPDCs, as well as PPDCs or populations thereof that have been genetically modified or that have been stimulated to differentiate along a neurogenic pathway. Such cell derivatives such as lysates and fractions thereof have many utilities. Use of the PPDC lysate soluble fraction (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well-known in the art and include various means of mechanical disruption, enzymatic disruption, thermal, or chemical disruption, or combinations thereof. Such cell lysates may be prepared from cells directly in their Growth Medium and thus containing secreted growth factors and the like, or may be prepared from cells washed free of medium in, for example, PBS or other solution. Washed cells may be resuspended at concentrations greater than the original population density if preferred.

In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods.

Cell lysates or cell soluble fractions prepared from populations of postpartum-derived cells may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Cell lysates or fractions thereof may be used in vitro or in vivo, alone or for example, with autologous or syngeneic live cells. The lysates, if introduced in vivo, may be introduced locally at a site of treatment, or remotely to provide, for example needed cellular growth factors to a patient.

In a further embodiment, PPDCs can be cultured in vitro to produce biological products in high yield. For example, such cells, which either naturally produce a particular biological product of interest (e.g., a trophic factor), or have been genetically engineered to produce a biological product, can be clonally expanded using the culture techniques described herein. Alternatively, cells may be expanded in a medium that induces differentiation to a neural lineage. In either case, biological products produced by the cell and secreted into the medium can be readily isolated from the conditioned medium using standard separation techniques, e.g., such as differential protein precipitation, ion-exchange chromatography, gel filtration chromatography, electrophoresis, and HPLC, to name a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed, as described above. The biological product may then be purified using any one or more of the above-listed techniques.

In other embodiments, the invention provides conditioned medium from cultured PPDCs for use in vitro and in vivo as described below. Use of the PPDC conditioned medium allows the beneficial trophic factors secreted by the PPDCs to be used allogeneically in a patient without introducing intact cells that could trigger rejection, or other adverse immunological responses. Conditioned medium is prepared by culturing cells in a culture medium, then removing the cells from the medium.

Conditioned medium prepared from populations of postpartum-derived cells may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Conditioned medium may be used in vitro or in vivo, alone or for example, with autologous or syngeneic live cells. The conditioned medium, if introduced in vivo, may be introduced locally at a site of treatment, or remotely to provide, for example needed cellular growth or trophic factors to a patient.

In another embodiment, an extracellular matrix (ECM) produced by culturing PPDCs on liquid, solid or semi-solid substrates is prepared, collected and utilized as an alternative to implanting live cells into a subject in need of tissue repair or replacement. PPDCs are cultured in vitro, on a three dimensional framework as described elsewhere herein, under conditions such that a desired amount of ECM is secreted onto the framework. The comprising the new tissue are removed, and the ECM processed for further use, for example, as an injectable preparation. To accomplish this, cells on the framework are killed and any cellular debris removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure.

Once the cells have been killed, the cellular membranes may be disrupted and cellular debris removed by treatment with a mild detergent rinse, such as EDTA, CHAPS or a zwitterionic detergent. Alternatively, the tissue can be enzymatically digested and/or extracted with reagents that break down cellular membranes and allow removal of cell contents. Example of such enzymes include, but are not limited to, hyaluronidase, dispase, proteases, and nucleases. Examples of detergents include non-ionic detergents such as, for example, alkylaryl polyether alcohol (TRITON X-100), octylphenoxy polyethoxy-ethanol (Rohin and Haas Philadelphia, Pa.), BRIJ-35, a polyethoxyethanol lauryl ether (Atlas Chemical Co., San Diego, Calif.), polysorbate 20 (TWEEN 20), a polyethoxyethanol sorbitan monolaureate (Rohm and Haas), polyethylene lauryl ether (Rohm and Haas); and ionic detergents such as, for example, sodium dodecyl sulfate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending, for example, on whether the new tissue has been formed on a three-dimensional framework that is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM. A non-biodegradable framework can be implanted with the cells.

After it has been collected, the ECM may be processed further. For example, the ECM can be homogenized to fine particles using techniques well known in the art such as by sonication, so that it can pass through a surgical needle. The components of the ECM can be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

The amounts and/or ratios of proteins, such as the various types of collagen present in the ECM, may be adjusted by mixing the ECM produced by the cells of the invention with ECM of one or more other cell types. In addition, biologically active substances such as proteins, growth factors and/or drugs, can be incorporated into the ECM. Exemplary biologically active substances include BDNF, which promotes neu-ral survival and protection at the site of the injection. Such additional agents may be utilized in any of the embodiments described herein above, e.g., with whole cell lysates, soluble cell fractions, or further purified components and products produced by the PPDCs.

Pharmaceutical Compositions Comprising PPDCs, PPDC Derivative Components or Products In another aspect, the invention provides pharmaceutical compositions that utilize the PPDCs, PPDC populations, components and products of PPDCs in various methods for treatment of strokes. Certain embodiments encompass pharmaceutical compositions comprising live cells (PPDCs alone or admixed with other cell types). Other embodiments encompass pharmaceutical compositions comprising PPDC cellular components (e.g., cell lysates, soluble cell fractions, conditioned medium, ECM, or components of any of the foregoing) or products (e.g., trophic and other biological factors produced naturally by PPDCs or through genetic modification, conditioned medium from PPDC culture). In either case, the pharmaceutical composition may further comprise other active agents, such as anti-inflammatory agents, anti-apoptotic agents, antioxidants, growth factors, neurotrophic factors, pro-angiogenic factors, or neuroregenerative or neuroprotective drugs as known in the art.

Examples of other components that may be added to PPDC pharmaceutical compositions include, but are not limited to: (1) other neuroprotective or neurobeneficial drugs; (2) selected extracellular matrix components, such as one or more types of collagen known in the art, and/or growth factors, platelet-rich plasma, and drugs (alternatively, PPDCs may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPOXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; (6) local anesthetics; and (7) neurotrophic factors such as GDF5, BMP-14, CDMP-1, MP52, BMP7, Sonic Hedgehog (SHH), Fibroblast Growth Factor 8 (FGF8), BDNF, NGF, and CNTF, to name a few.

Pharmaceutical compositions of the invention comprise PPDCs, or components or products thereof, formulated with a pharmaceutically acceptable carrier or medium. Suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences ($17^{th}$ Ed., Mack Pub. Co., Easton, Pa.) and WO 96/05309.

Typically, but not exclusively, pharmaceutical compositions comprising PPDC components or products, but not live cells, are formulated as liquids (or as solid tablets, capsules and the like, when oral delivery is appropriate). These may be formulated for administration by any acceptable route known in the art to achieve delivery of drugs and biological molecules to the target neural tissue, including, but not limited to, oral, nasal, ophthalmic and parenteral, including intravenous. Particular routes of parenteral administration include, but are not limited to, intramuscular, subcutaneous, intraperitoneal, intracerebral, intraventricular, intracerebroventricular, intrathecal, intracisternal, epidural, intra-arterial, intrasternal, intra-synovial, intra-articular, intraspinal and/or peri-spinal routes of administration by delivery via intracranial or intravertebral needles and/or catheters with or without pump devices.

Pharmaceutical compositions comprising PPDC live cells are typically formulated as liquids, semisolids (e.g., gels) or solids (e.g., matrices, scaffolds and the like, as appropriate for neural tissue engineering). Liquid compositions are formulated for administration by any acceptable route known in the art to achieve delivery of live cells to the target neural tissues. Typically, these include injection or infusion into the CNS or PNS, either in a diffuse fashion or targeted to the site of neurological disease or distress, by a route of administration including, but not limited to, intraocular, intracerebral, intraventricular, intracerebroventricular, intrathecal, intracisternal, intraspinal and/or peri-spinal routes of administration by delivery via intracranial or intravertebral needles and/or catheters with or without pump devices. When injected or infused, the cells may migrate to the site of the injury.

Pharmaceutical compositions comprising live cells in a semi-solid or solid carrier are typically formulated for surgical implantation at the site of neurological damage or distress. It will be appreciated that liquid compositions also may be administered by surgical procedures. In particular embodiments, semi-solid or solid pharmaceutical compositions may comprise semi-permeable gels, lattices, cellular scaffolds and the like, which may be non-biodegradable or biodegradable. For example, in certain embodiments, it may be desirable or appropriate to sequester the exogenous cells from their surroundings, yet enable the cells to secrete and deliver biological molecules (e.g. neurotrophic factors) to surrounding neural cells. In these embodiments, cells may be formulated as autonomous implants comprising living PPDCs or cell population comprising PPDCs surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression (for a review of such devices and methods, see, e.g., P. A. Tresco et al., (2000) Adv. Drug Delivery Rev. 42:3-27).

In other embodiments, different varieties of degradable gels and networks are utilized for the pharmaceutical compositions of the invention. For example, degradable materials particularly suitable for sustained release formulations include biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., 1992, Polymers for Advanced Technologies 3:279-292.

In other embodiments, e.g. for repair of large neural lesions, such as a damaged or severed spinal cord or a neural cord of a severed limb, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established (see, e.g., Tresco, Pa., et al. (2000) supra; see also Hutmacher, D W (2001) J. Biomater. Sci. Polymer Edn. 12:107-174).

The biocompatible matrix may be comprised of natural, modified natural or synthetic biodegradable polymers, including homopolymers, copolymers and block polymers, as well as combinations thereof. It is noted that a polymer is generally named based on the monomer from which it is synthesized.

Examples of suitable biodegradable polymers or polymer classes include fibrin, collagen, elastin, gelatin, vitronectin, fibronectin, laminin, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. For both glycolic acid and lactic acid, an intermediate cyclic dimer is typically prepared and purified prior to polymerization. These intermediate dimers are called glycolide and lactide, respectively. Other useful biodegradable polymers or polymer classes include, without limitation, polydioxanones, polycarbonates, polyoxalates, poly(alpha-esters), polyanhydrides, polyacetates, polycaprolactones, poly(orthoesters), polyamino acids, polyamides and mixtures and copolymers thereof. Additional useful biodegradable polymers include, without limitation stereopolymers of L- and D-lactic acid, copolymers of bis(para-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, polyhydroxy-alkanoates and mixtures thereof. Binary and ternary systems also are contemplated.

In general, a suitable biodegradable polymer for use as the matrix is desirably configured so that it has mechanical properties that are suitable for the intended application, remains sufficiently intact until tissue has in-grown and healed, does not invoke an inflammatory or toxic response, is metabolized in the body after fulfilling its purpose, is easily processed into the desired final product to be formed, demonstrates acceptable shelf-life, and is easily sterilized.

In one aspect of the invention, the biocompatible polymer used to form the matrix is in the form of a hydrogel. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic, or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, as those discussed in U.S. Pat. Nos. 5,670,483 and 5,955,343, U.S. Patent Application No. 2002/0160471, PCT Application No. WO02/062969.

Properties that make hydrogels valuable in drug delivery applications include the equilibrium swelling degree, sorption kinetics, solute permeability, and their in vivo performance characteristics. Permeability to compounds depends in part upon the swelling degree or water content and the rate of biodegradation. Since the mechanical strength of a gel declines in direct proportion to the swelling degree, it is also well within the contemplation of the present invention that the hydrogel can be attached to a substrate so that the composite system enhances mechanical strength. In alternative embodiments, the hydrogel can be impregnated within a porous substrate, so as to gain the mechanical strength of the substrate, along with the useful delivery properties of the hydrogel.

Non-limiting examples of scaffold or matrix (sometimes referred to collectively as "framework") material that may be used in the present invention include nonwoven mats, particulate systems, porous foams, or hydrogels such as self assembling peptides. Nonwoven mats may, for example, be formed using fibers comprised of a synthetic absorbable copolymer of glycolic and lactic acids (PGA/PLA), sold under the tradename VICRYL (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, also may be utilized. Hydrogels such as self-assembling peptides (e.g., RAD16) may also be used. In situ-forming degradable networks are also suitable for use in the invention (see, e.g., Anseth, K S et al. (2002) *J. Controlled Release* 78:199-209; Wang, D. et al., (2003) *Biomaterials* 24:3969-3980; U.S. Patent Publication 2002/0022676 to He et al.). These materials are formulated as fluids suitable for injection, then may be induced by a variety of means (e.g., change in temperature, pH, exposure to light) to form degradable hydrogel networks in situ or in vivo. Particulate systems can be made using supercritical fluid or spinning disk processes, or others known in the art.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures.

In many of the abovementioned embodiments, the framework may be molded into a useful shape, such as that of the spinal cord with segregated columns for nerve tract repair, for example (Friedman, J A et al., (2002) *Neurosurgery* 51:742-751). Furthermore, it will be appreciated that PPDCs may be cultured on pre-formed, non-degradable surgical or implantable devices, e.g., in a manner corresponding to that used for preparing fibroblast-containing GDC endovascular coils, for instance (Marx, W F et al., (2001) *Am. J. Neuroradiol.* 22:323-333).

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

PPDC-containing frameworks are prepared according to methods known in the art. For example, cells can be grown freely in a culture vessel to sub-confluency or confluency, lifted from the culture and inoculated onto the framework. Growth factors may be added to the culture medium prior to, during, or subsequent to inoculation of the cells to trigger differentiation and tissue formation, if desired. Alternatively, the frameworks themselves may be modified so that the growth of cells thereon is enhanced, or so that the risk of rejection of the implant is reduced. Thus, one or more biologically active compounds, including, but not limited to, anti-inflammatories, immunosuppressants or growth factors, may be added to the framework for local release.

Methods of Using PPDCs, PPDC Components or Products

PPDCs, parts of PPDCs, or cell populations comprising PPDCs, or components of or products produced by PPDCs, may be used in a variety of ways to support and facilitate repair and regeneration of neural cells and tissues, and to improve neurological function and behavior. Such utilities encompass in vitro, ex vivo and in vivo methods.

In Vitro and Ex Vivo Methods:

In one embodiment, PPDCs may be used in vitro to screen a wide variety of compounds for effectiveness and cytotoxicity of pharmaceutical agents, growth factors, regulatory factors, and the like. For example, such screening may be performed on substantially homogeneous populations of PPDCs to assess the efficacy or toxicity of candidate compounds to be formulated with, or co-administered with, the PPDCs, for treatment of strokes. Alternatively, such screening may be performed on PPDCs that have been stimulated to differentiate into a neural cell or neural progenitor cell, for the purpose of evaluating the efficacy of new pharmaceutical drug candidates. In this embodiment, the PPDCs are maintained in vitro and exposed to the compound to be tested. The activity of a potentially cytotoxic compound can be measured by its ability to damage or kill cells in culture. This may readily be assessed by vital staining techniques. The effect of growth or regulatory factors may be assessed by analyzing the number or robustness of the cultured cells, as compared with cells not exposed to the factors. This may be accomplished using standard cytological and/or histological techniques, including the use of immunocytochemical techniques employing antibodies that define type-specific cellular antigens.

In a further embodiment, as discussed above, PPDCs can be cultured in vitro to produce biological products that are either naturally produced by the cells, or produced by the cells when induced to differentiate into neural lineages, or produced by the cells via genetic modification. For instance, TIMP1, TPO, KGF, HGF, FGF, HBEGF, BDNF, MIP1 beta, MCP1, RANTES, I309, TARC, MDC, and IL-8 were found to be secreted from umbilicus-derived cells grown in Growth Medium. TIMP1, TPO, KGF, HGF, HBEGF, BDNF, MIP1 alpha, MCP-1, RANTES, TARC, Eotaxin, and IL-8 were found to be secreted from placenta-derived PPDCs cultured in Growth Medium (see Examples). Some of these trophic factors, such as BDNF and IL-6, have important roles in neural regeneration. Other trophic factors, as yet undetected or unexamined, of use in neural repair and regeneration, are likely to be produced by PPDCs and possibly secreted into the medium.

In this regard, another embodiment of the invention features use of PPDCs for production of conditioned medium, either from undifferentiated PPDCs or from PPDCs incubated under conditions that stimulate differentiation into a neural lineage. Such conditioned media are contemplated for use in in vitro or ex vivo culture of neurogeneic precursor cells, or in vivo to support transplanted cells comprising homogeneous populations of PPDCs or heterogeneous populations comprising PPDCs and neural progenitors, for example.

Yet another embodiment comprises the use of PPDC cell lysates, soluble cell fractions or components thereof, or ECM or components thereof, for a variety of purposes. As mentioned above, some of these components may be used in pharmaceutical compositions. In other embodiments, a cell lysate or ECM is used to coat or otherwise treat substances or devices to be used surgically, or for implantation, or for ex vivo purposes, to promote healing or survival of cells or tissues contacted in the course of such treatments.

As described in Examples 13 and 15, PPDCs have demonstrated the ability to support survival, growth and differentiation of adult neural progenitor cells when grown in co-culture with those cells. Accordingly, in another embodiment, PPDCs are used advantageously in co-cultures in vitro to provide trophic support to other cells, in particular neural cells and neural progenitors. For co-culture, it may be desirable for the PPDCs and the desired other cells to be co-cultured under conditions in which the two cell types are in contact. This can be achieved, for example, by seeding the cells as a heterogeneous population of cells in culture medium or onto a suitable culture substrate. Alternatively, the PPDCs can first be grown to confluence, and then will serve as a substrate for the second desired cell type in culture. In this latter embodiment, the cells may further be physically separated, e.g., by a membrane or similar device, such that the other cell type may be removed and used separately, following the co-culture period. Use of PPDCs in co-culture to promote expansion and differentiation of neural cell types may find applicability in research and in clinical/therapeutic areas. For instance, PPDC co-culture may be utilized to facilitate growth and differentiation of neural cells in culture, for basic research purposes or for use in drug screening assays, for example. PPDC co-culture may also be utilized for ex vivo expansion of neural progenitors for later administration for therapeutic purposes. For example, neural progenitor cells may be harvested from an individual, expanded ex vivo in co-culture with PPDCs, then returned to that individual (autologous transfer) or another individual (syngeneic or allogeneic transfer). In these embodiments, it will be appreciated that, following ex vivo expansion, the mixed population of cells comprising the PPDCs and neural progenitors could be administered to a patient in need of treatment. Alternatively, in situations where autologous transfer is appropriate or desirable, the co-cultured cell populations may be physically separated in culture, enabling removal of the autologous neural progenitors for administration to the patient.

Alternatively, neuroprogenitor cells or astrocytes could be subjected to an ischemic insult to activate similar pathways to those occurring during stroke. Cells could also be pre-conditioned by incubation in ischemic conditions.

In Vivo Methods:

As set forth in Examples 16-19, PPDCs have been shown to be effectively transplanted into the body, and to supply lost neural function in an animal model accepted for its predictability of efficacy in humans. These results support preferred embodiments of the invention, wherein PPDCs are used in cell therapy for treating strokes by repairing neutral tissue in a stroke patient, wherein PPDCs are used in cell therapy for treating a stroke by regenerating neural tissue in a stroke patient, and wherein PPDCs are used in cell therapy for treating a stroke by improving neurological function or behavior in a stroke patient. In one embodiment, the PPDCs are transplanted into a target neural location in the body, were the PPDCs can differentiate into one or more neural phenotypes, or the PPDCs may provide tropic support for neural progenitors and neural cells in situ, or the PPDCs may exert a beneficial effect in both of those fashions, among others.

Specific embodiments of the invention are directed to support, regeneration or replacement of dopaminergic (DA) neurons and other conditions affecting DA-rich regions of the brain, e.g., strokes affecting the middle cerebral artery (MCA) and its branches. As described in detail in Example 18, PPDCs were shown efficacious in the treatment of rats in which middle cerebral artery occlusion was induced temporally. In the cell efficacy study, statistically significant improvement was observed in behavioral tests; functional recovery was compared to control rats receiving either PBS or mesenchymal stem cells. In addition, transplanted PPDCs were able to home to the site of ischemic injury from a systemic administration via tail vein injection. PPDCs were observed to survive in the rat brain for the duration of the study (28 days). This was accompanied by indicators of neurotrophic benefits, including increased in neurogenesis, angiogenesis and synaptogenesis, as well as a lower incidence of cellular apoptosis and death, in the ischemic rat brain. Such benefits could be the result of PPDCs stimulating host cell migration, proliferation, and neurogenesis. Remarkably the transplantation of human PPDCs into rats did not require usage of immunosuppressants.

PPDCs may be administered alone (e.g., as substantially homogeneous populations) or as admixtures with other cells. As described above, PPDCs may be administered as formulated in a pharmaceutical preparation with a matrix or scaffold, or with conventional pharmaceutically acceptable carriers. The matrix or scaffold can be a GMP manufactured enclosed system that permits material uptake and exchange. Where PPDCs are administered with other cells, they may be administered simultaneously or sequentially with the other cells (either before or after the other cells). Cells that may be administered in conjunction with PPDCs include, but are not limited to, neurons, astrocytes, oligodendrocytes, neural progenitor cells, neural stem cells and/or other multipotent or pluripotent stem cells. The cells of different types may be admixed with the PPDCs immediately or shortly prior to administration, or they may be co-cultured together for a period of time prior to administration. PPDCs may be subjected to short periods of hypoxia prior to administration, to increase their chances of survival and/or production of beneficial factors. The potassium channels of PPDCs can be modulated via one to multiple short bursts of exposure to modulating drugs.

The PPDCs may be administered with other neuro-beneficial drugs or biological molecules, or other active agents, such as anti-inflammatory agents, anti-apoptotic agents, antioxidants, growth factors, neurotrophic factors or neuroregenerative or neuroprotective drugs as known in the art. When PPDCs are administered with other agents, they may be administered together in a single pharmaceutical composition, or in separate pharmaceutical compositions, simultaneously or sequentially with the other agents (either before or after administration of the other agents). The other agents may be a part of a treatment regimen that begins either before transplantation and continuing throughout the course of recovery, or may be initiated at the time of transplantation, or even after transplantation, as a physician of skill in the art deems appropriate.

Examples of other components that may be administered with PPDCs include, but are not limited to: (1) other neuroprotective or neurobeneficial drugs; (2) selected extracellular matrix components, such as one or more types of collagen known in the art, and/or growth factors, platelet-rich plasma, and drugs (alternatively, PPDCs may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPOXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (6) local anesthetics, to name a few.

In one embodiment, PPDCs are administered as undifferentiated cells, i.e., as cultured in Growth Medium. Alternatively, PPDCs may be administered following exposure in culture to conditions that stimulate differentiation toward a desired neural phenotype, e.g., astrocyte, oligodendrocyte or neuron, and more specifically, serotoninergic, dopaminergic, cholinergic, GABA-ergic or glutamatergic neurons (see, e.g., Isacson, O., (2003) *The Lancet (Neurology)* 2:417-424).

The cells of the invention may be surgically implanted, injected, delivered (e.g., by way of a catheter or syringe), or otherwise administered directly or indirectly to the site of neurological damage or distress. Routes of administration of the cells of the invention or compositions thereof include, but are not limited to, intravenous, intramuscular, subcutaneous, intranasal, intracerebral, intraventricular, intracerebroventricular, intrathecal, intracisternal, intraspinal and/or peri-spinal routes of administration by delivery via intracranial or intravertebral needles and/or catheters with or without pump devices.

When cells are administered in semi-solid or solid devices, surgical implantation into a precise location in the body is typically a suitable means of administration. Liquid or fluid pharmaceutical compositions, however, may be administered to a more general location in the CNS or PNS (e.g., throughout a diffusely affected area, such as would be expected for a diffuse ischemic injury), inasmuch as neural progenitor cells have been shown to be capable of extensive migration from a point of entry to the nervous system to a particular location, e.g., by following radial glia or by responding to chemical signals.

The postpartum-derived cells or compositions and/or matrices comprising the postpartum-derived cells may be delivered to the site via a micro catheter, intracatheterization, shunt, cannula, or via a mini-pump. The compositions and/or matrices could also be indirectly delivered to the substantia nigra or striatum via intrathecal delivery, or intracerebroventricularly, or by intranasal administration. The vehicle excipient or carrier can be any of those known to be pharmaceutically acceptable for administration to a patient, particularly locally at the site at which cellular differentiation is to be induced. Examples include liquid media, for example, Dulbeccos Modified Eagle's Medium (DMEM), sterile saline, sterile phosphate buffered saline, Leibovitz's medium (L15, Invitrogen, Carlsbad, Calif.), dextrose in sterile water, and any other physiologically acceptable liquid.

A method of delivery into the damaged region is intrathecally or intracerebroventricularly with, for example, an Ommaya reservoir in accordance with known techniques such as those taught in F. Balis and D. Poplack (1989) *Am. J. Pediatric. Hematol. Oncol.* 11(1):74-86. An even more preferred method of delivery into the damaged region is by direct intraparenchymal injection via a microcatheter.

This migratory ability of neural stem cells has opened a new avenue for treatment of malignant brain tumors, i.e., use of progenitor cells for delivery of therapeutic genes/gene products for the treatment of these migratory tumors. For example, it has been reported that neural stem cells, when implanted into intracranial gliomas in vivo in adult rodents, distribute themselves quickly and extensively through the tumor bed and migrate in juxtaposition to expanding and advancing tumor cells, while continuing to stably express a foreign gene (Aboody, K. et al., (2000) *Proc. Natl. Acad. Sci. USA* 97:12846-12851). PPDCs are also expected to be suitable for this type of use, i.e., PPDCs genetically modified to produce an apoptotic or other antineoplastic agent, e.g., IL-12 (Ehtesham, M. et al., (2002) *Cancer Res.* 62:5657-5663) or tumor necrosis factor-related apoptosis-inducing ligand (Ehtesham, M. et al., (2002) *Cancer Res.* 62:7170-7174) may be injected or otherwise administered to a general site of a malignant tumor (e.g., glioblastoma), whereafter the PPDCs can migrate to the tumor cells for local delivery of the therapeutic agent.

Other embodiments encompass methods of treating a stroke by administering therapeutic compositions comprising a pharmaceutically acceptable carrier and PPDC cellular components (e.g., cell lysates or components thereof) or products (e.g., trophic and other biological factors produced naturally by PPDCs or through genetic modification, conditioned medium from PPDC culture), or PPDC growth medium or products purified from growth medium. Again, these methods may further comprise administering other active agents, such as growth factors, neurotrophic factors or neuroregenerative or neuroprotective drugs as known in the art. In addition, efficacy may be obtained by administering one, or multiple times, from several hours to several days after the initial onset of stroke. Cells may also be administered in a range of doses.

Dosage forms and regimes for administering PPDCs or any of the other therapeutic or pharmaceutical compositions described herein are developed in accordance with good medical practice, taking into account the condition of the individual patient, e.g., nature and extent of the neurological damage from the stroke, age, sex, body weight and general medical condition, and other factors known to medical practitioners. Thus, the effective amount of a pharmaceutical composition to be administered to a patient is determined by these considerations as known in the art.

PPDCs can also be administered concomitantly with other therapeutic regimens such as electrical stimulation to promote cell differentiation or survival.

Because the CNS is a somewhat immunoprivileged tissue, it may not be necessary or desirable to immunosuppress a patient prior to initiation of cell therapy with PPDCs. In addition, as set forth in Example 11, PPDCs have been shown not to stimulate allogeneic PBMCs in a mixed lymphocyte reaction. Accordingly, transplantation with allogeneic, or even xenogeneic, PPDCs may be tolerated in some instances. In some embodiments, the PPDCs themselves provide an immunosuppressive effect, thereby preventing host rejection of the transplanted PPDCs. In such instances, pharmacological immunosuppression during cell therapy may not be necessary.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above, or by custom matching cell and patient immunological profiles. These and other means for reducing or eliminating an immune response to the transplanted cells are known in the art. As an alternative, PPDCs may be genetically modified to reduce their immunogenicity, as mentioned above.

Survival of transplanted PPDCs in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the neural tissue, and examining it visually or through a microscope. Alternatively, cells can be treated with stains that are specific for neural cells or products thereof, e.g., neurotransmitters. Transplanted cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

Functional integration of transplanted PPDCs into neural tissue of a subject can be assessed by examining restoration of the neural function that was damaged or diseased. Such functions include, but are not limited to motor, cognitive, sensory and endocrine functions, in accordance with procedures well known to neurobiologists and physicians.

Kits and Banks Comprising PPDCs, PPDC Components or Products

In another aspect, the invention provides kits that utilize the PPDCs, PPDC populations, components and products of PPDCs in various methods for neural regeneration and repair, and in methods for improving neurological function or behavior as described above. Where used for treatment of strokes, or other scheduled treatment, the kits may include one or more cell populations, including at least PPDCs and a pharmaceutically acceptable carrier (liquid, semi-solid or solid). The kits also optionally may include a means of administering the cells, for example by injection. The kits further may include instructions for use of the cells. Kits prepared for field hospital use, such as for military use may include full-procedure supplies including tissue scaffolds, surgical sutures, and the like, where the cells are to be used in conjunction with repair of acute injuries. Kits for assays and in vitro methods as described herein may contain one or more of (1) PPDCs or components or products of PPDCs, (2) reagents for practicing the in vitro method, (3) other cells or cell populations, as appropriate, and (4) instructions for conducting the in vitro method.

In yet another aspect, the invention also provides for banking of tissues, cells, cellular components and cell populations of the invention. As discussed above, the cells are readily cryopreserved or freeze-dried. The invention therefore provides methods of cryopreserving the cells in a bank, wherein the cells are stored frozen and associated with a complete characterization of the cells based on immunological, biochemical and genetic properties of the cells. The frozen cells can be thawed and expanded or used directly for autologous, syngeneic, or allogeneic therapy, depending on the requirements of the procedure and the needs of the patient. Preferably, the information on each cryopreserved sample is stored in a computer, which is searchable based on the requirements of the surgeon, procedure and patient with suitable matches being made based on the characterization of the cells or populations. Preferably, the cells of the invention are grown and expanded to the desired quantity of cells and therapeutic cell compositions are prepared either separately or as co-cultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a source or donor with a recipient of such cells, for immunological purposes, the bank system makes it easy to match, for example, desirable biochemical or genetic properties of the banked cells to the therapeutic needs. Upon matching of the desired properties with a banked sample, the sample is retrieved and prepare for therapeutic use. Cell lysates, ECM or cellular components prepared as described herein may also be cryopreserved or otherwise preserved (e.g., by lyophilization) and banked in accordance with the present invention.

The following examples describe several aspects of embodiments of the invention in greater detail. These examples are provided to further illustrate, not to limit, aspects of the invention described herein.

The following abbreviations may be used in the specification and examples: PPDC, postpartum cells; UDC, umbilicus-derived cells; PDC, placental-derived cells; ANG2 (or Ang2) for angiopoietin 2; APC for antigen-presenting cells; BDNF for brain-derived neurotrophic factor; bFGF for basic fibroblast growth factor; bid (BID) for "bis in die" (twice per day); CK18 for cytokeratin 18; CNS for central nervous system; CXC ligand 3 for chemokine receptor ligand 3; DMEM for Dulbecco's Minimal Essential Medium; DMEM:lg (or DMEM:Lg, DMEM:LG) for DMEM with low glucose; EDTA for ethylene diamine tetraacetic acid; EGF (or E) for epidermal growth factor; FACS for fluorescent activated cell sorting; FBS for fetal bovine serum; FGF (or F) for fibroblast growth factor; GCP-2 for granulocyte chemotactic protein-2; GFAP for glial fibrillary acidic protein; HB-EGF for heparin-binding epidermal growth factor; HCAEC for Human coronary artery endothelial cells; HGF for hepatocyte growth factor; hMSC for Human mesenchymal stem cells; HNF-1 alpha for hepatocyte-specific transcription factor 1 alpha; HUVEC for Human umbilical vein endothelial cells; I309 for a chemokine and the ligand for the CCR8 receptor; IGF-1 for insulin-like growth factor 1; IL-6 for interleukin-6; IL-8 for interleukin 8; K19 for keratin 19; K8 for keratin 8; KGF for keratinocyte growth factor; LIF for leukemia inhibitory factor; MBP for myelin basic protein; MCP-1 for monocyte chemotactic protein 1; MDC for macrophage-derived chemokine; MIP1 alpha for macrophage inflammatory protein 1 alpha; MIP1 beta for macrophage inflammatory protein 1 beta; MMP for matrix metalloprotease (MMP); MSC for mesenchymal stem cells; NHDF for Normal Human Dermal Fibroblasts; NPE for Neural Progenitor Expansion media; O4 for oligodendrocyte or glial differentiation marker O4; PBMC for Peripheral blood mononuclear cell; PBS for phosphate buffered saline; PDGFbb for platelet derived growth factor; PO for "per os" (by mouth); PNS for peripheral nervous system; Rantes (or RANTES) for regulated on activation, normal T cell expressed and secreted; rhGDF-5 for recombinant human growth and differentiation factor 5; SC for subcutaneously; SDF-1 alpha for stromal-derived factor 1 alpha; SHH for sonic hedgehog; SOP for standard operating procedure; TARC for thymus and activation-regulated chemokine; TCP for Tissue culture plastic; TCPS for tissue culture polystyrene; TGFbeta2 for transforming growth factor beta2; TGF beta-3 for transforming growth factor beta-3; TIMP1 for tissue inhibitor of matrix metalloproteinase 1; TPO for thrombopoietin; TuJ1 for BetaIII Tubulin; VEGF for vascular endothelial growth factor; vWF for von Willebrand factor; and alphaFP for alpha-fetoprotein.

As used in the following examples and elsewhere in the specification, the term Growth Medium generally refers to a medium sufficient for the culturing of PPDCs. In particular, one presently preferred medium for the culturing of the cells of the invention in comprises Dulbecco's Minimal Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics ((preferably 50-100 Units/milliliter penicillin, 50-100 microgram/milliliter streptomycin, and 0-0.25 microgram/milliliter amphotericin B; Invitrogen, Carlsbad, Calif.)), and 0.001% (v/v) 2-mercaptoethanol (Sigma, St. Louis, Mo.). As used in the Examples below, Growth Medium refers to DMEM-low glucose with 15% fetal bovine serum and antibiotics/antimycotics (when penicillin/streptomycin are included, it is preferably at 50 U/milliliter and 50 microgram/milliliter respectively; when penicillin/streptomycin/ amphotericin B are use, it is preferably at 100 U/milliliter, 100 microgram/milliliter and 0.25 microgram/milliliter, respectively). In some cases different growth media are used, or different supplementations are provided, and these are normally indicated in the text as supplementations to Growth Medium.

Also relating to the following examples and used elsewhere in the specification, the term standard growth conditions refers to culturing of cells at 37° C., in a standard atmosphere comprising 5% $CO_2$. While foregoing the conditions are useful for culturing, it is to be understood that such conditions are capable of being varied by the skilled artisan who will appreciate the options available in the art for culturing cells.

EXAMPLE 1

Derivation of Cells from Postpartum Tissue

This example describes the preparation of postpartum-derived cells from placental and umbilical cord tissues. Postpartum umbilical cords and placentae were obtained upon birth of either a full term or pre-term pregnancy. Cells were harvested from 5 separate donors of umbilicus and placental tissue. Different methods of cell isolation were tested for their ability to yield cells with: 1) the potential to differentiate into cells with different phenotypes, a characteristic common to stem cells, or 2) the potential to provide trophic factors useful for other cells and tissues.

Methods & Materials

Umbilical cell isolation. Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the cord was washed in phosphate buffered saline (PBS; Invitrogen, Carlsbad, Calif.) in the presence of antimycotic and antibiotic (100 units/milliliter penicillin, 100 micrograms/ milliliter streptomycin, 0.25 micrograms/milliliter amphotericin B). The tissues were then mechanically dissociated in 150 $cm^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic as described above. In some experiments, an enzyme mixture of collagenase and dispase was used ("C:D;" collagenase (Sigma, St. Louis, Mo.), 500 Units/milliliter; and dispase (Invitrogen), 50 Units/milliliter in DMEM:-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM:-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of Growth Medium (DMEM:Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 1 milliliter per 100 milliliters of antibiotic/antimycotic as described above. The cell suspension was filtered through a 70-micrometer nylon cell strainer (BD Biosciences). An additional 5 milliliters rinse comprising Growth Medium was passed through the strainer. The cell suspension was then passed through a 40-micrometer nylon cell strainer (BD Biosciences) and chased with a rinse of an additional 5 milliliters of Growth Medium.

The filtrate was resuspended in Growth Medium (total volume 50 milliliters) and centrifuged at 150×g for 5 minutes. The supernatant was aspirated and the cells were resuspended in 50 milliliters of fresh Growth Medium. This process was repeated twice more.

Upon the final centrifugation supernatant was aspirated and the cell pellet was resuspended in 5 milliliters of fresh Growth Medium. The number of viable cells was determined using Trypan Blue staining. Cells were then cultured under standard conditions.

The cells isolated from umbilical cords were seeded at 5,000 cells/$cm^2$ onto gelatin-coated T-75 $cm^2$ flasks (Corning Inc., Corning, N.Y.) in Growth Medium with antibiotics/ antimycotics as described above. After 2 days (in various experiments, cells were incubated from 2-4 days), spent medium was aspirated from the flasks. Cells were washed with PBS three times to remove debris and blood-derived cells. Cells were then replenished with Growth Medium and allowed to grow to confluence (about 10 days from passage 0) to passage 1. On subsequent passages (from passage 1 to 2 and so on), cells reached sub-confluence (75-85 percent confluence) in 4-5 days. For these subsequent passages, cells were seeded at 5000 cells/$cm^2$. Cells were grown in a humidified incubator with 5 percent carbon dioxide and atmospheric oxygen, at 37° C.

Placental Cell Isolation. Placental tissue was obtained from NDRI (Philadelphia, Pa.). The tissues were from a pregnancy and were obtained at the time of a normal surgical delivery. Placental cells were isolated as described for umbilical cell isolation.

The following example applies to the isolation of separate populations of maternal-derived and neonatal-derived cells from placental tissue.

The cell isolation protocol was performed aseptically in a laminar flow hood. The placental tissue was washed in phosphate buffered saline (PBS; Invitrogen, Carlsbad, Calif.) in the presence of antimycotic and antibiotic (as described above) to remove blood and debris. The placental tissue was then dissected into three sections: top-line (neonatal side or aspect), mid-line (mixed cell isolation neonatal and maternal) and bottom line (maternal side or aspect).

The separated sections were individually washed several times in PBS with antibiotic/antimycotic to further remove blood and debris. Each section was then mechanically dissociated in 150 cm$^2$ tissue culture plates in the presence of 50 milliliters of DMEM/Low glucose, to a fine pulp. The pulp was transferred to 50 milliliter conical tubes. Each tube contained approximately 5 grams of tissue. The tissue was digested in either DMEM-Low glucose or DMEM-High glucose medium containing antimycotic and antibiotic (100 U/milliliter penicillin, 100 micrograms/milliliter streptomycin, 0.25 micrograms/milliliter amphotericin B) and digestion enzymes. In some experiments an enzyme mixture of collagenase and dispase ("C:D") was used containing collagenase (Sigma, St. Louis, Mo.) at 500 Units/milliliter and dispase (Invitrogen) at 50 Units/milliliter in DMEM-Low glucose medium. In other experiments a mixture of collagenase, dispase and hyaluronidase (C:D:H) was used (collagenase, 500 Units/milliliter; dispase, 50 Units/milliliter; and hyaluronidase (Sigma), 5 Units/milliliter in DMEM-Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at 150×g for 5 minutes, the resultant supernatant was aspirated off. The pellet was resuspended in 20 milliliters of Growth Medium with penicillin/streptomycin/amphotericin B. The cell suspension was filtered through a 70 micrometer nylon cell strainer (BD Biosciences), chased by a rinse with an additional 5 milliliters of Growth Medium. The total cell suspension was passed through a 40 micrometer nylon cell strainer (BD Biosciences) followed with an additional 5 milliliters of Growth Medium as a rinse.

The filtrate was resuspended in Growth Medium (total volume 50 milliliters) and centrifuged at 150×g for 5 minutes. The supernatant was aspirated and the cell pellet was resuspended in 50 milliliters of fresh Growth Medium. This process was repeated twice more. After the final centrifugation, supernatant was aspirated and the cell pellet was resuspended in 5 milliliters of fresh Growth Medium. A cell count was determined using the Trypan Blue Exclusion test. Cells were then cultured at standard conditions.

LIBERASE Cell Isolation. Cells were isolated from umbilicus tissues in DMEM-Low glucose medium with LIBERASE (Boehringer Mannheim Corp., Indianapolis, Ind.) (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above, using the LIBERASE/hyaluronidase mixture in place of the C:D or C:D:H enzyme mixture. Tissue digestion with LIBERASE resulted in the isolation of cell populations from postpartum tissues that expanded readily.

Cell isolation using other enzyme combinations. Procedures were compared for isolating cells from the umbilical cord using differing enzyme combinations. Enzymes compared for digestion included: i) collagenase; ii) dispase; iii) hyaluronidase; iv) collagenase:dispase mixture (C;D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 1-1).

TABLE 1-1

Isolation of cells from umbilical cord tissue using varying enzyme combinations

| Enzyme Digest | Cells Isolated | Cell Expansion |
|---|---|---|
| Collagenase | X | X |
| Dispase | +(>10 h) | + |
| Hyaluronidase | X | X |
| Collagenase:Dispase | ++(<3 h) | ++ |
| Collagenase:Hyaluronidase | ++(<3 h) | + |
| Dispase:Hyaluronidase | +(>10 h) | + |
| Collagenase:Dispase:Hyaluronidase | +++(<3 h) | +++ |

Key:
+ = good,
++ = very good,
+++ = excellent,
X = no success under conditions tested Isolation of cells from residual blood in the cords. Other attempts were made to isolate pools of cells from umbilical cord by different approaches. In one instance umbilical cord was sliced and washed with Growth Medium to dislodge the blood clots and gelatinous material. The mixture of blood, gelatinous material and Growth Medium was collected and centrifuged at 150×g. The pellet was resuspended and seeded onto gelatin-coated flasks in Growth Medium. From these experiments a cell population was isolated that readily expanded.

Isolation of cells from cord blood. Cells have also been isolated from cord blood samples attained from NDRI. The isolation protocol used here was that of International Patent Application PCT/US02/29971 by Ho et al (Ho, T. W. et al., WO2003025149 A2). Samples (50 milliliter and 10.5 milliliters, respectively) of umbilical cord blood (NDRI, Philadelphia Pa.) were mixed with lysis buffer (filter-sterilized 155 mM ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in complete minimal essential medium (Gibco, Carlsbad Calif.) containing 10 percent fetal bovine serum(Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

Isolation of cells using different enzyme combinations and growth conditions. To determine whether cell populations could be isolated under different conditions and expanded under a variety of conditions immediately after isolation, cells were digested in Growth Medium with or without 0.001 percent (v/v) 2-mercaptoethanol (Sigma, St. Louis, Mo.), using the enzyme combination of C:D:H, according to the procedures provided above. Placental-derived cells so isolated were seeded under a variety of conditions. All cells were grown in the presence of penicillin/streptomycin. (Table 1-2).

TABLE 1-2

Isolation and culture expansion of postpartum cells under varying conditions:

| Condition | Medium | 15% FBS | BME | Gelatin | 20% O2 | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |
| 7 | DMEM-Lg | N (2%) | Y | N (Fibrone) | Y | PDGF/VEGF |
| 8 | DMEM-Lg | N (2%) | Y | N (Fibrone) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibrone) | Y | PDGF/VEGF |
| 16 | DMEM-Lg | N (2%) | N | N (Fibrone) | N (5%) | PDGF/VEGF |

Isolation of cells using different enzyme combinations and growth conditions. In all conditions cells attached and expanded well between passage 0 and 1 (Table 1-2). Cells in conditions 5-8 and 13-16 were demonstrated to proliferate well up to 4 passages after seeding at which point they were cryopreserved and banked.

Results

Cell isolation using different enzyme combinations. The combination of C:D:H, provided the best cell yield following isolation, and generated cells which expanded for many more generations in culture than the other conditions (Table 1). An expandable cell population was not attained using collagenase or hyaluronidase alone. No attempt was made to determine if this result is specific to the collagen that was tested.

Isolation of cells using different enzyme combinations and growth conditions. Cells attached and expanded well between passage 0 and 1 under all conditions tested for enzyme digestion and growth (Table 2). Cells in experimental conditions 5-8 and 13-16 proliferated well up to 4 passages after seeding, at which point they were cryopreserved. All cells were banked for further investigation.

Isolation of cells from residual blood in the cords. Nucleated cells attached and grew rapidly. These cells were analyzed by flow cytometry and were similar to cells obtained by enzyme digestion.

Isolation of cells from cord blood. The preparations contained red blood cells and platelets. No nucleated cells attached and divided during the first 3 weeks. The medium was changed 3 weeks after seeding and no cells were observed to attach and grow.

Summary. Populations of cells can be derived from umbilical cord and placental tissue efficiently using the enzyme combination collagenase (a matrix metalloprotease), dispase (a neutral protease) and hyaluronidase (a mucolytic enzyme that breaks down hyaluronic acid). LIBERASE, which is a Blendzyme, may also be used. Specifically, Blendzyme 3, which is collagenase (4 Wunsch units/g) and thermolysin (1714 casein Units/g) was also used together with hyaluronidase to isolate cells. These cells expanded readily over many passages when cultured in Growth Medium on gelatin coated plastic.

Cells were also isolated from residual blood in the cords, but not cord blood. The presence of cells in blood clots washed from the tissue, that adhere and grow under the conditions used, may be due to cells being released during the dissection process.

EXAMPLE 2

Growth Characteristics of Postpartum-Derived Cells

The cell expansion potential of postpartum-derived cells (PPDCs) was compared to other populations of isolated stem cells. The process of cell expansion to senescence is referred to as Hayflick's limit (Hayflick L. 1974a, 1974b). Postpartum-derived cells are highly suited for therapeutic use because they can be readily expanded to sufficient cell numbers.

Materials and Methods

Gelatin-coating flasks. Tissue culture plastic flasks were coated by adding 20 milliliters 2% (w/v) porcine gelatin (Type B: 225 Bloom; Sigma, St. Louis, Mo.) to a T75 flask (Corning, Corning, N.Y.) for 20 minutes at room temperature. After removing the gelatin solution, 10 milliliters phosphate-buffered saline (PBS) (Invitrogen, Carlsbad, Calif.) was added and then aspirated.

Comparison of expansion potential of PPDCs with other cell populations. For comparison of growth expansion potential the following cell populations were utilized; i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot # 9F0844; Cambrex, Walkersville, Md.); iv) Umbilicus-derived cells; and v) Placenta-derived cells. Cells were initially seeded at 5,000 cells/cm² on gelatin-coated T75 flasks in Growth Medium with penicillin/streptomycin/amphotericin B. For subsequent passages, cell cultures were treated as follows. After trypsinization, viable cells were counted after Trypan Blue staining. Cell suspension (50 microliters) was combined with Trypan Blue (50 milliliters, Sigma, St. Louis Mo.). Viable cell numbers were estimated using a hemocytometer.

Following counting, cells were seeded at 5,000 cells/cm² onto gelatin-coated T 75 flasks in 25 milliliters of fresh Growth Medium. Cells were grown under standard conditions at 37° C. The Growth Medium was changed twice per week. When cells reached about 85 percent confluence they were passaged; this process was repeated until the cells reached senescence.

At each passage, cells were trypsinized and counted. The viable cell yield, population doubling [ln(cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion potential of cell banks at low density. The expansion potential of cells banked at passage 10 was also tested, using a different set of conditions. Normal dermal skin fibroblasts (cc-2509 lot # 9F0844; Cambrex, Walkersville, Md.), umbilicus-derived cells, and placenta-derived cells were tested. These cell populations had been banked at passage 10 previously, having been cultured at 5,000 cells/cm$^2$ and grown to confluence at each passage to that point. The effect of cell density on the cell populations following cell thaw at passage 10 was determined. Cells were thawed under standard conditions and counted using Trypan Blue staining. Thawed cells were then seeded at 1000 cells/cm$^2$ in DMEM: Low glucose Growth Medium with antibiotic/antimycotic as described above. Cells were grown under standard atmospheric conditions at 37° C. Growth Medium was changed twice a week and cells were passaged as they reached about 85% confluence. Cells were subsequently passaged until senescence, i.e., until they could not be expanded any further. Cells were trypsinized and counted at each passage. The cell yield, population doubling (ln(cell final/cell initial)/ln 2) and doubling time (time in culture (h)/population doubling). The total cell yield per passage was determined by multiplying total yield for the previous passage by the expansion factor for each passage (i.e., expansion factor=cell final/cell initial).

Expansion of PPDCs at low density from initial cell seeding. The expansion potential of freshly isolated PPDCs under low cell seeding conditions was tested. PPDDs were prepared as described herein. Cells were seeded at 1000 cells/cm$^2$ and passaged as described above until senescence. Cells were grown under standard atmospheric conditions at 37° C. Growth Medium was changed twice per week. Cells were passaged as they reached about 85% confluence. At each passage, cells were trypsinized and counted by Trypan Blue staining. The cell yield, population doubling (ln(cell final/cell initial)/ln 2) and doubling time (time in culture (h)/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of clonal neonatal placenta-derived cells. Cloning was used in order to expand a population of neonatal cells from placental tissue. Following isolation of three differential cell populations from the placenta (as described herein), these cell populations were expanded under standard growth conditions and then karyotyped to reveal the identity of the isolated cell populations. Because the cells were isolated from a mother who delivered a boy, it was straightforward to distinguish between the male and female chromosomes by performing metaphase spreads. These experiments demonstrated that fetal-aspect cells were karyotype positive for neonatal phenotpye, mid-layer cells were karyotype positive for both neonatal and maternal phenotypes and maternal-aspect cells were karyotype positive for maternal cells.

Expansion of cells in low oxygen culture conditions. It has been demonstrated that low oxygen cell culture conditions can improve cell expansion in certain circumstances (US20040005704). To determine if cell expansion of PPDCs could be improved by altering cell culture conditions, cultures of umbilical-derived cells were grown in low oxygen conditions. Cells were seeded at 5000 cells/cm$^2$ in Growth Medium on gelatin coated flasks. Cells were initially cultured under standard atmospheric conditions through passage 5, at which point they were transferred to low oxygen (5% $O_2$) culture conditions.

Other growth conditions. In other protocols, cells were expanded on non-coated, collagen-coated, fibronectin-coated, laminin-coated and extracellular matrix protein-coated plates. Cultures have been demonstrated to expand well on these different matrices.

Results

Comparison of expansion potential of PPDCs with other stem cell and non-stem cell populations. Both umbilical-derived and placenta-derived cells expanded for greater than 40 passages generating cell yields of >1E17 cells in 60 days. In contrast, MSCs and fibroblasts senesced after <25 days and <60 days, respectively. Although adipose-derived cells expanded for almost 60 days they generated total cell yields of 4.5E12. Thus, when seeded at 5000 cells/cm$^2$ under the experimental conditions utilized, postpartum-derived cells expanded much better than the other cell types grown under the same conditions (Table 2-1).

TABLE 2-1

Growth characteristics for different cell populations grown to senescence

| Cell Type | Senescence | Total Population Doublings | Total Cell Yield |
|---|---|---|---|
| MSC | 24 d | 8 | 4.72E7 |
| Adipose | 57 d | 24 | 4.5E12 |
| Fibroblasts | 53 d | 26 | 2.82E13 |
| Umbilicus | 65 d | 42 | 6.15E17 |
| Placenta | 80 d | 46 | 2.49E19 |

Expansion potential of cell banks at low density. Umbilicus-derived, placenta-derived and fibroblast cells expanded for greater than 10 passages generating cell yields of >1E11 cells in 60 days (Table 2-2). After 60 days under these conditions the fibroblasts became senescent whereas the umbilicus-derived and placenta-derived cell populations senesced after 80 days, completing >50 and >40 population doublings respectively.

TABLE 2-2

Growth characteristics for different cell populations using low density growth expansion from passage 10 until senescence

| Cell Type | Senescence | Total Population Doublings | Total Cell Yield |
|---|---|---|---|
| Fibroblast (P10) | 80 d | 43.68 | 2.59E11 |
| Umbilicus (P10) | 80 d | 53.6 | 1.25E14 |
| Placenta (P10) | 60 d | 32.96 | 6.09E12 |

Expansion of PPDCs at low density from initial cell seeding. PPDCs were expanded at low density (1,000 cells/cm$^2$) on gelatin-coated and uncoated plates or flasks. Growth potential of these cells under these conditions was good. The cells expanded readily in a log phase growth. The rate of cell expansion was similar to that observed when placenta-derived cells were seeded at 5000 cells/cm$^2$ on gelatin-coated flasks in Growth Medium. No differences were observed in cell expansion potential between culturing on either uncoated flasks or gelatin-coated flasks. However, cells appeared phenotypically much smaller on gelatin-coated flasks and more larger cell phenotypes were observed on uncoated flasks.

Expansion of clonal neonatal or maternal placenta-derived cells. A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin coated plates. From this initial cloning, expansive clones are identified, trypsinized, and reseeded in 12-well gelatin-coated plates in Growth medium and then subsequently passaged into T25 gelatin-coated flasks at 5,000 cells/cm$^2$ in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells cm$^2$/flask. Cells are passaged at 5,000 cells cm$^2$/T75 flask. The growth characteristics of a clone may be plotted to demonstrate cell expansion. Karyotyping analysis can confirm that the clone is either neonatal or maternal.

Expansion of cells in low oxygen culture conditions. Cells expanded well under the reduced oxygen conditions, however, culturing under low oxygen conditions did not appear to have a significant effect on cell expansion of PPDCs under the conditions used.

Summary. Cell expansion conditions comprising growing isolated postpartum-derived cells at densities of about 5000 cells/cm$^2$, in Growth Medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1000 cells/cm$^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

References for Example 2
1) Hayflick L. 1974a. *J Am Geriatr Soc.* 22:1-12.
2) Hayflick L. 1974b. *Gerontologist.* 14:37-45.
3) U.S. Patent publication US20040058412
4) U.S. Patent publication US20040048372
5) U.S. Patent publication US20040005704.

EXAMPLE 3

Evaluation of Growth Media for Placenta-Derived Cells

Several cell culture media were evaluated for their ability to support the growth of placenta-derived cells. The growth of placenta-derived cells in normal (20%) and low (5%) oxygen was assessed after 3 days using the MTS colorimetric assay.

Methods & Materials

Placenta-derived cells at passage 8 (P8) were seeded at 1×10$^3$ cells/well in 96 well plates in Growth Medium with penicillin/streptomycin. After 8 hours the medium was changed as described below and cells were incubated in normal (atmospheric) or low (5%, v/v) oxygen at 37° C., 5% CO$_2$ for 48 hours. MTS was added to the culture medium (CELL-TITER 96 AQueous One Solution Cell Proliferation Assay, Promega, Madison, Wis.) for 3 hours and the absorbance measured at 490 nanometers (Molecular Devices, Sunnyvale Calif.).

TABLE 3-1

Culture Media

| Culture Medium | Supplier | Added fetal bovine serum % (v/v) |
|---|---|---|
| DMEM low glucose | Gibco Carlsbad CA | 0, 2 10 |
| DMEM high glucose | Gibco | 0, 2 10 |
| RPMI 1640 | Mediatech, Inc. Herndon, VA | 0, 2 10 |
| Cell gro-free (Serum-free, Protein-free | Mediatech, Inc. | — |
| Ham's F10 | Mediatech, Inc. | 0, 2 10 |
| MSCGM (complete with serum) | Cambrex, Walkersville, MD | 0, 2 10 |
| Complete-serum free w/albumin | Mediatech, Inc. | — |
| Growth Medium | NA | — |
| Ham's F12 | Mediatech, Inc. | 0, 2 10 |
| Iscove's | Mediatech, Inc. | 0, 2 10 |
| Basal Medium Eagle's | Mediatech, Inc. | |
| DMEM/F12 (1:1) | Mediatech, Inc. | 0, 2 10 |

Results

Standard curves for the MTS assay established a linear correlation between an increase in absorbance and an increase in cell number. The absorbance values obtained were converted into estimated cell numbers and the change (%) relative to the initial seeding was calculated.

The Effect of Serum. The addition of serum to media at normal oxygen conditions resulted in a reproducible dose-dependent increase in absorbance and thus the viable cell number. The addition of serum to complete MSCGM resulted in a dose-dependent decrease in absorbance. In the media without added serum, cells only grew appreciably in CELLGRO-FREE, Ham's F10 and DMEM.

The Effect of Oxygen. Reduced oxygen appeared to increase the growth rate of cells in Growth Medium, Ham's F10, and MSCGM. In decreasing order of growth, the media resulting in the best growth of the cells were Growth Medium>MSCGM>Iscove's+10% FBS=DMEM-H+10% FBS=Ham's F12+10% FBS=RPMI 1640+10% FBS.

Summary. Placenta-derived cells may be grown in a variety of culture media in normal or low oxygen. Short term growth of placenta-derived cells was determined in twelve basal media with 0, 2 and 10% (v/v) serum in 5% or atmospheric oxygen. In general, placenta-derived cells did not grow as well in serum-free conditions with the exception of Ham's F10 and CELLGRO-Free, which are also protein-free. Growth in these serum-free media was about 25-33% of the maximal growth observed with media containing 15% serum.

EXAMPLE 4

Growth of Postpartum-Derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). It was not previously known whether postpartum-derived cells could grow in medium containing D-valine.

Methods & Materials

Placenta-derived cells (P3), fibroblasts (P9) and umbilical-derived cells (P5) were seeded at $5 \times 10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth Medium (DMEM with D-valine (special order Gibco), 15% (v/v) dialyzed fetal bovine serum (Hyclone, Logan, Utah), 0.001% (v/v) betamercaptoethanol (Sigma), penicillin/streptomycin (Gibco)).

Results

Placenta-derived, umbilical-derived, and fibroblast cells seeded in the D-valine-containing medium did not proliferate, unlike cells seeded in Growth Medium containing dialyzed serum. Fibroblasts cells changed morphologically, increasing in size and changing shape. All of the cells died and eventually detached from the flask surface after 4 weeks. These results indicate that medium containing D-valine is not suitable for selectively growing postpartum-derived cells.

References for Example 4
1) Hongpaisan J. 2000. *Cell Biol Int.* 24:1-7.
2) Sordillo L M, Oliver S P, Akers R M. 1988). *Cell Biol Int Rep.* 12:355-64.

EXAMPLE 5

Cryopreservation Media for Placenta-Derived Cells

Cryopreservation media for the cryopreservation of placenta-derived cells were evaluated.

Methods & Materials

Placenta-derived cells grown in Growth Medium in a gelatin-coated T75 flask were washed with PBS and trypsinized using 1 milliliter Trypsin/EDTA (Gibco). The trypsinization was stopped by adding 10 milliliters Growth Medium. The cells were centrifuged at 150×g, supernatant removed, and the cell pellet was resuspended in 1 milliliter Growth Medium. An aliquot of cell suspension, 60 microliters, was removed and added to 60 microliters trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

1.) Growth Medium+10% (v/v) DMSO (Hybrimax, Sigma, St. Louis, Mo.)
2.) Cell Freezing medium w/DMSO, w/methyl cellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately −1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliters Growth Medium and centrifuged before the cell number and viability was estimated. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%. The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary. The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is the preferred medium of those compared for cryopreservation of placenta-derived cells.

EXAMPLE 6

Karyotype Analysis of Postpartum-Derived Cells

Cell lines used in cell therapy are preferably homogeneous and free from any contaminating cell type. Cells used in cell therapy should have a normal chromosome number (46) and structure. To identify placenta- and umbilicus-derived cell lines that are homogeneous and free from cells of non-postpartum tissue origin, karyotypes of cell samples were analyzed.

Materials and Methods

PPDCs from postpartum tissue of a male neonate were cultured in Growth Medium containing penicillin/streptomycin. Postpartum tissue from a male neonate (X,Y) was selected to allow distinction between neonatal-derived cells and maternal derived cells (X,X). Cells were seeded at 5,000 cells per square centimeter in Growth Medium in a T25 flask (Corning, Corning, N.Y.) and expanded to 80% confluence. A T25 flask containing cells was filled to the neck with Growth Medium. Samples were delivered to a clinical cytogenetics laboratory by courier (estimated lab to lab transport time is one hour). Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted as exhibiting a normal appearance. Three of the sixteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 6-1

Results of PPDC karyotype analysis

| Tissue | passage | Metaphase cells counted | Metaphase cells analyzed | Number of karyotype | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |

Key:
N—Neonatal aspect;
V—villous region;
M—maternal aspect;
C—clone

Summary. Chromosome analysis identified placenta- and umbilicus-derived cells whose karyotypes appeared normal as interpreted by a clinical cytogenetic laboratory. Karyotype analysis also identified cell lines free from maternal cells, as determined by homogeneous karyotype.

EXAMPLE 7

Evaluation of Human Postpartum-Derived Cell Surface Markers by Flow Cytometry

Characterization of cell surface proteins or "markers" by flow cytometry can be used to determine a cell line's identity. The consistency of expression can be determined from multiple donors, and in cells exposed to different processing and culturing conditions. Postpartum-derived cell (PPDC) lines isolated from the placenta and umbilicus were characterized (by flow cytometry), providing a profile for the identification of these cell lines.

Materials and Methods

Media and culture vessels. Cells were cultured in Growth Medium (Gibco Carlsbad, Calif.) with penicillin/streptomycin. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody Staining and flow cytometry analysis. Adherent cells in flasks were washed in PBS and detached with Trypsin/EDTA. Cells were harvested, centrifuged, and resuspended in 3% (v/v) FBS in PBS at a cell concentration of $1 \times 10^7$ per milliliter. In accordance with the manufacture's specifications, antibody to the cell surface marker of interest (see below) was added to one hundred microliters of cell suspension and the mixture was incubated in the dark for 30 minutes at 4° C. After incubation, cells were washed with PBS and centrifuged to remove unbound antibody. Cells were resuspended in 500 microliter PBS and analyzed by flow cytometry. Flow cytometry analysis was performed with a FACSCalibur instrument (Becton Dickinson, San Jose, Calif.).

The following antibodies to cell surface markers were used.

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

Placenta and umbilicus comparison. Placenta-derived cells were compared to umbilicus-derive cells at passage 8.

Passage to passage comparison. Placenta- and umbilicus-derived cells were analyzed at passages 8, 15, and 20.

Donor to donor comparison. To compare differences among donors, placenta-derived cells from different donors were compared to each other, and umbilicus-derived cells from different donors were compared to each other.

Surface coating comparison. Placenta-derived cells cultured on gelatin-coated flasks was compared to placenta-derived cells cultured on uncoated flasks. Umbilicus-derived cells cultured on gelatin-coated flasks was compared to umbilicus-derived cells cultured on uncoated flasks.

Digestion enzyme comparison. Four treatments used for isolation and preparation of cells were compared. Cells isolated from placenta by treatment with 1) collagenase; 2) collagenase/dispase; 3) collagenase/hyaluronidase; and 4) collagenase/hyaluronidase/dispase were compared.

Placental layer comparison. Cells derived from the maternal aspect of placental tissue were compared to cells derived from the villous region of placental tissue and cells derived from the neonatal fetal aspect of placenta.

Results

Placenta vs. umbilicus comparison. Placenta- and umbilicus-derived cells analyzed by flow cytometry showed positive expression of CD10, CD13, CD44, CD73, CD 90, PDGFr-alpha and HLA-A,B,C, indicated by the increased values of fluorescence relative to the IgG control. These cells were negative for detectable expression of CD31, CD34, CD45, CD117, CD141, and HLA-DR,DP,DQ, indicated by fluorescence values comparable to the IgG control. Variations in fluorescence values of positive curves were accounted for. The mean (i.e. CD13) and range (i.e. CD90) of the positive curves showed some variation, but the curves appeared normal, confirming a homogenous population. Both curves individually exhibited values greater than the IgG control.

Passage to passage comparison—placenta-derived cells. Placenta-derived cells at passages 8, 15, and 20 analyzed by flow cytometry all were positive for expression of CD10, CD13, CD44, CD73, CD 90, PDGFr-alpha and HLA-A,B,C, as reflected in the increased value of fluorescence relative to the IgG control. The cells were negative for expression of CD31, CD34, CD45, CD117, CD141, and HLA-DR,DP,DQ having fluorescence values consistent with the IgG control.

Passage to passage comparison—umbilicus-derived cells. Umbilicus-derived cells at passage 8, 15, and 20 analyzed by flow cytometry all expressed CD10, CD13, CD44, CD73, CD 90, PDGFr-alpha and HLA-A,B,C, indicated by increased fluorescence relative to the IgG control. These cells were negative for CD31, CD34, CD45, CD117, CD141, and HLA-DR,DP,DQ, indicated by fluorescence values consistent with the IgG control.

Donor to donor comparison—placenta-derived cells. Placenta-derived cells isolated from separate donors analyzed by flow cytometry each expressed CD10, CD13, CD44, CD73, CD 90, PDGFr-alpha and HLA-A,B,C, with increased values of fluorescence relative to the IgG control. The cells were negative for expression of CD31, CD34, CD45, CD117, CD141, and HLA-DR, DP, DQ as indicated by fluorescence value consistent with the IgG control.

Donor to donor comparison—umbilicus derived cells. Umbilicus-derived cells isolated from separate donors analyzed by flow cytometry each showed positive expression of CD10, CD13, CD44, CD73, CD 90, PDGFr-alpha and HLA-A,B,C, reflected in the increased values of fluorescence relative to the IgG control. These cells were negative for expression of CD31, CD34, CD45, CD117, and HLA-DR, DP,DQ with fluorescence values consistent with the IgG control.

The effect of surface coating with gelatin on placenta-derived cells. Placenta-derived cells expanded on either gelatin-coated or uncoated flasks analyzed by flow cytometry all expressed of CD10, CD13, CD44, CD73, CD 90, PDGFr-alpha and HLA-A,B,C, reflected in the increased values of fluorescence relative to the IgG control. These cells were negative for expression of CD31, CD34, CD45, CD117, CD141, and HLA-DR,DP,DQ indicated by fluorescence values consistent with the IgG control.

The effect of surface coating with gelatin on umbilicus-derived cells. Umbilicus-derived cells expanded on gelatin and uncoated flasks analyzed by flow cytometry all were positive for expression of CD10, CD13, CD44, CD73, CD 90, PDGFr-alpha and HLA-A,B,C, with increased values of fluorescence relative to the IgG control. These cells were negative for expression of CD31, CD34, CD45, CD117, CD141, and HLA-DR,DP,DQ, with fluorescence values consistent with the IgG control.

Effect of enzyme digestion procedure used for preparation of the cells on the cell surface marker profile. Placenta-derived cells isolated using various digestion enzymes analyzed by flow cytometry all expressed CD10, CD13, CD44, CD73, CD 90, PDGFr-alpha and HLA-A,B,C, as indicated by the increased values of fluorescence relative to the IgG control. These cells were negative for expression of CD31, CD34, CD45, CD117, CD141, and HLA-DR,DP,DQ as indicated by fluorescence values consistent with the IgG control Placental layer comparison. Cells isolated from the maternal, villous, and neonatal layers of the placenta, respectively, analyzed by flow cytometry showed positive expression of CD10, CD13, CD44, CD73, CD 90, PDGFr-alpha and HLA-A,B,C, as indicated by the increased value of fluorescence relative to the IgG control. These cells were negative for expression of CD31, CD34, CD45, CD117, CD141, and HLA-DR,DP,DQ as indicated by fluorescence values consistent with the IgG control.

Summary. Analysis of placenta- and umbilicus-derived cells by flow cytometry has established of an identity of these cell lines. Placenta- and umbilicus-derived cells are positive for CD10, CD13, CD44, CD73, CD90, PDGFr-alpha, HLA-A,B,C and negative for CD31, CD34, CD45, CD117, CD141 and HLA-DR,DP,DQ. This identity was consistent between variations in variables including the donor, passage, culture vessel surface coating, digestion enzymes, and placental layer. Some variation in individual fluorescence value histogram curve means and ranges was observed, but all positive curves under all conditions tested were normal and expressed fluorescence values greater than the IgG control, thus confirming that the cells comprise a homogenous population that has positive expression of the markers.

EXAMPLE 8

Immunohistochemical Characterization of Postpartum Tissue Phenotypes

The phenotypes of cells found within human postpartum tissues, namely umbilical cord and placenta, was analyzed by immunohistochemistry.

Materials & Methods

Tissue Preparation. Human umbilical cord and placenta tissue was harvested and immersion fixed in 4% (w/v) paraformaldehyde overnight at 4° C. Immunohistochemistry was performed using antibodies directed against the following epitopes: vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 μm thick) using a standard cryostat (Leica Microsystems) and mounted onto glass slides for staining.

Immunohistochemistry. Immunohistochemistry was performed similar to previous studies (e.g., Messina, et al., (2003) *Exper. Neurol.* 184:816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), Triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical cord characterization. Vimentin, desmin, SMA, CK18, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta characterization. Vimentin, desmin, SMA, CK18, vWF, and CD34 were all observed within the placenta and regionally specific.

GROalpha, GCP-2, ox-LDL R1, and NOGO-A Tissue Expression. None of these markers were observed within umbilical cord or placental tissue.

Summary. Vimentin, desmin, alpha-smooth muscle actin, cytokeratin 18, von Willebrand Factor, and CD 34 are expressed in cells within human umbilical cord and placenta.

EXAMPLE 9

Analysis of Postpartum Tissue-Derived Cells using Oligonucleotide Arrays

Affymetrix GENECHIP arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Materials and Methods

Isolation and culture of cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium (using DMEM-LG) on gelatin-coated tissue culture plastic flasks. The cultures were incubated at 37° C. with 5% $CO_2$.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen). The cells were grown on standard tissue-treated plastic.

Human mesenchymal stem cells (hMSC) were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at 5×104 cells/cm2. The cells were incubated at 37° C. with 5% CO2 at either standard atmospheric O2 or at 5% O2. Cells were cultured for 5 days without a media change. Media and non-adherent cells were removed after 5 days of culture. The adherent cells were maintained in culture.

Isolation of mRNA and GENECHIP Analysis. Actively growing cultures of cells were removed from the flasks with a cell scraper in cold PBS. The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA, which was then transcribed into cRNA and biotin-labeled. The biotin-labeled cRNA was hybridized with HG-U133A GENECHIP oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University Tusher, VG et al., (2001) Proc. Natl. Acad. Sci. USA 98:5116-5121).

Results

Fourteen different populations of cells were analyzed. The cells along with passage information, culture substrate, and culture media are listed in Table 9-1.

TABLE 9-1

Cells analyzed by the microarray study. Cell lines are listed by identification code along with passage at time of analysis, cell growth substrate and growth medium.

| Cell Population | Passage | Substrate | Medium |
|---|---|---|---|
| Umbilicus (022803) | 2 | Gelatin | DMEM, 15% FBS, 2-ME |
| Umbilicus (042103) | 3 | Gelatin | DMEM, 15% FBS, 2-ME |
| Umbilicus (071003) | 4 | Gelatin | DMEM, 15% FBS, 2-ME |
| Placenta (042203) | 12 | Gelatin | DMEM, 15% FBS, 2-ME |
| Placenta (042903) | 4 | Gelatin | DMEM, 15% FBS, 2-ME |
| Placenta (071003) | 3 | Gelatin | DMEM, 15% FBS, 2-ME |
| ICBM (070203) (5% O2) | 3 | Plastic | MEM, 10% FBS |
| ICBM (062703) (std. O2) | 5 | Plastic | MEM, 10% FBS |
| ICBM (062703) (5% O2) | 5 | Plastic | MEM, 10% FBS |
| hMSC (Lot 2F1655) | 3 | Plastic | MSCGM |
| hMSC (Lot 2F1656) | 3 | Plastic | MSCGM |
| hMSC (Lot 2F 1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 9-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes (i.e., the greater the distance, the less similarity exists).

TABLE 9-2

The Euclidean Distances for the Cell Pairs.

| Cell Pair | Euclidean Distance |
|---|---|
| ICBM-hMSC | 24.71 |
| Placenta-umbilical | 25.52 |
| ICBM-Fibroblast | 36.44 |
| Fibroblast-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 9-3, 9-4, and 9-5 show the expression of genes increased in placenta-derived cells (Table 9-3), increased in umbilicus-derived cells (Table 9-4), and reduced in umbilicus- and placenta-derived cells (Table 9-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

TABLE 9-3

Genes shown to have specifically increased expression in the placenta-derived cells as compared to other cell lines assayed
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | rennin | NM_000537 |
| 210004_at | oxidized low density lipoprotein (lectin-like) receptor 1 | AF035776 |
| 214993_at | Homo sapiens, clone IMAGE: 4179671, mRNA, partial cds | AF070642 |
| 202178_at | Protein kinase C, zeta | NM_002744 |
| 209780_at | hypothetical protein DKFZp564F013 | AL136883 |
| 204135_at | downregulated in ovarian cancer 1 | NM_014890 |
| 213542_at | Homo sapiens mRNA; cDNA DKFZp547K1113 (from clone DKFZp547K1113) | AI246730 |

TABLE 9-4

Genes shown to have specifically increased expression in the umbilicus-derived cells as compared to other cell lines assayed
Genes Increased in Umbilicus-Derived Cells

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C—X—C motif) ligand 1 (melanoma growth stimulating activity | NM_001511 |
| 206336_at | chemokine (C—X—C motif) ligand 6 (granulocyte chemotactic protein 2) | NM_002993 |
| 207850_at | chemokine (C—X—C motif) ligand 3 | NM_002090 |
| 203485_at | reticulon 1 | NM_021136 |
| 202644_s_at | tumor necrosis factor, alpha-induced protein 3 | NM_006290 |

TABLE 9-5

Genes shown to have decreased expression in umbilicus- and placenta-derived cells
as compared to other cell lines assayed
Genes Decreased in Umbilicus- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C—X—C motif) ligand 12 (stromal cell-derived factor 1) | U19495.1 |
| 203666_at | chemokine (C—X—C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeo box 2 (growth arrest-specific homeo box) | NM_005924.1 |
| 205817_at | sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (Drosophila) | NM_003507.1 |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeo box 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 9-6, 9-7, and 9-8 show the expression of genes increased in human fibroblasts (Table 9-6), ICBM cells (Table 9-7), and MSCs (Table 9-8).

TABLE 9-6

Genes that were shown to have increased expression in fibroblasts as compared to the other cell lines assayed.
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072
(from clone DKFZp564A072)
LIM protein (similar to rat protein kinase C-binding enigma)
inhibitor of kappa light polypeptide gene enhancer in B-cells,
kinase complex-associated protein
hypothetical protein FLJ22004
Human (clone CTG-A4) mRNA sequence
ESTs, Moderately similar to cytokine receptor-like factor 2;
cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 9-7

Genes that were shown to have increased expression in the ICBM-derived cells as compared to the other cell lines assayed.
b) Genes Increased In ICBM Cells cardiac ankyrin repeat protein
MHC class I region ORF
integrin, alpha 10
hypothetical protein FLJ22362
UDP-N-acetyl-alpha-D-galactosamine: polypeptide
N-acetylgalactosaminyltransferase 3 (GalNAc-T3)
interferon-induced protein 44
SRY (sex determining region Y)-box 9
(campomelic dysplasia, autosomal sex-reversal)
keratin associated protein 1-1
hippocalcin-like 1
jagged 1 (Alagille syndrome)
proteoglycan 1, secretory granule

TABLE 9-8

Genes that were shown to have increased expression in the MSC cells as compared to the other cell lines assayed.
c) Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene TABLE 9-8-continued Genes that were shown to have increased expression in the MSC cells as compared to the other cell lines assayed.
c) Genes Increased In MSC Cells B-cell CLL/lymphoma 6 (zinc finger protein 51)
zinc finger protein 36, C3H type, homolog (mouse)

Summary. The present examination was performed to provide a molecular characterization of the postpartum cells derived from umbilical cord and placenta. This analysis included cells derived from three different umbilical cords and three different placentas. The examination also included two different lines of dermal fibroblasts, three lines of mesenchymal stem cells, and three lines of iliac crest bone marrow cells. The mRNA that was expressed by these cells was analyzed using an oligonucleotide array that contained probes for 22,000 genes. Results showed that 290 genes are differentially expressed in these five different cell types. These genes include ten genes that are specifically increased in the placenta-derived cells and seven genes specifically increased in the umbilical cord-derived cells. Fifty-four genes were found to have specifically lower expression levels in placenta and umbilical cord, as compared with the other cell types. The expression of selected genes has been confirmed by PCR (see the example that follows). These results demonstrate that the postpartum-derived cells have a distinct gene expression profile, for example, as compared to bone marrow-derived cells and fibroblasts.

EXAMPLE 10

Cell Markers in Postpartum-Derived Cells

In the preceding example, similarities and differences in cells derived from the human placenta and the human umbilical cord were assessed by comparing their gene expression profiles with those of cells derived from other sources (using an oligonucleotide array). Six "signature" genes were identified: oxidized LDL receptor 1, interleukin-8, rennin, reticulon, chemokine receptor ligand 3 (CXC ligand 3), and granulocyte chemotactic protein 2 (GCP-2). These "signature" genes were expressed at relatively high levels in postpartum-derived cells.

The procedures described in this example were conducted to verify the microarray data and find concordance/discordance between gene and protein expression, as well as to establish a series of reliable assay for detection of unique identifiers for placenta- and umbilicus-derived cells.

Methods & Materials

Cells. Placenta-derived cells (three isolates, including one isolate predominately neonatal as identified by karyotyping analysis), umbilicus-derived cells (four isolates), and Normal Human Dermal Fibroblasts (NHDF; neonatal and adult) grown in Growth Medium with penicillin/streptomycin in a gelatin-coated T75 flask. Mesechymal Stem Cells (MSCs) were grown in Mesenchymal Stem Cell Growth Medium Bullet kit (MSCGM; Cambrex, Walkerville, Md.).

For the IL-8 protocol, cells were thawed from liquid nitrogen and plated in gelatin-coated flasks at 5,000 cells/cm$^2$, grown for 48 hours in Growth Medium and then grown for further 8 hours in 10 milliliters of serum starvation medium [DMEM-low glucose (Gibco, Carlsbad, Calif.), penicillin/streptomycin (Gibco, Carlsbad, Calif.) and 0.1% (w/v) Bovine Serum Albumin (BSA; Sigma, St. Louis, Mo.)]. After this treatment RNA was extracted and the supernatants were centrifuged at 150×g for 5 minutes to remove cellular debris. Supernatants were then frozen at −80° C. for ELISA analysis.

Cell culture for ELISA assay. Postpartum cells derived from placenta and umbilicus, as well as human fibroblasts derived from human neonatal foreskin were cultured in Growth Medium in gelatin-coated T75 flasks. Cells were frozen at passage 11 in liquid nitrogen. Cells were thawed and transferred to 15-milliliter centrifuge tubes. After centrifugation at 150×g for 5 minutes, the supernatant was discarded. Cells were resuspended in 4 milliliters culture medium and counted. Cells were grown in a 75 $cm^2$ flask containing 15 milliliters of Growth Medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of tyrpsin/EDTA (Gibco, Carlsbad, Calif.) was added each flask. After cells detached from the flask, trypsin activity was neutralized with 8 milliliters of Growth Medium. Cells were transferred to a 15 milliliters centrifuge tube and centrifuged at 150×g for 5 minutes. Supernatant was removed and 1 milliliter Growth Medium was added to each tube to resuspend the cells. Cell number was estimated using a hemocytometer.

ELISA assay. The amount of IL-8 secreted by the cells into serum starvation medium was analyzed using ELISA assays (R&D Systems, Minneapolis, Minn.). All assays were tested according to the instructions provided by the manufacturer.

Total RNA isolation. RNA was extracted from confluent postpartum-derived cells and fibroblasts or for IL-8 expression from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliters DEPC-treated water and stored at −80° C.

Reverse transcription. RNA was also extracted from human placenta and umbilicus. Tissue (30 milligram) was suspended in 700 microliters of buffer RLT containing 2-mercaptoethanol. Samples were mechanically homogenized and the RNA extraction proceeded according to manufacturer's specification. RNA was extracted with 50 microliters of DEPC-treated water and stored at −80° C. RNA was reversed transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, rennin and reticulon), were further investigated using real-time and conventional PCR.

Real-time PCR. PCR was performed on cDNA samples using Assays-on-Demand™ gene expression products: oxidized LDL receptor (Hs00234028); rennin (Hs00166915); reticulon (Hs00382515); CXC ligand 3 (Hs00171061); GCP-2 (Hs00605742); IL-8 (Hs00174103); and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 min and 95° C. for 10 min, followed by 40 cycles of 95° C. for 15 sec and 60° C. for 1 min. PCR data was analyzed according to manufacturer's specifications (User Bulletin #2 from Applied Biosystems for ABI Prism 7700 Sequence Detection System).

Conventional PCR. Conventional PCR was performed using an ABI PRISM 7700 (Perkin Elmer Applied Biosystems, Boston, Mass., USA) to confirm the results from real-time PCR. PCR was performed using 2 microliters of cDNA solution, 1×AmpliTaq Gold universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for rennin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 1. Primer concentration in the final PCR reaction was 1 micromolar except for GAPDH, which was 0.5 micromolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length Polaroid camera (VWR International, South Plainfield, N.J.).

TABLE 10-1

Primers used

| d) Primer name | Primers | |
|---|---|---|
| Oxidized LDL receptor | S: 5'-GAGAAATCCAAAGAGCAAATGG-3' | (SEQ ID NO:1) |
| | A: 5'-AGAATGGAAAACTGGAATAGG-3' | (SEQ ID NO:2) |
| Renin | S: 5'-TCTTCGATGCTTCGGATTCC-3' | (SEQ ID NO:3) |
| | A: 5'-GAATTCTCGGAATCTGTGTTG-3' | (SEQ ID NO:4) |
| Reticulon | S: 5'-TTACAAGCAGTGCAGAAAACC-3' | (SEQ ID NO:5) |
| | A: 5'-AGTAAACATTGAAACCACAGCC-3' | (SEQ ID NO:6) |
| Interleukin-8 | S: 5'-TCTGCAGCTCTGTGTGAAGG-3' | (SEQ ID NO:7) |
| | A: 5'-CTTCAAAAACTTCTCCACAACC-3' | (SEQ ID NO:8) |

TABLE 10-1-continued

Primers used

| d) Primer name | Primers | |
|---|---|---|
| Chemokine (CXC) ligand 3 | S: 5'-CCCACGCCACGCTCTCC-3'<br>A: 5'-TCCTGTCAGTTGGTGCTCC-3' | (SEQ ID NO:9)<br>(SEQ ID NO:10) |

Immunofluorescence. PPDCs were fixed with cold 4% (w/v) paraformaldehyde (Sigma-Aldrich, St. Louis, Mo.) for 10 minutes at room temperature. One isolate each of umbilicus- and placenta-derived cells at passage 0 (P0) (directly after isolation) and passage 11 (P11) (two isolates of placenta-derived, two isolates of umbilicus-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse,), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GRO alpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of cells for FACS analysis. Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$ per milliliter. One hundred microliter aliquots were delivered to conical tubes. Cells stained for intracellular antigens were permeablized with Perm/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliters PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P -4685 and M-5284; Sigma), Donkey against Goat IgG (sc-3743; Santa Cruz, Biotech.). Flow cytometry analysis was performed with FACSCalibur (Becton Dickinson San Jose, Calif.).

Results

Results of real-time PCR for selected "signature" genes performed on cDNA from cells derived from human placentae, adult and neonatal fibroblasts and Mesenchymal Stem Cells (MSCs) indicate that both oxidized LDL receptor and rennin were expressed at higher level in the placenta-derived cells as compared to other cells. The data obtained from real-time PCR were analyzed by the ΔΔCT method and expressed on a logarithmic scale. Levels of reticulon and oxidized LDL receptor expression were higher in umbilicus-derived cells as compared to other cells. No significant difference in the expression levels of CXC ligand 3 and GCP-2 were found between postpartum-derived cells and controls. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed above.

The production of the cytokine, IL-8 in postpartum was elevated in both Growth Medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilical cells and some isolates of placenta cells (Table 10-1). No IL-8 was detected in medium derived from human dermal fibroblasts.

TABLE 10-1

IL-8 protein amount measured by ELISA

| Cell type | IL-8 |
| --- | --- |
| hFibro | ND |
| Placenta Isolate 1 | ND |
| Umb Isolate 1 | 2058.42 ± 144.67 |
| Placenta Isolate 2 | ND |
| Umb Isolate 2 | 2368.86 ± 22.73 |
| Placenta Isolate 3 (normal $O_2$) | 17.27 ± 8.63 |
| Placenta Isolate 3 (low$O_2$, W/O BME) | 264.92 ± 9.88 |

Results of the ELISA assay for interleukin-8 (IL-8) performed on placenta-and umbilicus-derived cells as well as human skin fibroblasts. Values are presented here are picograms/million cells, n = 2, sem.
ND: Not Detected Placenta-derived cells were also examined for the production of oxidized LDL receptor, GCP-2 and GROalpha by FACS analysis. Cells tested positive for GCP-2. Oxidized LDL receptor and GRO were not detected by this method.

Placenta-derived cells were also tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilicus-derived cells were positive for alpha-smooth muscle actin and vimentin, with the staining pattern consistent through passage 11.

Summary. Concordance between gene expression levels measured by microarray and PCR (both real-time and conventional) has been established for four genes: oxidized LDL receptor 1, rennin, reticulon, and IL-8. The expression of these genes was differentially regulated at the mRNA level in PPDCs, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level, however GCP-2 was detected at the protein level by FACS analysis in the placenta-derived cells. Although this result is not reflected by data originally obtained from the microarray experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, in the Growth Medium and under the conditions utilized in these procedures. Cells derived from the human umbilical cord at passage 0 were probed for the expression of alpha-smooth muscle actin and vimentin, and were positive for both. The staining pattern was preserved through passage 11.

EXAMPLE 11

In Vitro Immunological Evaluation of Postpartum-Derived Cells

Postpartum-derived cells (PPDCs) were evaluated in vitro for their immunological characteristics in an effort to predict the immunological response, if any, these cells would elicit upon in vivo transplantation. PPDCs were assayed by flow cytometry for the presence of HLA-DR, HLA-DP, HLA-DQ, CD80, CD86, and B7-H2. These proteins are expressed by antigen-presenting cells (APC) and are required for the direct stimulation of naïve $CD4^+$ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, 2003, supra), CD178 (Coumans, et al., (1999) *Journal of Immunological Methods* 224, 185-196), and PD-L2 (Abbas & Lichtman, 2003, supra; Brown, et. al. (2003) *The Journal of Immunology* 170, 1257-1266). The expression of these proteins by cells residing in placental tissues is thought to mediate the immuno-privileged status of placental tissues in utero. To predict the extent to which placenta- and umbilicus-derived cell lines elicit an immune response in vivo, the cell lines were tested in a one-way mixed lymphocyte reaction (MLR).

Materials and Methods

Cell culture. Cells were cultured to confluence in Growth Medium containing penicillin/streptomycin in T75 flasks (Corning, Corning, N.Y.) coated with 2% gelatin (Sigma, St. Louis, Mo.).

Antibody Staining. Cells were washed in phosphate buffered saline (PBS) (Gibco, Carlsbad, Calif.) and detached with Trypsin/EDTA (Gibco, Carlsbad, Mo.). Cells were harvested, centrifuged, and re-suspended in 3% (v/v) FBS in PBS at a cell concentration of $1\times10^7$ per milliliter. Antibody (Table 11-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 11-1

Antibodies

| Antibody | Manufacturer | Catalog Number |
| --- | --- | --- |
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction. Cryopreserved vials of passage 10 umbilicus-derived cells labeled as cell line A and passage 11 placenta-derived cells labeled as cell line B were sent on dry ice to CTBR (Senneville, Quebec) to conduct a mixed lymphocyte reaction using CTBR SOP No. CAC-031. Peripheral blood mononuclear cells (PBMCs) were collected from multiple male and female volunteer donors. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]-thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the PPDCs was calculated as the mean proliferation of the receiver plus mitomycin C-treated postpartum cell line divided by the baseline proliferation of the receiver.

Results

Mixed lymphocyte reaction—placenta-derived cells. Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 11-2). The average stimulation index ranged from 1.3 (plate 2) to 3 (plate 1) and the allogeneic donor positive controls ranged from 46.25 (plate 2) to 279 (plate 1) (Table 11-3).

TABLE 11-2

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 (allogenic donor) Cell line type B | Proliferation baseline of receiver | 84 | 242 | 208 | 178.0 | 83.16 | 46.7 |
| | Control of autostimulation (Mitomycin treated autologous cells) | 361 | 617 | 304 | 427.3 | 166.71 | 39.0 |
| | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |
| Plate ID: Plate 2 | | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 194 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |

TABLE 11-2-continued

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 11-3

Average stimulation index of placenta cells and an allogeneic donor in a mixed lymphocyte reaction with six individual allogeneic receivers
Average Stimulation Index

| | Recipient | Placenta |
|---|---|---|
| Plate 1 (receivers 1-3) | 279 | 3 |
| Plate 2 (receivers 4-6) | 46.25 | 1.3 |

Mixed lymphocyte reaction—umbilicus-derived cells. Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and placenta cell lines were mitomycin C-treated and cultured in a mixed lymphocyte reaction with the five individual allogeneic receivers. Reactions were performed in triplicate using two cell culture plates with three receivers per plate (Table 11-4). The average stimulation index ranged from 6.5 (plate 1) to 9 (plate 2) and the allogeneic donor positive controls ranged from 42.75 (plate 1) to 70 (plate 2) (Table 11-5).

TABLE 11-4

Mixed Lymphocyte Reaction Data- Cell Line A (Umbilicus)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |

TABLE 11-4-continued

Mixed Lymphocyte Reaction Data- Cell Line A (Umbilicus)
DPM for Proliferation Assay

| Analytical number | Culture System | Replicates | | | Mean | SD | CV |
|---|---|---|---|---|---|---|---|
| | | 1 | 2 | 3 | | | |
| SI (donor) | | | | | 70 | | |
| SI (cell line) | | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 11-5

Average stimulation index of umbilicus-derived cells and an allogeneic donor in a mixed lymphocyte reaction with five individual allogeneic receivers.
Average Stimulation Index

| | Recipient | Umbilicus |
|---|---|---|
| Plate 1 (receivers 1-4) | 42.75 | 6.5 |
| Plate 2 (receiver 5) | 70 | 9 |

Antigen presenting cell markers—placenta-derived cells. Histograms of placenta-derived cells analyzed by flow cytometry show negative expression of HLA-DR, DP, DQ, CD80, CD86, and B7-H2, as noted by fluorescence value consistent with the IgG control, indicating that placental cell lines lack the cell surface molecules required to directly stimulate CD4$^+$ T cells.

Immunomodulating markers—placenta-derived cells. Histograms of placenta-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Antigen presenting cell markers—umbilicus-derived cells. Histograms of umbilicus-derived cells analyzed by flow cytometry show negative expression of HLA-DR, DP, DQ, CD80, CD86, and B7-H2, as noted by fluorescence value consistent with the IgG control, indicating that umbilical cell lines lack the cell surface molecules required to directly stimulate CD4$^+$ T cells.

Immunomodulating cell markers—umbilicus-derived cells. Histograms of umbilicus-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary. In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilicus-derived cell lines the average stimulation index ranged from 6.5 to 9, and that of the allogeneic positive controls ranged from 42.75 to 70. Placenta- and umbilicus-derived cell lines were negative for the expression of the stimulating proteins HLA-DR, HLA-DP, HLA-DQ, CD80, CD86, and B7-H2, as measured by flow cytometry. Placenta- and umbilicus-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DR, DQ, CD8, CD86, and B7-H2, thereby allowing for the stimulation of naïve CD4$^+$ T cells. The absence of antigen-presenting cell surface molecules on placenta- and umbilicus-derived cells required for the direct stimulation of naïve CD4$^+$ T cells and the presence of PD-L2, an immunomodulating protein, may account for the low stimulation index exhibited by these cells in a MLR as compared to allogeneic controls.

EXAMPLE 12

Secretion of Trophic Factors by Postpartum-Derived Cells

The secretion of selected trophic factors from placenta- and umbilicus-derived cells was measured. Factors selected for detection included: (1) those known to have angiogenic activity, such as hepatocyte growth factor (HGF) (Rosen et al. (1997) *Ciba Found. Symp.* 212:215-26), monocyte chemotactic protein 1 (MCP-1) (Salcedo et al. (2000) *Blood* 96; 34-40), interleukin-8 (IL-8) (Li et al. (2003) *J. Immunol.* 170:3369-76), keratinocyte growth factor (KGF), basic fibroblast growth factor (bFGF), vascular endothelial growth factor (VEGF) (Hughes et al. (2004) *Ann. Thorac. Surg.* 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1 alpha (SDF -1 alpha); (2) those known to have neurotrophic/neuroprotective activity, such as brain-derived neurotrophic factor (BDNF) (Cheng et al. (2003) *Dev. Biol.* 258; 319-33), interleukin-6 (IL-6), granulocyte chemotactic protein-2 (GCP-2), transforming growth factor beta2 (TGFbeta2); and (3) those known to have chemokine activity, such as macrophage inflammatory protein 1 alpha (MIP1a), macrophage inflammatory protein 1 beta (MIP1b), monocyte chemoattractant-1 (MCP -1), Rantes (regulated on activation, normal T cell expressed and secreted), I309, thymus and activation-regulated chemokine (TARC), Eotaxin, macrophage-derived chemokine (MDC), IL -8).

Methods & Materials

Cell culture. PPDCs from placenta and umbilicus as well as human fibroblasts derived from human neonatal foreskin were cultured in Growth Medium with penicillin/streptomycin on gelatin-coated T75 flasks. Cells were cryopreserved at passage 11 and stored in liquid nitrogen. After thawing of the cells, Growth Medium was added to the cells followed by transfer to a 15 milliliter centrifuge tube and centrifugation of the cells at 150×g for 5 minutes. The supernatant was discarded. The cell pellet was resuspended in 4 milliliters Growth Medium, and cells were counted. Cells were seeded at 375,000 cells/75 cm² flask containing 15 milliliters of Growth Medium and cultured for 24 hours. The medium was changed to a serum-free medium (DMEM-low glucose (Gibco), 0.1% (w/v) bovine serum albumin (Sigma), penicillin/streptomycin (Gibco)) for 8 hours. Conditioned serum-free medium was collected at the end of incubation by centrifugation at 14,000×g for 5 minutes and stored at −20° C. To estimate the number of cells in each flask, cells were washed with PBS and detached using 2 milliliters trypsin/EDTA. Trypsin activity was inhibited by addition of 8 milliliters Growth Medium. Cells were centrifuged at 150×g for 5 minutes. Supernatant was removed, and cells were resuspended in 1 milliliter Growth Medium. Cell number was estimated using a hemocytometer.

ELISA assay. Cells were grown at 37° C. in 5% carbon dioxide and atmospheric oxygen. Placenta-derived cells (batch 101503) also were grown in 5% oxygen or beta-mercaptoethanol (BME). The amount of MCP-1, IL-6, VEGF, SDF-1 alpha, GCP-2, IL-8, and TGF-beta 2 produced by each cell sample was measured by an ELISA assay (R&D Systems, Minneapolis, Minn.). All assays were performed according to the manufacturer's instructions.

SearchLight multiplexed ELISA assay. Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF were measured using SearchLight Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA assay. MCP-1 and IL-6 were secreted by placenta- and umbilicus-derived cells and dermal fibroblasts (Table 12-1). SDF-1 alpha was secreted by placenta-derived cells cultured in 5% $O_2$ and by fibroblasts. GCP-2 and IL-8 were secreted by umbilicus-derived cells and by placenta-derived cells cultured in the presence of BME or 5% $O_2$. GCP-2 also was secreted by human fibroblasts. TGF-beta2 was not detectable by ELISA assay.

TABLE 12-1

ELISA assay results
(values presented are picograms/milliliter/million cells (n = 2, sem)

| | MCP-1 | IL-6 | VEGF | SDF-1α | GCP-2 | IL-8 | TGF-β2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilicus (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilicus (071003) | 2794 ± 84 | 1356 ± 43 | ND | ND | 2184 ± 98 | 2369 ± 23 | ND |
| Placenta (101503) BME | 21 ± 10 | 67 ± 3 | ND | ND | 44 ± 9 | 17 ± 9 | ND |
| Placenta (101503) 5% $O_2$, W/O BME | 77 ± 16 | 339 ± 21 | ND | 1149 ± 137 | 54 ± 2 | 265 ± 10 | ND |

Key:
ND: Not Detected.

SearchLight multiplexed ELISA assay. TIMP1, TPO, KGF, HGF, FGF, HBEGF, BDNF, MIP1b, MCP1, RANTES, I309, TARC, MDC, and IL-8 were secreted from umbilicus-derived cells (Tables 12-2 and 12-3). TIMP1, TPO, KGF, HGF, HBEGF, BDNF, MIP1a, MCP-1, RANTES, TARC, Eotaxin, and IL-8 were secreted from placenta-derived cells (Tables 12-2 and 12-3). No Ang2, VEGF, or PDGF-bb were detected.

TABLE 12-2

SearchLight Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| Hfb | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key:
hFB (human fibroblasts),
P1 (placenta-derived cells (042303)),
U1 (umbilicus-derived cells (022803)),
P3 (placenta-derived cells (071003)),
U3 (umbilicus-derived cells (071003)).
ND: Not Detected.

TABLE 12-3

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key:
hFB (human fibroblasts),
P1 (placenta-derived PPDC (042303)),
U1 (umbilicus-derived PPDC (022803)),
P3 (placenta-derived PPDC (071003)),
U3 (umbilicus-derived PPDC (071003)).
ND: Not Detected.

Summary. Umbilicus- and placenta-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

EXAMPLE 13

Short-Term Neural Differentiation of Postpartum-Derived Cells

The ability of placenta- and umbilicus-derived cells (collectively postpartum-derived cells or PPDCs) to differentiate into neural lineage cells was examined.

Materials & Methods

Isolation and Expansion of Postpartum Cells. PPDCs from placental and umbilical tissues were isolated and expanded as described in Example 1.

Modified Woodbury-Black Protocol. (A) This assay was adapted from an assay originally performed to test the neural induction potential of bone marrow stromal cells (Woodbury, D. et al. (2000) *J. Neurosci. Res.* 61(4):364-370)(. Umbilicus-derived cells (022803) P4 and placenta-derived cells (042203) P3 were thawed and culture expanded in Growth Media at 5,000 cells/cm² until sub-confluence (75%) was reached. Cells were then trypsinized and seeded at 6,000 cells per well of a Titretek II glass slide (VWR International, Bristol, Conn.). As controls, mesenchymal stem cells (P3; 1F2155; Cambrex, Walkersville, Md.), osteoblasts (P5; CC2538; Cambrex), adipose-derived cells (Artecel, US6555374 B1) (P6; Donor 2) and neonatal human dermal fibroblasts (P6; CC2509; Cambrex) were also seeded under the same conditions.

All cells were initially expanded for 4 days in DMEM/F12 medium (Invitrogen, Carlsbad, Calif.) containing 15% (v/v) fetal bovine serum (FBS; Hyclone, Logan, Utah), basic fibroblast growth factor (bFGF; 20 nanograms/milliliter; Peprotech, Rocky Hill, N.J.), epidermal growth factor (EGF; 20 nanograms/milliliter; Peprotech) and penicillin/streptomycin (Invitrogen). After four days, cells were rinsed in phosphate-buffered saline (PBS; Invitrogen) and were subsequently cultured in DMEM/F12 medium+20% (v/v) FBS+ penicillin/streptomycin for 24 hours. After 24 hours, cells were rinsed with PBS. Cells were then cultured for 1-6 hours in an induction medium which was comprised of DMEM/F12 (serum-free) containing 200 mM butylated hydroxyanisole, 10 μM potassium chloride, 5 milligram/milliliter insulin, 10 μM forskolin, 4 μM valproic acid, and 2 μM hydrocortisone (all chemicals from Sigma, St. Louis, Mo.). Cells were then fixed in 100% ice-cold methanol and immunocytochemistry was performed (see methods below) to assess human nestin protein expression.

(B) PPDCs (umbilicus (022803) P11; placenta (042203) P11) and adult human dermal fibroblasts (1F1853, P11) were thawed and culture expanded in Growth Medium at 5,000 cells/cm2 until sub-confluence (75%) was reached. Cells were then trypsinized and seeded at similar density as in (A), but onto (1) 24 well tissue culture-treated plates (TCP, Falcon brand, VWR International), (2) TCP wells+2% (w/v) gelatin adsorbed for 1 hour at room temperature, or (3) TCP wells+20 μg/milliliter adsorbed mouse laminin (adsorbed for a minimum of 2 hours at 37° C.; Invitrogen).

Exactly as in (A), cells were initially expanded and media switched at the aforementioned timeframes. One set of cultures was fixed, as before, at 5 days and six hours, this time with ice-cold 4% (w/v) paraformaldehyde (Sigma) for 10 minutes at room temperature. In the second set of cultures, medium was removed and switched to Neural Progenitor Expansion medium (NPE) consisting of Neurobasal-A medium (Invitrogen) containing B27 (B27 supplement; Invitrogen), L-glutamine (4 mM), and penicillin/streptomycin (Invitrogen). NPE medium was further supplemented with retinoic acid (RA; 1 μM; Sigma). This medium was removed 4 days later and cultures were fixed with ice-cold 4% (w/v) paraformaldehyde (Sigma) for 10 minutes at room temperature, and stained for nestin, GFAP, and TuJ1 protein expression (see Table N1-1).

TABLE 13-1

Summary of Primary Antibodies Used

| Antibody | Concentration | Vendor |
|---|---|---|
| Rat 401 (nestin) | 1:200 | Chemicon, Temecula, CA |
| Human Nestin | 1:100 | Chemicon |
| TuJ1 (BIII Tubulin) | 1:500 | Sigma, St. Louis, MO |
| GFAP | 1:2000 | DakoCytomation, Carpinteria, CA |
| Tyrosine hydroxylase (TH) | 1:1000 | Chemicon |
| GABA | 1:400 | Chemicon |
| Desmin (mouse) | 1:300 | Chemicon |
| alpha-smooth muscle actin | 1:400 | Sigma |
| Human nuclear protein (hNuc) | 1:150 | Chemicon |

Two Stage Differentiation Protocol. PPDCs (umbilicus (042203) P11, placenta (022803) P11), adult human dermal fibroblasts (P11; 1F1853; Cambrex) were thawed and culture expanded in Growth Medium at 5,000 cells/cm² until sub-confluence (75%) was reached. Cells were then trypsinized and seeded at 2,000 cells/cm², but onto 24 well plates coated with laminin (BD Biosciences, Franklin Lakes, N.J.) in the presence of NPE media supplemented with bFGF (20 nanograms/milliliter; Peprotech, Rocky Hill, N.J.) and EGF (20 nanograms/milliliter; Peprotech) [whole media composition further referred to as NPE+F+E]. At the same time, adult rat neural progenitors isolated from hippocampus (P4; (062603) were also plated onto 24 well laminin-coated plates in NPE+F+E media. All cultures were maintained in such conditions for a period of 6 days (cells were fed once during that time) at which time media was switched to the differentiation conditions listed in Table N1-2 for an additional period of 7 days. Cultures were fixed with ice-cold 4% (w/v) paraformaldehyde (Sigma) for 10 minutes at room temperature, and stained for human or rat nestin, GFAP, and TuJ1 protein expression.

expanded in NPE+F (20 nanograms/milliliter)+E (20 nanograms/milliliter) at 5,000 cells/cm² for a period of 48 hours. Cells were then trypsinized and seeded at 2,500 cells/well onto existing cultures of neural progenitors. At that time, existing medium was exchanged for fresh medium. Four days later, cultures were fixed with ice-cold 4% (w/v) paraformaldehyde (Sigma) for 10 minutes at room temperature, and stained for human nuclear protein (hNuc; Chemicon) (Table NU1-1 above) to identify PPDCs.

Immunocytochemistry. Immunocytochemistry was performed using the antibodies listed in Table NU1-1. Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1

TABLE 13-2

B. Summary of Conditions for Two-Stage Differentiation Protocol

| COND. # | A<br>PRE-DIFFERENTIATION | B<br>2nd STAGE DIFF |
|---|---|---|
| 1 | NPE + F (20 ng/ml) + E (20 ng/ml) | NPE + SHH (200 ng/ml) + F8 (100 ng/ml) |
| 2 | NPE + F (20 ng/ml) + E (20 ng/ml) | NPE + SHH (200 ng/ml) + F8 (100 ng/ml) + RA (1 µM) |
| 3 | NPE + F (20 ng/ml) + E (20 ng/ml) | NPE + RA (1 µM) |
| 4 | NPE + F (20 ng/ml) + E (20 ng/ml) | NPE + F (20 ng/ml) + E (20 ng/ml) |
| 5 | NPE + F (20 ng/ml) + E (20 ng/ml) | Growth Medium |
| 6 | NPE + F (20 ng/ml) + E (20 ng/ml) | Condition 1B + MP52 (20 ng/ml) |
| 7 | NPE + F (20 ng/ml) + E (20 ng/ml) | Condition 1B + BMP7 (20 ng/ml) |
| 8 | NPE + F (20 ng/ml) + E (20 ng/ml) | Condition 1B + GDNF (20 ng/ml) |
| 9 | NPE + F (20 ng/ml) + E (20 ng/ml) | Condition 2B + MP52 (20 ng/ml) |
| 10 | NPE + F (20 ng/ml) + E (20 ng/ml) | Condition 2B + BMP7 (20 ng/ml) |
| 11 | NPE + F (20 ng/ml) + E (20 ng/ml) | Condition 2B + GDNF (20 ng/ml) |
| 12 | NPE + F (20 ng/ml) + E (20 ng/ml) | Condition 3B + MP52 (20 ng/ml) |
| 13 | NPE + F (20 ng/ml) + E (20 ng/ml) | Condition 3B + BMP7 (20 ng/ml) |
| 14 | NPE + F (20 ng/ml) + E (20 ng/ml) | Condition 3B + GDNF (20 ng/ml) |
| 15 | NPE + F (20 ng/ml) + E (20 ng/ml) | NPE + MP52 (20 ng/ml) |
| 16 | NPE + F (20 ng/ml) + E (20 ng/ml) | NPE + BMP7 (20 ng/ml) |
| 17 | NPE + F (20 ng/ml) + E (20 ng/ml) | NPE + GDNF (20 ng/ml) |

Multiple growth factor protocol. Umbilicus-derived cells (P11; (042203)) were thawed and culture expanded in Growth Medium at 5,000 cells/cm² until sub-confluence (75%) was reached. Cells were then trypsinized and seeded at 2,000 cells/cm², onto 24 well laminin-coated plates (BD Biosciences) in the presence of NPE+F (20 nanograms/milliliter)+E (20 nanograms/milliliter). In addition, some wells contained NPE+F+E+2% FBS or 10% FBS. After four days of "pre-differentiation" conditions, all media were removed and samples were switched to NPE medium supplemented with sonic hedgehog (SHH; 200 nanograms/milliliter; Sigma, St. Louis, Mo.), FGF8 (100 nanograms/milliliter; Peprotech), BDNF (40 nanograms/milliliter; Sigma), GDNF (20 nanograms/milliliter; Sigma), and retinoic acid (1 µM; Sigma). Seven days post medium change, cultures were fixed with ice-cold 4% (w/v) paraformaldehyde (Sigma) for 10 minutes at room temperature, and stained for human nestin, GFAP, TuJ1, desmin, and alpha-smooth muscle actin expression.

Neural progenitor co-culture protocol. Adult rat hippocampal progenitors (062603) were plated as neurospheres or single cells (10,000 cells/well) onto laminin-coated 24 well dishes (BD Biosciences) in NPE+F (20 nanograms/milliliter)+E (20 nanograms/milliliter).

Separately, umbilicus-derived cells (042203) P11 and placenta-derived cells (022803) P11 were thawed and culture hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Woodbury-Black protocol. (A) Upon incubation in this neural induction composition, all cell types transformed into cells with bipolar morphologies and extended processes.

Other larger non-bipolar morphologies were also observed. Furthermore, the induced cell populations stained positively for nestin, a marker of multipotent neural stem and progenitor cells.

(B) When repeated on tissue culture plastic (TCP) dishes, nestin expression was not observed unless laminin was pre-adsorbed to the culture surface. To further assess whether nestin-expressing cells could then go on to generate mature neurons, PPDCs and fibroblasts were exposed to NPE+RA (1 µM), a media composition known to induce the differentiation of neural stem and progenitor cells into such cells (2,3,4). Cells were stained for TuJ1, a marker for immature and mature neurons, GFAP, a marker of astrocytes, and nestin. Under no conditions was TuJ1 detected, nor were cells with neuronal morphology observed, suggesting that neurons were not generated in the short term. Furthermore, nestin and GFAP were no longer expressed by PPDCs, as determined by immunocytochemistry.

Two-stage differentiation. Umbilicus and placenta PPDC isolates (as well as human fibroblasts and rodent neural progenitors as negative and positive control cell types, respectively) were plated on laminin (neural promoting)-coated dishes and exposed to 13 different growth conditions (and two control conditions) known to promote differentiation of neural progenitors into neurons and astrocytes. In addition, two conditions were added to examine the influence of GDF5, and BMP7 on PPDC differentiation. Generally, a two-step differentiation approach was taken, where the cells were first placed in neural progenitor expansion conditions for a period of 6 days, followed by full differentiation conditions for 7 days. Morphologically, both umbilicus- and placenta-derived cells exhibited fundamental changes in cell morphology throughout the time-course of this procedure. However, neuronal or astrocytic-shaped cells were not observed except for in control, neural progenitor-plated conditions. Immunocytochemistry, negative for human nestin, TuJ1, and GFAP confirmed the morphological observations.

Multiple growth factors. Following one week's exposure to a variety of neural differentiation agents, cells were stained for markers indicative of neural progenitors (human nestin), neurons (TuJ1), and astrocytes (GFAP). Cells grown in the first stage in non-serum containing media had different morphologies than those cells in serum containing (2% or 10%) media, indicating potential neural differentiation. Specifically, following a two step procedure of exposing umbilicus-derived cells to EGF and bFGF, followed by SHH, FGF8, GDNF, BDNF, and retinoic acid, cells showed long extended processes similar to the morphology of cultured astrocytes. When 2% FBS or 10% FBS was included in the first stage of differentiation, cell number was increased and cell morphology was unchanged from control cultures at high density. Potential neural differentiation was not evidenced by immunocytochemical analysis for human nestin, TuJ1, or GFAP.

Neural progenitor and PPDC co-culture. PPDCs were plated onto cultures of rat neural progenitors seeded two days earlier in neural expansion conditions (NPE+F+E). While visual confirmation of plated PPDCs proved that these cells were plated as single cells, human-specific nuclear staining (hNuc) 4 days post-plating (6 days total) showed that they tended to ball up and avoid contact with the neural progenitors. Furthermore, where PPDCs attached, these cells spread out and appeared to be innervated by differentiated neurons that were of rat origin, suggesting that the PPDCs may have differentiated into muscle cells. This observation was based upon morphology under phase contrast microscopy. Another observation was that typically large cell bodies (larger than neural progenitors) possessed morphologies resembling neural progenitors, with thin processes spanning out in multiple directions. HNuc staining (found in one half of the cell's nucleus) suggested that in some cases these human cells may have fused with rat progenitors and assumed their phenotype. Control wells containing only neural progenitors had fewer total progenitors and apparent differentiated cells than did co-culture wells containing umbilicus or placenta PPDCs, further indicating that both umbilicus- and placenta-derived cells influenced the differentiation and behavior of neural progenitors, either by release of chemokines and cytokines, or by contact-mediated effects.

Summary. Multiple protocols were conducted to determine the short term potential of PPDCs to differentiate into neural lineage cells. These included phase contrast imaging of morphology in combination with immunocytochemistry for nestin, TuJ1, and GFAP, proteins associated with multipotent neural stem and progenitor cells, immature and mature neurons, and astrocytes, respectively. Evidence was observed to suggest that neural differentiation occurred in certain instances in these short-term protocols.

Several notable observations were made in co-cultures of PPDCs with neural progenitors. This approach, using human PPDCs along with a xenogeneic cell type allowed for absolute determination of the origin of each cell in these cultures. First, some cells were observed in these cultures where the cell cytoplasm was enlarged, with neurite-like processes extending away from the cell body, yet only half of the body labeled with hNuc protein. Those cells may have been human PPDCs that had differentiated into neural lineage cells or they may have been PPDCs that had fused with neural progenitors. Second, it appeared that neural progenitors extended neurites to PPDCs in a way that indicates the progenitors differentiated into neurons and innervated the PPDCs. Third, cultures of neural progenitors and PPDCs had more cells of rat origin and larger amounts of differentiation than control cultures of neural progenitors alone, further indicating that plated PPDCs provided soluble factors and or contact-dependent mechanisms that stimulated neural progenitor survival, proliferation, and/or differentiation.

References for Example 13
(1) Woodbury, D. et al. (2000) *J. Neurosci. Res.* 61(4):364-370.
(2) Jang, Y K et al. (2004) *J. Neurosci. Res.* 75(4):573-584.
(3) Jones-Villeneuve, E M et al. (1983) *Mol. Cell. Biol.* 3(12):2271-2279.
(4) Mayer-Proschel, M. et al. (1997) *Neuron.* 19(4):773-785.

EXAMPLE 14

Long-Term Neural Differentiation of Postpartum-Derived Cells

The ability of umbilicus and placenta-derived cells (collectively postpartum-derived cells or PPDCs) to undergo long-term differentiation into neural lineage cells was evaluated.

Materials & Methods

Isolation and Expansion of PPDCs. PPDCs were isolated and expanded as described in previous Examples.

PPDC Cell Thaw and Plating. Frozen aliquots of PPDCs (umbilicus (022803) P11; (042203) P11; (071003) P12; placenta (101503) P7) previously grown in Growth Medium were thawed and plated at 5,000 cells/cm$^2$ in T-75 flasks coated with laminin (BD, Franklin Lakes, N.J.) in Neurobasal-A medium (Invitrogen, Carlsbad, Calif.) containing B27 (B27 supplement, Invitrogen), L-glutamine (4 mM), and Penicillin/Streptomycin (10 milliliters), the combination of which is herein referred to as Neural Progenitor Expansion (NPE) media. NPE media was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Control Cell Plating. In addition, adult human dermal fibroblasts (P11, Cambrex, Walkersville, Md.) and mesenchymal stem cells (P5, Cambrex) were thawed and plated at the same cell seeding density on laminin-coated T-75 flasks in NPE+bFGF+EGF. As a further control, fibroblasts, umbilicus, and placenta PPDCs were grown in Growth Medium for the period specified for all cultures.

Cell Expansion. Media from all cultures were replaced with fresh media once a week and cells observed for expansion. In general, each culture was passaged one time over a period of one month because of limited growth in NPE+bFGF+EGF.

Immunocytochemistry. After a period of one month, all flasks were fixed with cold 4% (w/v) paraformaldehyde (Sigma) for 10 minutes at room temperature. Immunocytochemistry was performed using antibodies directed against TuJ1 (BetaIII Tubulin; 1:500; Sigma, St. Louis, Mo.) and GFAP (glial fibrillary acidic protein; 1:2000; DakoCytomation, Carpinteria, Calif.). Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing block along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 14-1

Summary of Primary Antibodies Used

| Antibody | Concentration | Vendor |
| --- | --- | --- |
| TuJ1 (BetaIII Tubulin) | 1:500 | Sigma, St. Louis, MO |
| GFAP | 1:2000 | DakoCytomation, Carpinteria, CA |

Results

NPE+bFGF+EGF media slows proliferation of PPDCs and alters their morphology. Immediately following plating, a subset of PPDCs attached to the culture flasks coated with laminin. This may have been due to cell death as a function of the freeze/thaw process or because of the new growth conditions. Cells that did attach adopted morphologies different from those observed in Growth Media.

Upon confluence, cultures were passaged and observed for growth. Very little expansion took place of those cells that survived passage. At this point, very small cells with no spread morphology and with phase-bright characteristics began to appear in cultures of umbilicus-derived cells. These areas of the flask were followed over time. From these small cells, bifurcating processes emerged with varicosities along their lengths, features very similar to previously described PSA-NCAM+ neuronal progenitors and TuJ1+ immature neurons derived from brain and spinal cord (1, 2). With time, these cells became more numerous, yet still were only found in clones.

Clones of umbilicus-derived cells express neuronal proteins. Cultures were fixed at one month post-thawing/plating and stained for the neuronal protein TuJ1 and GFAP, an intermediate filament found in astrocytes. While all control cultures grown in Growth Medium and human fibroblasts and MSCs grown in NPE+bFGF+EGF medium were found to be TuJ1-/GFAP-, TuJ1 was detected in the umbilicus and placenta PPDCs. Expression was observed in cells with and without neuronal-like morphologies. No expression of GFAP was observed in either culture. The percentage of cells expressing TuJ1 with neuronal-like morphologies was less than or equal to 1% of the total population (n=3 umbilicus-derived cell isolates tested). While not quantified, the percentage of TuJ1+ cells without neuronal morphologies was higher in umbilicus-derived cell cultures than placenta-derived cell cultures. These results appeared specific as age-matched controls in Growth Medium did not express TuJ1.

Summary. Methods for generating differentiated neurons (based on TuJ1 expression and neuronal morphology) from umbilicus-derived cells were developed. While expression for TuJ1 was not examined earlier than one month in vitro, it is clear that at least a small population of umbilicus-derived cells can give rise to neurons either through default differentiation or through long-term induction following one month's exposure to a minimal media supplemented with L-glutamine, basic FGF, and EGF.

References for Example 14
(1) Mayer-Proschel, M. et al. (1997) Neuron 19(4):773-785.
(2) Yang, H. et al. (2000) Proc. Natl. Acad. Sci. USA 97(24):13366-13371.

EXAMPLE 15

PPDC Trophic Factors for Neural Progenitor Support

The influence of umbilicus- and placenta-derived cells (collectively postpartum-derived cells or PPDCs) on adult neural stem and progenitor cell survival and differentiation through non-contact dependent (trophic) mechanisms was examined.

Materials & Methods

Adult neural stem and progenitor cell isolation. Fisher 344 adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (Paxinos, G. & Watson, C. 1997. THE RAT BRAIN IN STEREOTAXIC COORDINATES). Tissue was washed in Neurobasal-A medium (Invitrogen, Carlsbad, Calif.) containing B27 (B27 supplement; Invitrogen), L-glutamine (4 mM; Invitrogen), and penicillin/streptomycin (Invitrogen), the combination of which is herein referred to as Neural Progenitor Expansion (NPE) medium. NPE medium was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNAse (100 microliters per 8 milliliters total volume, Sigma, St. Louis, Mo.) was also added. Next, the tissue/media was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250 g. Supernatant was removed, fresh NPE+bFGF+EGF was added and the pellet resuspended. The resultant cell suspension was passed through a 40 micrometer cell strainer (Becton Dickinson), plated on laminin-coated T-75 flasks (Becton Dickinson) or low cluster 24-well plates (Becton Dickinson), and grown in NPE+bFGF+EGF media until sufficient cell numbers were obtained for the studies outlined.

PPDC plating. Postpartum-derived cells (umbilicus (022803) P12, (042103) P12, (071003) P12; placenta (042203) P12) previously grown in Growth Medium were plated at 5,000 cells/transwell insert (sized for 24 well plate) and grown for a period of one week in Growth Medium in inserts to achieve confluence.

Adult neural progenitor plating. Neural progenitors, grown as neurospheres or as single cells, were seeded onto laminin-coated 24 well plates at an approximate density of 2,000 cells/well in NPE+bFGF+EGF for a period of one day to promote cellular attachment. One day later, transwell inserts containing postpartum cells were added according to the following scheme:
(1) Transwell (umbilicus-derived cells in Growth Media, 200 microliters)+neural progenitors (NPE+bFGF+EGF, 1 milliliter)
(2) Transwell (placenta-derived cells in Growth Media, 200 microliters)+neural progenitors (NPE+bFGF+EGF, 1 milliliter)
(3) Transwell (adult human dermal fibroblasts [1F1853; Cambrex, Walkersville, Md.] P12 in Growth Media, 200 microliters)+neural progenitors (NPE+bFGF+EGF, 1 milliliter)
(4) Control: neural progenitors alone (NPE+bFGF+EGF, 1 milliliter)
(5) Control: neural progenitors alone (NPE only, 1 milliliter)

Immunocytochemistry. After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 15-1. Briefly, cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 15-1

Summary of Primary Antibodies Used

| Antibody | Concentration | Vendor |
|---|---|---|
| Rat 401 (nestin) | 1:200 | Chemicon, Temecula, CA |
| TuJ1 (BetaIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpinteria, CA |
| Myelin Basic Protein (MBP) | 1:400 | Chemicon |

Quantitative analysis of neural progenitor differentiation. Quantification of hippocampal neural progenitor differentiation was examined. A minimum of 1000 cells were counted per condition or if less, the total number of cells observed in that condition. The percentage of cells positive for a given stain was assessed by dividing the number of positive cells by the total number of cells as determined by DAPI (nuclear) staining.

Mass spectrometry analysis & 2D gel electrophoresis. In order to identify unique, secreted factors as a result of co-culture, conditioned media samples taken prior to culture fixation were frozen down at −80° C. overnight. Samples were then applied to ultrafiltration spin devices (MW cutoff 30 kD). Retentate was applied to immunoaffinity chromatography (anti-Hu-albumin; IgY) (immunoaffinity did not remove albumin from the samples). Filtrate was analyzed by MALDI. The pass through was applied to Cibachron Blue affinity chromatography. Samples were analyzed by SDS-PAGE and 2D gel electrophoresis.

Results

PPDC co-culture stimulates adult neural progenitor differentiation. Following culture with umbilicus- or placenta-derived cells, co-cultured neural progenitor cells derived from adult rat hippocampus exhibited significant differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells. While both umbilicus- and placenta-derived cells induced cell differentiation, the degree of differentiation for all three lineages was less in co-cultures with placenta-derived cells than in co-cultures with umbilicus-derived cells.

The percentage of differentiated neural progenitors following co-culture with umbilicus-derived cells was quantified (Table 15-2). Umbilicus-derived cells significantly enhanced the number of mature oligodendrocytes (MBP) (24.0% vs 0% in both control conditions). Furthermore, co-culture enhanced the number of GFAP+ astrocytes and TuJ1+neurons in culture (47.2% and 8.7% respectively). These results were confirmed by nestin staining indicating that progenitor status was lost following co-culture (13.4% vs 71.4% in control condition 4).

Though differentiation also appeared to be influenced by adult human fibroblasts, such cells were not able to promote the differentiation of mature oligodendrocytes nor were they able to generate an appreciable quantity of neurons. Though not quantified, fibroblasts did, however, appear to enhance the survival of neural progenitors.

TABLE 15-2

Quantification of progenitor differentiation in control vs transwell co-culture with umbilical-derived cells (E = EGF, F = bFGF)

| Antibody | F + E/Umb [Cond. 1] | F + E/F + E [Cond. 4] | F + E/removed [Cond. 5] |
|---|---|---|---|
| TuJ1 | 8.7% | 2.3% | 3.6% |
| GFAP | 47.2% | 30.2% | 10.9% |
| MBP | 23.0% | 0% | 0% |
| Nestin | 13.4% | 71.4% | 39.4% |

Identification of unique compounds. Conditioned media from umbilicus- and placenta-derived co-cultures, along with the appropriate controls (NPE media±1.7% serum, media from co-culture with fibroblasts), were examined for differences. Potentially unique compounds were identified and excised from their respective 2D gels.

Summary. Co-culture of adult neural progenitor cells with umbilicus or placenta PPDCs results in differentiation of those cells. Results presented in this example indicate that the differentiation of adult neural progenitor cells following co-culture with umbilicus-derived cells is particularly profound. Specifically, a significant percentage of mature oligodendrocytes was generated in co-cultures of umbilicus-derived cells. In view of the lack of contact between the umbilicus-derived cells and the neural progenitors, this result appears to be a function of soluble factors released from the umbilicus-derived cells (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+ (indicative of astrocytes). This may be due to the fact that such significant expansion occurred throughout the course of the procedure that contact between progenitors induced this differentiation (Song, H. et al. 2002. Nature 417:(6884)39-44).

EXAMPLE 16

Transplantation of Postpartum-Derived Cells

Cells derived from the postpartum umbilicus and placenta are useful for regenerative therapies. The tissue produced by postpartum-derived cells (PPDCs) transplanted into SCID mice with a biodegradable material was evaluated. The materials evaluated were Vicryl non-woven (VNW), 35/65 PCL/PGA foam, and RAD 16 self-assembling peptide hydrogel.

Methods & Materials

Cell Culture. Placenta- and umbilicus-derived cells were grown in Growth Medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), penicillin/streptomycin (Gibco)) in a gelatin-coated flasks.

Sample Preparation. One million viable cells were seeded in 15 microliters Growth Medium onto 5 mm diameter, 2.25 mm thick VNW scaffolds (64.33 milligrams/cc; Lot#3547-47-1) or 5 mm diameter 35/65 PCL/PGA foam (Lot# 3415-53). Cells were allowed to attach for two hours before adding more Growth Medium to cover the scaffolds. Cells were grown on scaffolds overnight. Scaffolds without cells were also incubated in medium.

RAD16 self-assembling peptides (3D Matrix, Cambridge, Mass. under a material transfer agreement) was obtained as a sterile 1% (w/v) solution in water, which was mixed 1:1 with $1\times10^6$ cells in 10% (w/v) sucrose (Sigma, St Louis, Mo.), 10 mM HEPES in Dulbecco's Modified Eagle's Medium (DMEM; Gibco) immediately before use. The final concentration of cells in RAD16 hydrogel was $1\times10^6$ cells/100 microliters.

Test Material (N=4/Rx)
1. VNW+$1\times10^6$ umbilicus-derived cells
2. 35/65 PCL/PGA foam+$1\times10^6$ umbilicus-derived cells
3. RAD 16 self-assembling peptide+$1\times10^6$ umbilicus-derived cells
4. VNW+$1\times10^6$ placenta-derived cells
5. 35/65 PCL/PGA foam+$1\times10^6$ placenta-derived cells
6. RAD 16 self-assembling peptide+$1\times10^6$ placenta-derived cells
7. 35/65 PCL/PGA foam
8. VNW Animal Preparation. The animals were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (*Mus Musculus*)/Fox Chase SCID/Male (Harlan Sprague Dawley, Inc., Indianapolis, Ind.), 5 weeks of age. All handling of the SCID mice took place under a hood. The mice were individually weighed and anesthetized with an intraperitoneal injection of a mixture of 60 milligrams/kg KETASET (ketamine hydrochloride, Aveco Co., Inc., Fort Dodge, Iowa) and 10 milligrams/kg ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique. Four skin incisions, each approximately 1.0 cm in length, were made on the dorsum of the mice. Two cranial sites were located transversely over the dorsal lateral thoracic region, about 5-mm caudal to the palpated inferior edge of the scapula, with one to the left and one to the right of the vertebral column. Another two were placed transversely over the gluteal muscle area at the caudal sacro-lumbar level, about 5-mm caudal to the palpated iliac crest, with one on either side of the midline. Implants were randomly placed in these sites in accordance with the experimental design. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing. Mice were individually housed in microisolator cages throughout the course of the study within a temperature range of 64° F.-79° F. and relative humidity of 30% to 70%, and maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology. Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five-micron tissue sections were obtained by microtome and stained with hematoxylin and eosin (Poly Scientific Bay Shore, N.Y.) using routine methods.

Results

There was minimal ingrowth of tissue into foams (without cells) implanted subcutaneously in SCID mice after 30 days. In contrast there was extensive tissue fill in foams implanted with umbilical-derived cells or placenta-derived cells. Some tissue ingrowth was observed in VNW scaffolds. Non-woven scaffolds seeded with umbilicus- or placenta-derived cells showed increased matrix deposition and mature blood vessels.

Summary. Synthetic absorbable non-woven/foam discs (5.0 mm diameter×1.0 mm thick) or self-assembling peptide hydrogel were seeded with either cells derived from human umbilicus or placenta and implanted subcutaneously bilaterally in the dorsal spine region of SCID mice. The results demonstrated that postpartum-derived cells could dramatically increase good quality tissue formation in biodegradable scaffolds.

EXAMPLE 17

Use of Postpartum-Derived Cells in Nerve Repair

Retinal ganglion cell (RGC) lesions have been extensively used as models for various repair strategies in the adult mammalian CNS. It has been demonstrated that retrobulbar section of adult rodent RGC axons results in abortive sprouting (Zeng et al., 1995) and progressive death of the parent cell population (Villegas-Perez et al., 1993). Numerous studies have demonstrated the stimulatory effects of various exogenous and endogenous factors on the survival of axotomized RGC's and regeneration of their axons (Yip and So, 2000; Fischer et al., 2001). Furthermore, other studies have demonstrated that cell transplants can be used to promote regeneration of severed nerve axons (Li et al., 2003; Ramon-Cueto et al., 2000). Thus, these and other studies have demonstrated that cell based therapy can be utilized for the treatment of neural disorders that affect the spinal cord, peripheral nerves, pudendal nerves, optic nerves or other diseases/trauma due to injury in which nervous damage can occur.

Self-assembling peptides (PuraMatrix™, U.S. Pat. Nos. 5,670,483, 5,955,343, US/PCT applications US2002/0160471, WO02/062969) have been developed to act as a scaffold for cell-attachment to encapsulate cells in 3-D, plate cells in 2-D coatings, or as microcarriers in suspension cultures. Three-dimensional cell culture has required either animal-derived materials (mouse sarcoma extract), with their inherent reproducibility and cell signaling issues, or much larger synthetic scaffolds, which fail to approximate the physical nanometer-scale and chemical attributes of native ECM. RAD 16 ($NH_2$-$(RADA)_3$-COOH) and KLD ($NH_2$-$(KLDL)_3$-COOH) are synthesized in small (RAD16 is 5 nanometers) oligopeptide fragments that self-assemble into nanofibers on a scale similar to the in vivo extracellular matrix (ECM) (3D Matrix, Inc Cambridge, Mass.). The self-assembly is initiated by mono- or di-valent cations found in culture media or the physiological environment. In the protocols described in this example, RAD 16 was used as a microcarrier for the implantation of postpartum cells into the ocular defect. In this example, it is demonstrated that transplants of postpartum-derived cells PPDCs) can provide efficacy in an adult rat optic nerve axonal regeneration model.

Methods & Materials

Cells. Cultures of human adult PPDCs (umbilicus and placenta) and fibroblast cells (passage 10) were expanded for 1 passage. All cells were initially seeded at 5,000 cells/$cm^2$ on gelatin-coated T75 flasks in Growth Medium with 100 Units per milliliter penicillin, 100 micrograms per milliliter streptomycin, 0.25 micrograms per milliliter amphotericin B (Invitrogen, Carlsbad, Calif.). At passage 11 cells were trypsinized and viability was determined using trypan blue staining. Briefly, 50 microliters of cell suspension was combined with 50 microliters of 0.04% w/v trypan blue (Sigma, St. Louis, Mo.) and the viable cell number, was estimated using a hemocytometer. Cells were then washed three times in supplement free-Leibovitz's L-15 medium (Invitrogen, Carlsbad, Calif.). Cells were then suspended at a concentration of 200,000 cells in 25 microliters of RAD-16 (3DM Inc., Cambridge, Mass.) which was buffered and made isotonic as per manufacturer's recommendations. One hundred microliters of supplement free Leibovitz's L-15 medium was added above the cell/matrix suspension to keep it wet till use. These cell/matrix cultures were maintained under standard atmospheric conditions until transplantation occurred. At the point of transplantation the excess medium was removed.

Animals and Surgery. Long Evans female rats (220-240 gram body weight) were used. Under intraperitoneal tribromoethanol anesthesia (20 milligram/100 grams body weight), the optic nerve was exposed, and the optic sheath was incised intraorbitally at approximately 2 millimeters from the optic disc, the nerve was lifted from the sheath to allow complete transsection with fine scissors (LI, Y. et al., "*Transplanted Olfactory Ensheathing Cells Promote Regeneration Of Cut Adult at Optic Nerve Axons,*"*J. of Neuro.,* 2003; 23(21):7783-7788.). The completeness of transsection was confirmed by visually observing complete separation of the proximal and distal stumps. The control group consisted of lesioned rats without transplants. In transplant rats cultured postpartum cells seeded in RAD-16 were inserted between the proximal and distal stumps using a pair of microforceps. Approximately 75,000 cells in RAD-16 were implanted into the severed optic nerve. Cell/matrix was smeared into the severed cut using a pair of fine microforceps. The severed optic nerve sheath was closed with 10/0 black monofilament nylon (Ethicon, Inc., Edinburgh, UK). Thus, the gap was closed by drawing the cut proximal and distal ends of the nerve in proximity with each other.

After cell injections were performed, animals were injected with dexamethasone (2 milligrams/kilogram) for 10 days post transplantation. For the duration of the study, animals were maintained on oral cyclosporine A (210 milligrams/liter of drinking water; resulting blood concentration: 250-300 micrograms/liter) (Bedford Labs, Bedford, Ohio) from 2 days pre-transplantation until end of the study. Food and water were available ad libitum. Animals were sacrificed at either 30 or 60 days posttransplantation.

CTB Application. Three days before animals were sacrificed, under anesthesia, a glass micropipette with a 30-50 millimeter tip was inserted tangentially through the sclera behind the lens, and two 4-5 microliter aliquots of a 1% retrograde tracer-cholera toxin B (CTB) aqueous solution (List Biologic, Campbell, Calif.) was injected into the vitreous. Animals were perfused with fixative and optic nerves were collected in the same fixative for 1 hour. The optic nerves were transferred into sucrose overnight. Twenty micrometer cryostat sections were incubated in 0.1 molar glycine for 30 minutes and blocked in a PBS solution containing 2.5% bovine serum albumin (BSA) (Boeringer Mannheim, Mannheim, Germany) and 0.5% triton X-100 (Sigma, St. Louis, Mo.), followed by a solution containing goat anti-CTB antibody (List Biologic, Campbell, Calif.) diluted 1:4000 in a PBS containing 2% normal rabbit serum (NRS) (Invitrogen, Carlsbad, Calif.), 2.5% BSA, and 2% Triton X-100 (Sigma, St. Louis, Mo.) in PBS, and incubated in biotinylated rabbit anti-goat IgG antibody (Vector Laboratories, Burlinghame, Calif.) diluted 1:200 in 2% Triton-X100 in PBS for 2 hours at room temperature. This was followed by staining in 1:200 streptavidin-green (Alexa Flour 438; Molecular Probes, Eugene, Oreg.) in PBS for 2 hours at room temperature. Stained sections were then washed in PBS and counterstained with propidium iodide for confocal microscopy.

Histology Preparation. Briefly, 5 days after CTB injection, rats were perfused with 4% paraformaldehyde. Rats were given 4 cubic centimeters of urethane and were then perfused with PBS (0.1 molar) then with 4% Para formaldehyde. The spinal cord was cut and the bone removed from the head to expose the colliculus. The colliculus was then removed and placed in 4% paraformaldehyde. The eye was removed by cutting around the outside of the eye and going as far back as possible. Care was given not to cut the optic nerve that lies on the underside of the eye. The eye was removed and the muscles were cut exposing the optic nerve this was then placed in 4% paraformaldehyde.

Results

Lesions alone. One month after retrotubular section of the optic nerve, a number of CTB-labeled axons were identified in the nerve segment attached to the retina. In the 200 micrometers nearest the cut, axons were seen to emit a number of collaterals at right angles to the main axis and terminate as a neuromatous tangle at the cut surface. In this cut between the proximal and distal stumps, the gap was observed to be progressively bridged by a 2-3 millimeter segment of vascularized connective tissue; however, no axons were seen to advance into this bridged area. Thus, in animals that received lesion alone no axonal growth was observed to reach the distal stump.

RAD-16 transplantation. Following transplantation of RAD-16 into the cut, visible ingrowth of vascularized connective tissue was observed. However, no axonal in growth was observed between the proximal and distal stumps. The results demonstrate that application of RAD-16 alone is not sufficient for inducing axonal regeneration in this situation.

Transplantation of postpartum-derived cells. Transplantation of postpartum-derived cells into the severed optic nerve stimulated optic nerve regrowth. Some regrowth was also observed in conditions in which fibroblast cells were implanted, although this was minimal as compared with the regrowth observed with the transplanted placenta-derived cells. Optic nerve regrowth was observed in 4/5 animals transplanted with placenta-derived cells, 3/6 animals transplanted with adult dermal fibroblasts and in 1/4 animals transplanted with umbilicus-derived cells. In situations where regrowth was observed, CTB labeling confirmed regeneration of retinal ganglion cell axons, which were demonstrated to penetrate through the transplant area. GFAP labeling was also performed to determine the level of glial scarring. The GFAP expression was intensified at the proximal stump with some immunostaining being observed through the reinervated graft.

Summary. These results demonstrate that transplanted human adult postpartum-derived cells are able to stimulate and guide regeneration of cut retinal ganglion cell axons.

References for Example 17
1) Zeng, B Y, Anderson, P N, Campbell, G, Lieberman, A R (1995) *J. Anat.* 186:495-508.
2) Villegas-Perez, M P, Vidal-Sanz, M, Bray, G M, Aguayo, A J (1988) *J. Neurosci.* 8:265-280.
3) Yip, H K, So, K F (2000) *Prog. Retin. Eye Res.* 19:559-575.
4) Fischer, D, Heiduschka, P, Thanos, S. (2001) *Exp. Neurol.* 172:257-272.
5) Ramon-Cueto, A, Cordero, M I, Santos-Benito, F F, Avila, J. (2000) *Neuron* 25:425-435.

EXAMPLE 18

Effect of PPDC Treatment on Transient Middle Cerebral Artery Occlusion Stroke

Postpartum-derived cells were evaluated in rats subjected to two-hour middle cerebral artery occlusion (MCAo). Behavioral tests for functional recovery were assessed at various time points and compared with vehicle and mesenchymal stem cell controls. Histology was performed at sacrifice to evaluate improvements and the tissue and cellular level.

Materials and Methods

Cell preparation and transplantation. Postpartum umbilicus-derived cells and human mesenchymal stem cells (Cambrex, PT2501) were cultured in-house before shipping to the site of the study, where they were thawed and processed on the day of transplantation. Cells were thawed in a 37° C. water bath, washed with 10 mL PBS in a 15 mL tube and centrifuged at 1000 rpm for 5 minutes at 4° C. The supernatant was discarded and cells resuspended in PBS. Cells were kept on ice prior to implantation, and viability determined by Trypan blue staining. In this study cell viability averaged 80% for PPDCs and 92% for MSCs.

At 1 day post-ischemia, randomly selected animals underwent cell transplantation. Animals were anesthetized with 3.5% halothane in N2O:O2 (2:1) and maintained at 0.5% halothane via a facemask. Each experimental group received cells suspended in 2 ml PBS or PBS alone administered via tail vein injection (27G1/2, B-D Precision Glide). The four groups (N=8/group) were 1 million PPDCs (U1), 3 million PPDCs (U3), 3 million MSCs (MSC), and PBS vehicle control. Immunosuppressants were not applied.

Temporal Middle Cerebral Artery Occlusion. Middle cerebral artery occlusion (MCAo) was induced in two- to three-month old Wistar rats (male, 270 to 300 g) using a modified method of intraluminal vascular occlusion (Chen et al., 1992). Briefly, rats were anesthetized with 3.5% halothane in N2O:O2 (2:1) and maintained at 0.5% halothane via a facemask. The right common carotid artery, external carotid artery and internal carotid artery were exposed. A length of 3-0 monofilament nylon suture, varying between 18.5 to 19.5 mm, depending on the animal weight, with its tip rounded by heating near a flame, was advanced from the external carotid artery into the lumen of the internal carotid artery until it blocked the origin of the MCA. Two hours after MCAo, reperfusion was performed by withdrawal of the suture until the tip cleared the internal carotid artery.

Neurological functional tests. Four behavioral tests were performed before MCAo (baseline), one day after MCAo, and weekly thereafter by an investigator who was blinded to the experimental groups.

Modified neurological severity score (mNSS) is a composite of motor, sensory, balance and reflex tests (Chen et al, 2001). Neurological function was graded on a scale of 0 to 18 (normal score 0; maximal deficit score 18) with one point awarded for the exhibition of specific abnormal behavior or for lack of a tested reflex. A greater impairment of normal function resulted in a higher score.

In the foot-fault test, rats were tested for placement dysfunctions of forelimb (Zhang et al., 2002). Rats were placed on elevated hexagonal grids of different sizes. The total number of steps used to cross the grid was counted, and the total number of foot faults for each forelimb was recorded. It is well established that in animals with MCAo, the impaired (contralateral) limbs faulted more often than non-impaired limbs.

The adhesive removal patch test requires the use of adhesive-backed paper dots of equal size (113.1 mm2) as bilateral tactile stimuli on the distal-radial region of each forelimb (Schallert et al., 1997). Prior to surgery rats were trained for 3 days to remove the adhesive. Once the rats were able to remove the adhesive dots within 10 seconds, they were subjected to MCAo. Post-MCAo, the time to remove each stimulus from both forelimbs was recorded on 3 trials per day. Individual trials were separated by at least 5 min.

The corner test measures sensory and motor functions and is more sensitive for long-term sensory and motor deficits (Zhang et al., 2002). A rat was placed between two boards (dimensions of 30×20×1 cm3) attached at 30° with a small opening along the joint to encourage entry into the corner. The rat was placed facing the corner such that both sides of the vibrissae were stimulated together when it entered deep into the corner. The rat would rear forward and upward, then turn back to face the open end. Healthy uninjured rats would turn either left or right; in contrast MCAo-injured rats preferentially turned toward the non-impaired side. The number of turns in one versus the other direction was recorded from ten trials for each test, and the percentage of turns used as the corner test score.

Brain section preparation. To identify cell proliferation, all rats received intraperitoneal injections of bromodeoxyuridine (BrdU, 50 mg/kg, Sigma, St, Louis Mo.) daily for 14 consecutive days after MCAo. Rat brains were fixed by transcardial perfusion with saline, followed by perfusion and immersion in 4% paraformaldehyde. Using a rat brain matrix (Activational Systems Inc., Warren, Mich.), each forebrain was cut into 2-mm thick coronal blocks for a total of 7 blocks from bregma 5.2 mm to bregma −8.8 mm per animal (Paxinos and Watson 1986 The rat brain in stereotaxic coordinated, $2^{nd}$ Ed. Sydney; Orlando. Academic Press). The tissues were embedded in paraffin, and a series of 6 μm-thick slides was cut.

Measurement of infarct area. One of each coronal paraffin slides (6 μm thick) from seven blocks was stained with hematoxylin and eosin (H&E). Seven brain slides were traced using the Global Lab Image analysis system (Data Translation, Malboro, Mass.). The indirect lesion area, in which the intact area of the ipsilateral hemisphere was subtracted from the area of the contralateral hemisphere, was calculated (Swanson et al., 1990). The lesion volume is presented as a volume percentage of the lesion compared to the contralateral hemisphere.

Immunohistochemical Assessment. A standard paraffin block was obtained from the center of the lesion, corresponding to coronal coordinates for bregma −1~1 mm. A series of 6-μm-thick sections were cut from this block for analysis by light and fluorescent microscopy (Olympus, BH-2). To identify grafted human cells, a mouse anti-human nuclear monoclonal antibody (mAb 1281, Chemicon International, Inc) was used at a titer of 1:300. To distinguish proliferating cells, a mouse antibody (Dako) was applied at a titer of 1:100. Double staining was performed to visualize cellular co-localization of human nuclei or BrdU with cell type-specific markers (NeuN for neurons, dilution 1:500; glial fibrillary acidic protein, GFAP, for astrocytes, dilution 1:5000). Moreover, antibodies against von Willebrand factor (vWF, 1:400, Dako) and synaptophysin (1:500, Chemicon) were used to identify vessels and synapses, respectively.

Apoptotic cell staining. The terminal deoxynucleotidyl transferase (TdT) -mediated dUTP-biotin nick end labeling (TUNEL) method (in situ Apoptosis Detection Kit, Chemicon) was used to assess in situ apoptotic detection (Li et al., 1998, Li et al., 1995). The TUNEL method is based on the specific binding of TdT to 3'-OH ends of DNA and the ensuing synthesis of polydeoxynucleotide polymer cells. Staining was performed according to the manufacturer's protocol.

Cell Quantification. To quantify donor human cells and apoptotic cells, the number of apoptotic cells in ipsilateral hemisphere per section was counted. For measurement of vascular and synapse density, 8 fields of view from the ischemic penumbra were digitized using either a 40× objective via the MCID computer imaging analysis system. The number of vessels as well as the positive area of synaptophysin in the ischemic boundary zone (IBZ) were counted throughout each field of view.

Results

Neurological Functional Outcome. Severe behavioral deficits were evident in all animals 1 day post-stroke. All rats subjected to MCAo showed progressive behavioral recovery over time to 28 days post-MCAo (see Table 18-1). No significant differences in behavioral tests were detected amongst groups before MCAo in all the functional tests. At 28 days post-MCAo, mNSS injury had progressed from moderate to mild: statistically significant improvement was observed in mNSS in cell-treated groups compared to PBS control (p=0.01 for U1, p=0.1 for U3, and p=0.02 for MSC). The percentage of recorded foot faults also decreased in a statistically significant manner in rats receiving cell therapies (p=0.02 for U1, p=0.06 for U3, and p=0.01 for MSC).

No significant differences were observed in the adhesive removal as well as corner tests. The weight of animals in all groups showed a similar trend of loss immediately after MCAo followed by steady gain within the first week.

TABLE 18-1

| | Neurological functional outcome | | | | | | | |
|---|---|---|---|---|---|---|---|---|
| | PBS | | MSC | | U1 | | U3 | |
| Time (days) | Mean | S.E. | Mean | S.E. | Mean | S.E. | Mean | S.E. |
| mNSS | | | | | | | | |
| 2 | 11.25 | 0.31 | 11.00 | 0.57 | 10.50 | 0.19 | 10.63 | 0.46 |
| 7 | 8.29 | 0.36 | 7.63 | 0.50 | 7.75 | 0.16 | 7.63 | 0.42 |
| 14 | 7.14 | 0.34 | 6.50 | 0.33 | 6.75 | 0.16 | 6.63 | 0.42 |
| 21 | 5.86 | 0.26 | 5.50 | 0.33 | 5.63 | 0.18 | 5.63 | 0.42 |
| 28 | 5.71 | 0.29 | 4.50 | 0.33 | 4.50 | 0.27 | 4.75 | 0.45 |
| P-value (vs. PBS) | | | 0.02 | | 0.01 | | 0.10 | |
| Footfault | | | | | | | | |
| 2 | 38.38 | 1.66 | 37.00 | 2.39 | 36.50 | 1.18 | 37.13 | 1.68 |
| 7 | 31.43 | 1.99 | 28.88 | 1.92 | 31.13 | 1.48 | 29.50 | 1.99 |
| 14 | 25.00 | 1.86 | 20.63 | 1.41 | 25.25 | 1.37 | 22.63 | 1.57 |
| 21 | 20.00 | 1.23 | 15.63 | 1.27 | 19.13 | 1.44 | 16.63 | 1.43 |
| 28 | 16.14 | 1.30 | 11.50 | 0.80 | 11.50 | 1.02 | 12.63 | 1.05 |
| P-value (vs. PBS) | | | 0.01 | | 0.02 | | 0.06 | |
| Corner | | | | | | | | |
| 2 | 9.38 | 0.42 | 9.88 | 0.13 | 9.63 | 0.26 | 9.50 | 0.33 |
| 7 | 9.29 | 0.36 | 9.13 | 0.30 | 9.00 | 0.42 | 9.25 | 0.49 |
| 14 | 8.86 | 0.55 | 8.50 | 0.33 | 8.13 | 0.35 | 9.13 | 0.58 |
| 21 | 7.86 | 0.59 | 8.00 | 0.27 | 7.38 | 0.32 | 8.50 | 0.60 |
| 28 | 7.43 | 0.61 | 7.50 | 0.33 | 6.63 | 0.38 | 7.75 | 0.65 |
| P-value (vs. PBS) | | | 0.92 | | 0.29 | | 0.72 | |
| Adhesive | | | | | | | | |
| 2 | 108.38 | 7.78 | 110.63 | 6.97 | 103.50 | 8.49 | 107.88 | 7.98 |
| 7 | 89.14 | 15.19 | 102.63 | 12.02 | 69.25 | 10.57 | 75.50 | 14.07 |
| 14 | 75.43 | 15.15 | 79.88 | 12.76 | 54.38 | 10.71 | 70.50 | 12.95 |
| 21 | 64.43 | 15.76 | 69.13 | 11.64 | 43.63 | 9.37 | 52.88 | 13.12 |
| 28 | 38.29 | 9.76 | 45.50 | 9.36 | 32.75 | 7.30 | 45.63 | 13.50 |
| P-value (vs. PBS) | | | 0.60 | | 0.66 | | 0.67 | |
| Weight | | | | | | | | |
| 0 | 296.38 | 4.71 | 296.50 | 6.20 | 292.00 | 4.50 | 300.75 | 6.05 |
| 2 | 259.63 | 6.60 | 258.63 | 8.93 | 258.88 | 4.07 | 261.88 | 9.30 |
| 7 | 272.14 | 13.77 | 283.00 | 15.42 | 281.75 | 8.00 | 264.63 | 18.68 |
| 14 | 311.57 | 11.15 | 319.13 | 14.02 | 315.50 | 8.50 | 292.75 | 22.33 |
| 21 | 348.00 | 12.54 | 356.00 | 13.24 | 344.00 | 11.47 | 316.38 | 26.13 |
| 28 | 376.86 | 10.96 | 384.75 | 12.97 | 373.25 | 13.91 | 342.75 | 28.94 |
| P-value (vs. PBS) | | | 0.65 | | 0.84 | | 0.30 | |

Infarct volume. As shown in Table 18-2, no significant differences of the percent lesion volumes to the contralateral hemisphere were detected among all four groups.

TABLE 18-2

| Histology results. | | | | |
|---|---|---|---|---|
| | PBS | MSC | U1 | U3 |
| Lesion Volume | | | | |
| Mean | 0.35 | 0.35 | 0.32 | 0.33 |
| S.E. | 0.04 | 0.04 | 0.05 | 0.07 |
| Synapotphysin | | | | |
| Mean | 0.19 | 0.26 | 0.22 | 0.23 |
| S.E. | 0.02 | 0.02 | 0.02 | 0.02 |
| Number of vWF positive vessels/40x field | | | | |
| Mean | 15.54 | 18.24 | 19.35 | 18.82 |
| S.E. | 0.57 | 0.58 | 0.54 | 0.60 |
| vWF positive vessels density per 40x field | | | | |
| Mean | 2.76 | 3.75 | 3.15 | 2.97 |
| S.E. | 0.29 | 0.25 | 0.24 | 0.32 |
| Apoptosis | | | | |
| Mean | 90.86 | 55.38 | 44.88 | 56.38 |
| S.E. | 12.29 | 8.01 | 6.58 | 5.59 |
| BrdU/Contralateral | | | | |
| Mean | 21.29 | 24.13 | 20.75 | 23.50 |
| S.E. | 2.18 | 1.89 | 2.80 | 3.45 |
| BrdU/Ipsilateral | | | | |
| Mean | 26.57 | 43.13 | 28.50 | 43.88 |
| S.E. | 3.12 | 5.44 | 4.28 | 8.22 |
| MAB1281 | | | | |
| Mean | | 73.86 | 45.50 | 58.13 |
| S.E. | | 7.36 | 8.57 | 7.78 |

Histology. Donor cells in the brain. Within the brain tissue, human cells were characterized by round-to-oval nuclei identified by the human specific antibody mAb1281. Donor cells survived and were distributed throughout the ischemic damaged brain of recipient rats. Double immunohistochemical staining of brain sections revealed approximately 1% of human mAb1281-positive cells to be reactive for the neuronal marker, NeuN, and for the astrocytic marker, GFAP (Table 18-2).

Neurogenesis in the ischemic brain. BrdU, a thymidine analog, can be incorporated into cells during S phase, and BrdU-positive cells in the subventricular zone (SVZ) are considered to be progenitor cells undergoing proliferation. In this study, rats treated with higher doses of cells showed an increase in proliferation in the SVZ in the ipsilateral hemisphere. Progenitor cells in the SVZ can remain in either a proliferating state or they can exit the cell cycle and differentiate into functional brain cells. Since the latter property of neural progenitor cells is tied in with brain self-repair after injury or disease, double staining for BrdU and GFAP or NeuN was performed and showed approximately 5% BrdU-positive cells expressed GFAP or NeuN (Table 18-2).

Angiogenesis. The presence of enlarged, thin-walled vessels in the ischemic boundary zone (IBZ) is indicative of angiogenesis (Zhang et al. (2002) *J. Cereb. Blood Flow Metab.* 22:379-92). Cell treatments were observed to increase the number of vessels by 17 to 25% in the IBZ compared to PBS vehicle control (Table 18-2).

Synaptogenesis. Synaptophysin, a pre-synaptic vesicle protein, is used as an indicator of synaptogenesis (Ujike et al. (2002) Ann. Ny Acad. Sci. 965:55-67). In this study, an increase in synaptophysin expression in the IBZ was observed with cell treatments (Table 18-2).

Reduction of cell apoptosis and death. TUNEL staining showed apoptotic cells with typical dark brown, rounded or oval apoptotic bodies were present throughout the damaged tissue, although the vast majority of apoptosis was located in the IBZ or SVZ. The number of apoptotic cells in the ipsilateral hemisphere was reduced by 51% in rats receiving U1 cells and by 38% in U3- and MSC-treated rats ($P<0.01$ for U1, $P<0.05$ for MSC and U3, compared to PBS control) (Table 18-2).

Summary

PPDCs were demonstrated to have utility for the treatment of strokes. Cell therapy led to improved neurological functions evidenced through higher motor-sensory scores. PPDCs administered into the tail vein after MCAo entered the ischemic brain tissue and survived at least 28 days after cell injection without immunosuppressants. The positive effects became statistically significant at 21 days post-MCAo, persisting to the last day of observation (28 days post-surgery). Significantly more microvessels existed in the ipsilateral hemisphere of rats treated with PPDC cells (compared to control animal, $P<0.05$). PPDC treatment also significantly reduced the number of apoptotic cells in the ipsilateral hemisphere at 28 days after MCAo.

References for Example 18
1. Chen, H., M. Chopp, Z. G. Zhang, and J. H. Garcia. 1992. J Cereb Blood Flow Metab 12:621-8.
2. Chen, J., Y. Li, L. Wang, Z. Zhang, D. Lu, M. Lu, and M. Chopp. 2001. Stroke 32:1005-11.
3. Guide for the Care and Use of Laboratory Animals, 7th edition.
4. Li, Y., C. Powers, N. Jiang, and M. Chopp. 1998. J Neurol Sci 156:119-32.
5. Li, Y., V. G. Sharov, N. Jiang, C. Zaloga, H. N. Sabbah, and M. Chopp. 1995. Am J Pathol 146:1045-51.
6. Paxinos, G., and C. Watson. 1986. The rat brain in stereotaxic coordinates, 2nd edition. Sydney; Orlando: Academic Press.
7. Schallert, T., D. A. Kozlowski, J. L. Humm, and R. R. Cocke. 1997. Adv Neurol 73:229-38.
8. Swanson, R. A., M. T. Morton, G. Tsao-Wu, R. A. Savalos, C. Davidson, and F. R. Sharp. 1990. J Cereb Blood Flow Metab 10:290-3.
9. Trenka-Benthin, S. (2005). Testicular lesion histology report and photomicrograph indexes.
10. Ujike, H., M. Takaki, M. Kodama, and S. Kuroda. 2002. Ann N Y Acad Sci 965:55-67.
11. Zhang, L., T. Schallert, Z. G. Zhang, Q. Jiang, P. Arniego, Q. Li, M. Lu, and M. Chopp. 2002a. J Neurosci Methods 117:207-14.
12. Zhang, Z. G., L. Zhang, W. Tsang, H. Soltanian-Zadeh, D. Morris, R. Zhang, A. Goussev, C. Powers, T. Yeich, and M. Chopp. 2002b. J Cereb Blood Flow Metab 22:379-92.

EXAMPLE 19

Endothelial Network Formation Assay

Angiogenesis, or the formation of new vasculature, is necessary for the growth of new tissue. Induction of angiogenesis is an important therapeutic goal in many pathological conditions. The present study was aimed at identifying potential angiogenic activity of the postpartum-derived cells in in vitro assays. The study followed a well-established method of seeding endothelial cells onto a culture plate coated with MATRIGEL (BD Discovery Labware, Bedford, Mass.), a basement membrane extract (Nicosia and Ottinetti (1990) *In Vitro Cell Dev. Biol.* 26(2):119-28). Treating endothelial cells on MATRIGEL (BD Discovery Labware, Bedford, Mass.) with angiogenic factors will stimulate the cells to form a network that is similar to capillaries. This is a common in vitro assay for testing stimulators and inhibitors of blood vessel formation (Ito et al. (1996) *Int. J. Cancer* 67(1):148-52). The present studies made use of a co-culture system with the postpartum-derived cells seeded onto culture well inserts. These permeable inserts allow for the passive exchange of media components between the endothelial and the postpartum-derived cell culture media.

Methods & Materials

Cell Culture.

Postpartum tissue-derived cells. Human umbilical cords and placenta were received and cells were isolated as previously described (Example 1). Cells were cultured in Growth medium (Dulbecco's Modified Essential Media (DMEM; Invitrogen, Carlsbad, Calif.), 15% (v/v) fetal bovine serum (Hyclone, Logan Utah), 100 Units/milliliter penicillin, 100 microgram/milliliter streptomycin (Invitrogen), 0.001% (v/v) 2-mercaptoethanol (Sigma, St. Louis, Mo.)) on gelatin-coated tissue culture plastic flasks. The cultures were incubated at 37° C. with 5% $CO_2$. Cells used for experiments were between passages 4 and 12.

Actively growing postpartum cells were trypsinized, counted, and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium at 37° C. under standard growth conditions.

Human mesenchymal stem cells (hMSC). hMSCs were purchased from Cambrex (Walkersville, Md.) and cultured in MSCGM (Cambrex). The cultures were incubated under standard growth conditions.

Actively growing MSCs were trypsinized and counted and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium under standard growth conditions.

Human umbilical vein endothelial cells (HUVEC). HUVEC were obtained from Cambrex (Walkersville, Md.). Cells were grown in separate cultures in either EBM or EGM endothelial cell media (Cambrex). Cells were grown on standard tissue-cultured plastic under standard growth conditions. Cells used in the assay were between passages 4 and 10.

Human coronary artery endothelial cells (HCAEC). HCAEC were purchased from Cambrex Incorporated (Walkersville, Md.). These cells were also maintained in separate cultures in either the EBM or EGM media formulations. Cells were grown on standard tissue cultured plastic under standard growth conditions. Cells used for experiments were between passages 4 and 8.

Endothelial Network Formation (MATRIGEL) assays. Culture plates were coated with MATRIGEL (BD Discovery Labware, Bedford, Mass.) according to manufacturer's specifications. Briefly, MATRIGEL™ (BD Discovery Labware, Bedford, Mass.) was thawed at 4° C. and approximately 250 microliters were aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth medium with 2% FBS by centrifugation, resuspension, and aspiration of the supernatant. Cells were seeded onto the coated wells at 20,000 cells per well in approximately 0.5 milliliter Growth medium with 2% (v/v) FBS. Cells were then incubated for approximately 30 minutes to allow cells to settle.

Endothelial cell cultures were then treated with either 10 nanomolar human bFGF (Peprotech, Rocky Hill, N.J.) or 10 nanomolar human VEGF (Peprotech, Rocky Hill, N.J.) to serve as a positive control for endothelial cell response. Transwell inserts seeded with postpartum-derived cells were added to appropriate wells with Growth medium with 2% FBS in the insert chamber. Cultures were incubated at 37° C. with 5% $CO_2$ for approximately 24 hours. The well plate was removed from the incubator, and images of the endothelial cell cultures were collected with an Olympus inverted microscope (Olympus, Melville, N.Y.).

Results

In a co-culture system with placenta-derived cells or with umbilical cord-derived cells, HUVEC form cell networks (data not shown). HUVEC cells form limited cell networks in co-culture experiments with hMSCs and with 10 nanomolar bFGF (data not shown). HUVEC cells without any treatment showed very little or no network formation (data not shown). These results suggest that the postpartum-derived cells release angiogenic factors that stimulate the HUVEC.

In a co-culture system with placenta-derived cells or with umbilical cord-derived cells, CAECs form cell networks (data not shown).

Table 19-1 shows levels of known angiogenic factors released by the postpartum-derived cells in Growth medium. Postpartum-derived cells were seeded onto inserts as described above. The cells were cultured at 37° C. in atmospheric oxygen for 48 hours on the inserts and then switched to a 2% FBS media and returned at 37° C. for 24 hours. Media was removed, immediately frozen and stored at −80° C., and analyzed by the SearchLight multiplex ELISA assay (Pierce Chemical Company, Rockford, Ill.). Results shown are the averages of duplicate measurements. The results show that the postpartum-derived cells do not release detectable levels of platelet-derived growth factor-bb (PDGF-bb) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 19-1

Potential angiogenic factors released from postpartum-derived cells. Postpartum-derived cells were cultured in 24 hours in media with 2% FBS in atmospheric oxygen. Media was removed and assayed by the SearchLight multiplex ELISA assay (Pierce). Results are the means of a duplicate analysis. Values are concentrations in the media reported in picograms per milliliter of culture media.

|  | TIMP1 (pg/ml) | ANG2 (pg/ml) | PDGFBB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 91655.3 | 175.5 | <2.0 | 275.5 | 3.0 | 58.3 | 7.5 | 644.6 | <1.2 |
| Plac (P11) | 1592832.4 | 28.1 | <2.0 | 1273.1 | 193.3 | 5960.3 | 34.8 | 12361.1 | 1.7 |
| Umb cord (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Plac: placenta derived cells;
Umb cord: Umbilical cord derived cells

Table 19-2 shows levels of known angiogenic factors released by the postpartum-derived cells. Postpartum-derived cells were seeded onto inserts as described above. The cells were cultured in Growth medium at 5% oxygen for 48 hours on the inserts and then switched to a 2% FBS medium and returned to 5% $O_2$ incubation for 24 hours. Media was removed, immediately frozen, and stored at −80° C., and analyzed by the SearchLight multiplex ELISA assay (Pierce Chemical Company, Rockford, Ill.). Results shown are the averages of duplicate measurements. The results show that the postpartum-derived cells do not release detectable levels of platelet-derived growth factor-bb (PDGF-BB) or heparin-binding epidermal growth factor (HBEGF). The cells do release measurable quantities of tissue inhibitor of metalloprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

Preparation of Lyophilized Samples. Three lots of cells (PPDC Lots L040405, L052505, L050505) were prepared for eventual lyophilization by immersing into liquid nitrogen (LN2) for 60 seconds. The tubes were then removed from LN2 and immediately immersed in a 37° C. water bath for 60 seconds or until thawed (3 minute maximum incubation time). This process was repeated two more times. The freeze-thawed samples were centrifuged for 10 minutes at 13,000 rcf at 4° C. and placed on ice. The supernatant fluid from each

TABLE 19-2

Potential angiogenic factors released from postpartum-derived cells. Postpartum-derived cells were cultured in 24 hours in media with 2% FBS in 5% oxygen. Media was removed and assayed by the SearchLight multiplex ELISA assay (Pierce). Results are the means of a duplicate analysis. Values are concentrations in the media reported in picograms per milliter of culture media.

| | TIMP1 (pg/ml) | ANG2 (pg/ml) | PDGF-BB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 72972.5 | 253.6 | <2.0 | 743.1 | 2.5 | 30.2 | 15.1 | 1495.1 | <1.2 |
| Plac (P11) | 458023.1 | 55.1 | <2.0 | 2562.2 | 114.2 | 2138.0 | 295.1 | 7521.3 | 1.8 |
| Umb cord (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

Plac: placenta derived cells;
Umb cord: Umbilical cord derived cells

Summary. The results of the present study show that postpartum-derived cells can stimulate both human umbilical vein and coronary artery endothelial cells to form networks in an in vitro MATRIGEL™ (BD Discovery Labware, Bedford, Mass.) assay. This effect is similar to that seen with known angiogenic factors in this assay system. These results suggest that the postpartum-derived cells are useful for stimulating angiogenesis in vivo.

EXAMPLE 20

RayBio and BD Powerblot Cytokine Arrays

RayBio® Human Cytokine Antibody Array C Series 1000 was used to analyze the expression of 120 proteins in postpartum-derived cells and lysates. This analysis provided a characterization of the PPDCs and identified an expression spectrum of key trophic factors for these cells.

Materials and Methods

Cell Growth and Harvest. Umbilicus-derived cells were seeded at 5,000 cells per cm squared in gelatin-coated flasks with growth media and expanded for 3 to 4 days (25,000 cells per cm squared target harvest density). Cells were harvested with trypsin, collected, and centrifuged at 300 rcf for 5 minutes. The trypsin/media was removed by aspiration and cells were washed three times with phosphate buffered saline (PBS).

Cell Wash and Aliquoting. After washing, the cells were re-suspended at 1.0E+07 cell/ml in PBS and delivered as 1 ml aliquots into 1.5 ml sterile siliconized micro-centrifuge tubes. The cells were centrifuged at 300 rcf for 5 minutes and the PBS was removed by aspiration. Cells were either lyzed and analyzed by the array, or lyzed and lyophilized for analysis.

tube was removed. To determine total protein content, lysate was diluted into PBS and the dilution was analyzed by Bradford assay.

For lyophilization, multiple 1.5 ml sterile cryovials labeled with lysate were loaded into an autoclaved and cooled heat transfer block. Aliquots of lysate supernatant fluid at defined total protein concentration were loaded into the cryovials. The heat block containing uncapped cryovials were aseptically loaded into autoclaved un-used autoclave pouch. The pouch was loaded into the lyophilizer.

Test materials with applied lysate were loaded into a FTS Systems Dura-Stop MP Stoppering Tray Dryer and lyophilized using the following ramping program. All steps had a ramping rate of 2.5° C./minute and a 100-mT vacuum.

| Step | Shelf Temp (C.) | Hold Time (min) |
|---|---|---|
| a | −40 | 180 |
| b | −25 | 2160 |
| c | −15 | 180 |
| d | −5 | 180 |
| e | 5 | 120 |
| f | 20 | 120 |
| g | −20 | 60 |

Preparation of Cell Pellets. Frozen cell pellets (PPDC lots 063004B, 022803, 050604B, 072804, 120304, 071404C, 090304) were lysed using a 1:1 mix of RIPA buffer (50 mM Tris HCl, pH8, 150 mM NaCl, 1% NP-40, 0.5% Sodium deoxycholate and 0.1% SDS) and cell lysis buffer provided in the RayBio cytokine array 1000.1 kit (Raybiotech Inc. Norcross, Ga.). Glass beads (Sigma, Mo.) were used to achieve complete cell lysis. Protein concentration was measured using the BCA protein assay kit (Pierce Biotechnology, Inc. Rockford, Ill.).

RayBio Array Analysis. RayBio arrays VI and VII, which constitute the array 1000.1, were probed overnight with equal amounts of protein from each sample. The remaining protocol was followed as per the manufacturer's guidelines. The spots on the membrane were qualitatively analyzed to determine proteins of interest. For quantitative comparison between samples, these spots could be analyzed by densitometry and changes in expression confirmed by ELISA.

Results

A total of ten different PPDC populations were analyzed. Forty-eight proteins were qualitatively identified and listed in Table 20-1. Some proteins were expressed at relatively high concentrations in all samples tested while others were expressed in certain samples.

TABLE 20-1

Qualitatively identified PPDC proteins.

| | Trophic Factor | Abbreviation |
|---|---|---|
| 1 | Brain Derived Neurotrophic Factor | BDNF |
| 2 | Basic fibroblast growth factor | bFGF |
| 3 | Bone Morphogenetic Protein-4 | BMP-4 |
| 4 | Bone Morphogenetic Protein-6 | BMP-6 |
| 5 | MPIF-1 | CK b 8-1 |
| 6 | Ciliary Neurotrophic Factor | CNTF |
| 7 | CCL27, (cutaneous T cell attracting chemokine) | CTACK |
| 8 | Epidermal Growth Factor | EGF |
| 9 | CCL26 | Eotaxin-3 |
| 10 | Fas Antigen | Fas/TNFRSF6 |
| 11 | Fibroblast Growth Factor-6 | FGF-6 |
| 12 | FMS related Tyrosine kinase 3 | FIT-3 ligand |
| 13 | CX3C chemokine | Fractalkine |
| 14 | Granulocyte colony stimulating factor | GCSF |
| 15 | Glucocorticoid Induced TNF receptor superfamily-related protein | GITR ligand |
| 16 | Granulocyte-Macrophage Colony Stimulating Factor | GM-CSF |
| 17 | Hepatocyte Growth Factor | HGF |
| 18 | CCL1 | I-309 |
| 19 | Intercellular adhesion molecules 1 | ICAM-1 |
| 20 | Insulin Like Growth Factor Binding Protein-1 | IGFBP-1 |
| 21 | Insulin Like Growth Factor Binding Protein-2 | IGFBP-2 |
| 22 | Insulin Like Growth Factor Binding Protein-3 | IGFBP-3 |
| 23 | Insulin Like Growth Factor Binding Protein-6 | IGFBP-6 |
| 24 | Interleukin-10 | IL-10 |
| 25 | Interleukin-13 | IL-13 |
| 26 | Interleukin-1a | IL-1a |
| 27 | Interleukin-1Ra | IL-1Ra |
| 28 | Interleukin-3 | IL-3 |
| 29 | Interleukin-5 | IL-5 |
| 30 | Interleukin-6 | IL-6 |
| 31 | Interleukin-7 | IL-7 |
| 32 | Interleukin-8 | IL-8 |
| 33 | IFN-inducible T cell chemoattractant | I-TAC |
| 34 | Monocyte Chemotactic Protien-1 | MCP-1 |
| 35 | Migration inhibitory factor | MIF |
| 36 | Macrophage inflammatory protein-1 | MIP-1a |
| 37 | oncostatin M | oncostatin M |
| 38 | Phosphatidylinositol glycan F | PIGF |
| 39 | soluble gp130-signal transducer chain | sgp130 |
| 40 | Transforming Growth Factor-B1 | TGF-b1 |
| 41 | Transforming Growth Factor-B3 | TGF-b3 |
| 42 | Thrombopoietin | Thrombopoietin |
| 43 | Tissue Inhibitor of metalloproteinase 2 | TIMP-2 |
| 44 | Tumor Necrosis Factor-alpha | TNF-a |
| 45 | Tumor Necrosis Factor-Beta | TNF-b |
| 46 | TNF-related apoptosis-inducing ligand-receptor3 | TRAIL-R3 |
| 47 | TNF-related apoptosis-inducing ligand-receptor4 | TRAIL-R4 |
| 48 | urokinase-type plasminogen activator receptor | uPAR |

Summary

The RayBio array confirms the expression of proteins previously identified by gene array and/or ELISA analyses. Various trophic factors beneficial for specific disease treatment have been identified. For instance, FGF, TGF-b, and GCSF were identified in PPDCs, and these growth factors have been previously identified with improvements in animal models of acute stroke and stroke recovery. In addition, BDNF, BMP-4, BMP-6, and TGF-b1, which are positively associated with Parkinson's disease, have been identified in PPDCs. All data presented are qualitatively assessed; quantitative analysis of the level of expression for proteins of interest is pending.

EXAMPLE 21

Effect of Variant PPDC Doses in Transient Middle Cerebral Artery Occlusion Stroke Postpartum cells were evaluated at different doses in rats subjected to 2-hour middle cerebral artery occlusion (MCAo). PPC treatments at varying doses: 0.3, 1, 3, and 10 million cells/dose-rat, were compared to PBS and mesenchymal stem cell controls in a 60-day study.

Materials and Methods

Cell Preparation. Postpartum-derived cells and human mesenchymal stem cells (Cambrex, PT2501) were cultured in-house before shipping to the site of study, where they were thawed and processed on the day of transplantation. Cells were thawed in a 37° C. water bath, washed with 10 mL PBS in a 15 mL tube and centrifuged at 1000 rpm for 5 minutes at 4° C. The supernatant was discarded and cells resuspended in PBS. Cells were kept on ice prior to implantation, and viability determined by Trypan blue staining. Cell viability averaged 85% for PPDC and MSCs.

At 1 day post-ischemia, randomly selected animals underwent cell transplantation. Animals were anesthetized with 3.5% halothane in $N_2O:O_2$ (2:1) and maintained at 0.5% halothane via a facemask. Each experimental group received cells suspended in 2 ml PBS or PBS alone administered via tail vein injection (27G1/2, B-D Precision Glide). The six groups (N=8/group) were 0.3, 1, 3, and 10 million PPCs, 3 million MSCs ("MSC"), and PBS vehicle control. Immunosuppressants were not applied.

Temporal Middle Cerebral Artery Occlusion. Middle cerebral artery occlusion (MCAo) was induced in rats using a modified method of intraluminal vascular occlusion. In brief, rats were anesthetized with 3.5% halothane in $N_2O:O_2$ (2:1) and maintained at 0.5% halothane via a facemask. The right common carotid artery, external carotid artery and internal carotid artery were exposed. A length of 3-0 monofilament nylon suture, varying between 18.5 to 19.5 mm depending on the animal weight, with its tip rounded by heating near a flame, was advanced from the external carotid artery into the lumen of the internal carotid artery until it blocked the origin of the MCA. Two hours after MCAo, reperfusion was performed by withdrawal of the suture until the tip cleared the internal carotid artery.

Neurological functional tests. Four behavioral tests were performed before MCAo (baseline), one day after MCAo, and on Days 7, 14, 21, 28, 35, 42, 56, and 60 by an investigator who was blinded to the experimental groups. The details of each test were as described in EXAMPLE 18.

Results

Neurological Functional Outcome. Severe behavioral deficits were evident in all animals 1 day post-stroke. All rats subjected to MCAo showed progressive behavioral recovery over time to 60 days post-MCAo. Animals receiving PPDC treatments showed a trend towards functional recovery in all tests. Overall the beneficial effects of cell therapy was sustained and increased over the duration of study.

Figure 2:
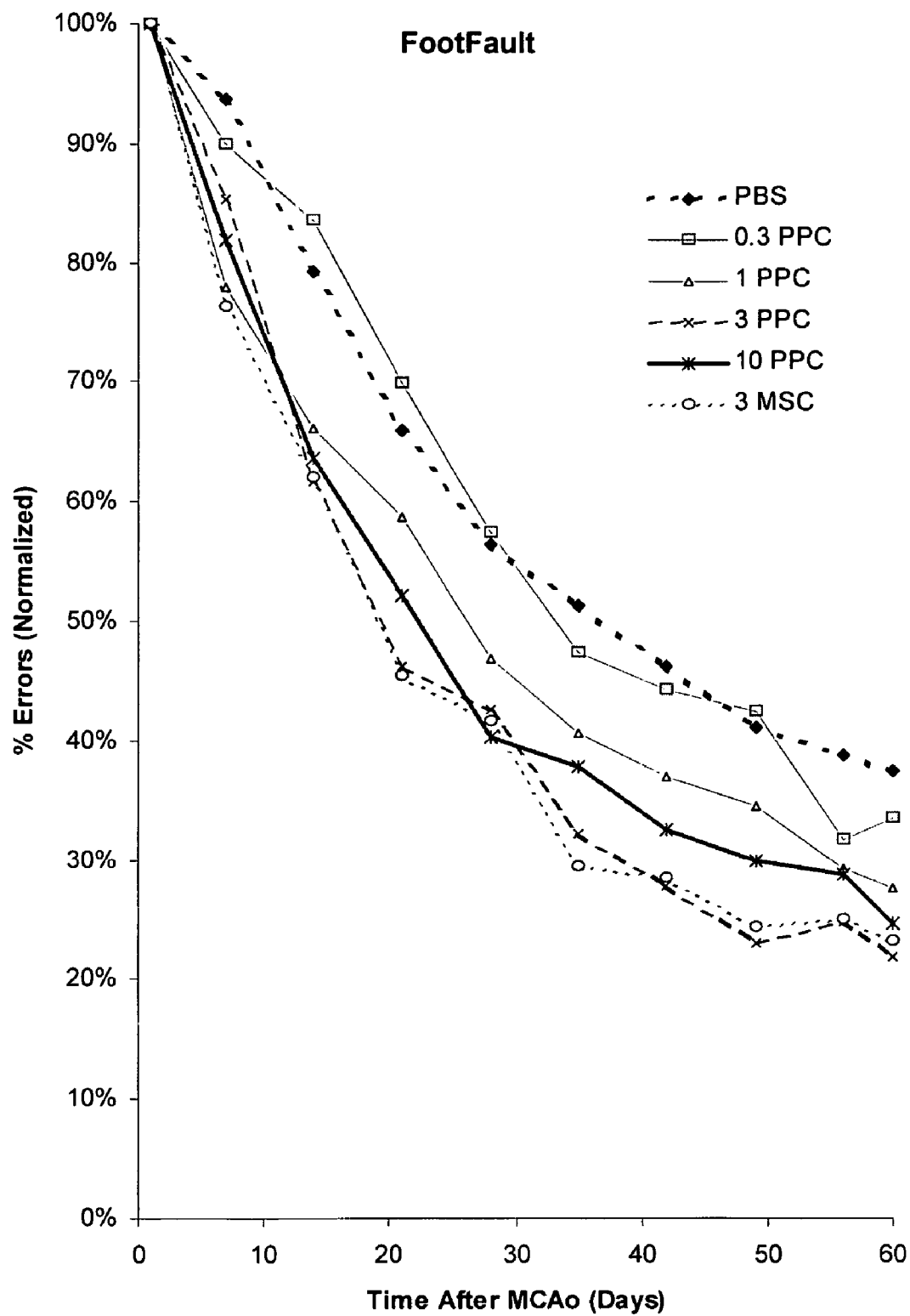
FIG. 2. Graph showing results of Foot-Fault Test following middle cerebral artery occlusion (MCAo) in rats (PPC=postpartum-derived cells; MSC=mesenchymal stem cells).
Figure 3:
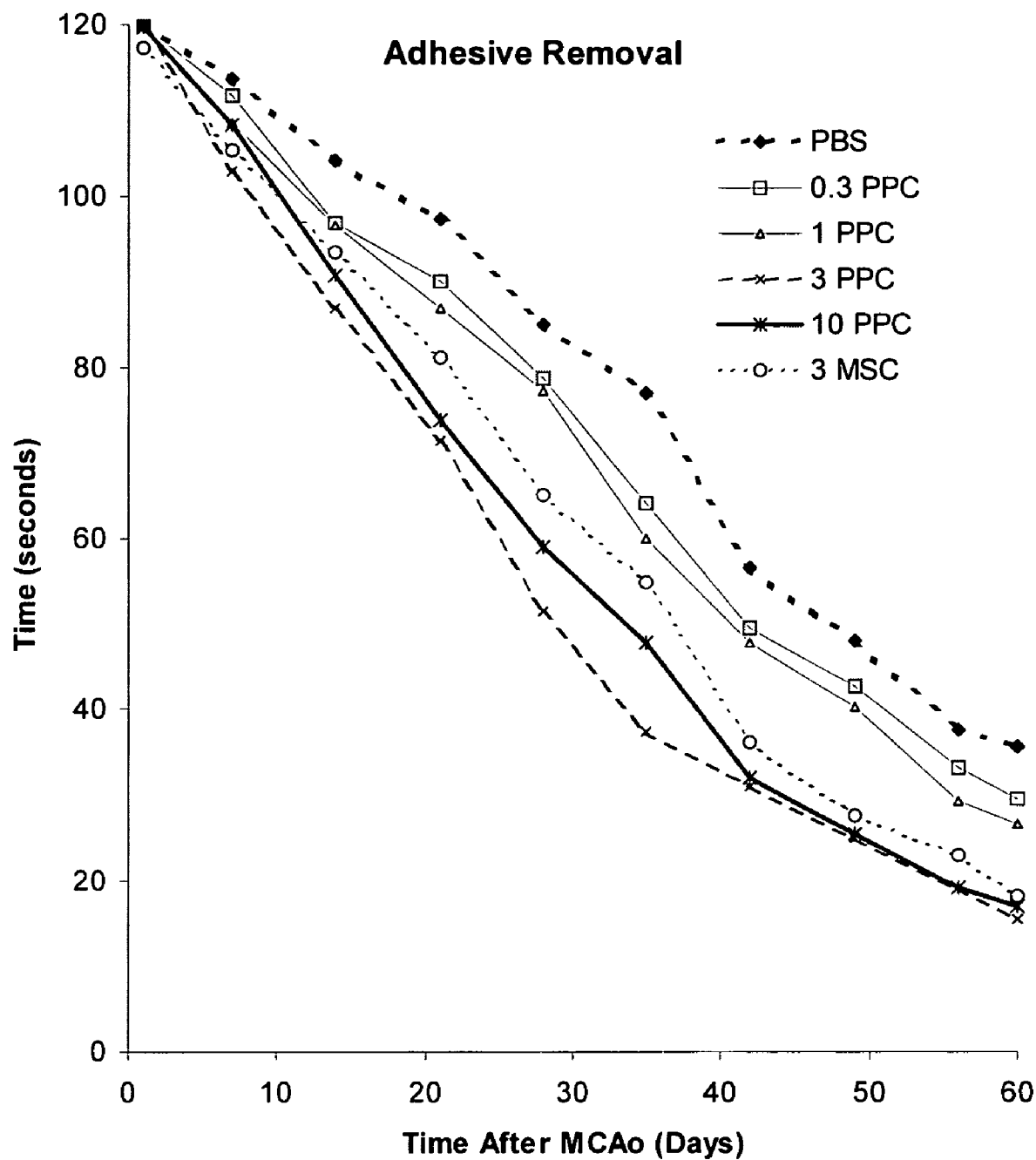
FIG. 3. Graph showing results of Adhesive Removal Test following middle cerebral artery occlusion (MCAo) in rats (PPC=postpartum-derived cells; MSC=mesenchymal stem cells).
Figure 4:
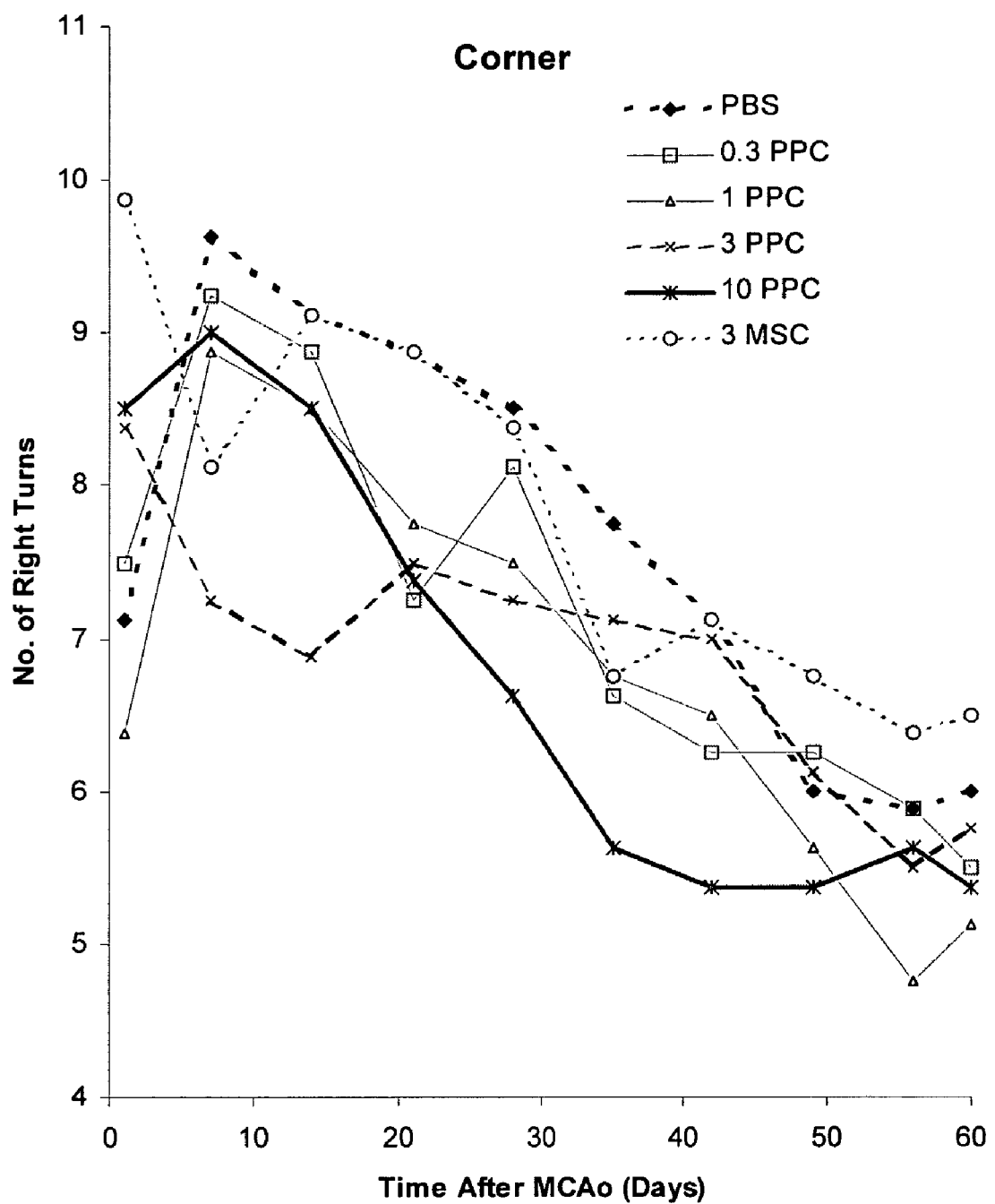
FIG. 4. Graph showing results of Corner Test following middle cerebral artery occlusion (MCAo) in rats (PPC=postpartum-derived cells; MSC=mesenchymal stem cells).

A dose response was observed in mNSS (FIG. 1), foot-fault (FIG. 2), and adhesive removal (FIG. 3) tests, whereby a dose of either 3 million or 10 million PPDC led to faster, greater recovery. In the corner test (FIG. 4), PPDC-treated rats also performed better than PBS vehicle control while MSC-treated rats were worse than PBS control.

Summary

PPDCs demonstrated efficacy in the treatment of stroke in the rodent MCAo model. A dose response was observed, up to the two highest PPDC doses that showed similar functional improvement outcomes. Cell-treated animals continued to improve steadily over the duration of 60 days.

References for Example 21

1. Chen, H., M. Chopp, Z. G. Zhang, and J. H. Garcia. 1992. The effect of hypothermia on transient middle cerebral artery occlusion in the rat. *J Cereb Blood Flow Metab* 12:621-8.
2. Chen, J., Y. Li, L. Wang, Z. Zhang, D. Lu, M. Lu, and M. Chopp. 2001. Therapeutic benefit of intravenous administration of bone marrow stromal cells after cerebral ischemia in rats. *Stroke* 32:1005-11.
3. Guide for the Care and Use of Laboratory Animals, 7th edition.
4. Li, Y., C. Powers, N. Jiang, and M. Chopp. 1998. Intact, injured, necrotic and apoptotic cells after focal cerebral ischemia in the rat. *J Neurol Sci* 156:119-32.
5. Li, Y., V. G. Sharov, N. Jiang, C. Zaloga, H. N. Sabbah, and M. Chopp. 1995. Ultrastructural and light microscopic evidence of apoptosis after middle cerebral artery occlusion in the rat. *Am J Pathol* 146:1045-51.
6. Paxinos, G., and C. Watson. 1986. *The rat brain in stereotaxic coordinates,* 2nd edition. Sydney; Orlando: Academic Press.
7. Schallert, T., D. A. Kozlowski, J. L. Humm, and R. R. Cocke. 1997. Use-dependent structural events in recovery of function. *Adv Neurol* 73:229-38.
8. Swanson, R. A., M. T. Morton, G. Tsao-Wu, R. A. Savalos, C. Davidson, and F. R. Sharp. 1990. A semiautomated method for measuring brain infarct volume [see comments]. *J Cereb Blood Flow Metab* 10:290-3.
9. Ujike, H., M. Takaki, M. Kodama, and S. Kuroda. 2002. Gene expression related to synaptogenesis, neuritogenesis, and MAP kinase in behavioral sensitization to psychostimulants. *Ann N Y Acad Sci* 965:55-67.
10. Zhang, L., T. Schallert, Z. G. Zhang, Q. Jiang, P. Amiego, Q. Li, M. Lu, and M. Chopp. 2002a. A test for detecting long-term sensorimotor dysfunction in the mouse after focal cerebral ischemia. *J Neurosci Methods* 117:207-14.
11. Zhang, Z. G., L. Zhang, W. Tsang, H. Soltanian-Zadeh, D. Morris, R. Zhang, A. Goussev, C. Powers, T. Yeich, and M. Chopp. 2002b. Correlation of VEGF and angiopoietin expression with disruption of blood-brain barrier and angiogenesis after focal cerebral ischemia. *J Cereb Blood Flow Metab* 22:379-92.

The present invention is not limited to the embodiments described and exemplified above, but is capable of variation and modification within the scope of the appended claims.

What is claimed is:

1. A method of treating a patient who has had a stroke, the method comprising administering to the patient cells in an amount effective to treat the stroke, wherein the cells are isolated from mammalian umbilical cord tissue substantially free of blood or are expanded in culture from a cell isolated from mammalian umbilical cord tissue substantially free of blood, wherein the cells are capable of self-renewal and expansion in culture, and wherein the cells do not produce CD117.

2. The method of claim 1, wherein the stroke is ischemic stroke.

3. The method of claim 1, wherein the stroke is hemorrhagic stroke.

4. The method of claim 1, wherein the cells are induced in vitro to differentiate into neural lineage cells prior to administration.

5. The method of claim 1, wherein the cells are administered with at least one other cell type of an astrocyte, oligodendrocyte, neuron, neural progenitor, neural stem cell, genetically engineered cell, or other multipotent or pluripotent stem cell.

6. The method of claim 5, wherein the at least one other cell type is administered simultaneously with, or before, or after, the postpartum-derived cells.

7. The method of claim 1, wherein the cells are administered at a pre-determined site in the central or peripheral nervous system of the patient.

8. The method of claim 1, wherein the cells are administered by injection or infusion.

9. The method of claim 1, wherein the cells are administered encapsulated within an implantable device.

10. The method of claim 1, wherein the cells are administered by implantation of a matrix or scaffold containing the cells.

11. The method of claim 1, wherein the cells exert a trophic effect on the nervous system of the patient.

12. The method of claim 1, wherein the cells have the potential for at least about 40 doublings in culture.

13. The method of claim 1, wherein the cells attach and expand on a coated or uncoated tissue culture vessel, wherein the coated tissue culture vessel comprises a coating of gelatin, laminin, collagen, polyornithine, vitronectin, or fibronectin.

14. The method of claim 1, wherein the cells produce at least one of tissue factor, vimentin, and alpha-smooth muscle actin.

15. The method of claim 1, wherein the cells produce at least one of CD10, CD13, CD44, CD73, CD90, PDGFr-alpha, PD-L2 and HLA-A,B,C.

16. The method of claim 1, wherein the cells do not produce at least one of CD31, CD34, CD45, CD80, CD86, CD141, CD178, B7-H2, HLA-G, and HLA-DR, DP,DQ, as detected by flow cytometry.

17. The method of claim 1, wherein the cells exhibit increased expression, relative to a human cell that is a fibroblast, a mesenchymal stem cell, or an iliac crest bone marrow cell, of at least one endogenous gene encoding interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; downregulated in ovarian cancer 1; and *Homo sapiens* gene from clone DKFZp547k1113.

18. The method of claim 1, wherein the cells exhibit reduced expression, relative to a human cell that is a fibroblast, a mesenchymal stem cell, or an iliac crest bone marrow cell, of at least one endogenous gene encoding short stature homeobox 2; heat shock 27 kDa protein 2; chemokine (C-X-C motif) ligand 12 (stromal cell-derived factor 1); elastin; Homo sapiens; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; Homo sapiens cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA 1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); Homo sapiens mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; Homo sapiens; cDNA DKFZp564B222 (from clone DKFZp564B222); BCL2/adenovirus E1B 19 kDa interacting protein 3-like; AF binding protein 1; cytochrome c oxidase subunit VIIa polypeptide 1 (muscle); similar to neuralin 1; B cell translocation gene 1; hypothetical protein FLJ23191; and DKFZp586L151.

19. The method of claim 1, wherein the cells secrete at least one of MCP-1, IL-6, IL-8, GCP-2, HGF, KGF, FGF, HB-EGF, BDNF, TPO, MIP1a, RANTES, and TIMP1.

20. The method of claim 1, wherein the cells do not secrete at least one of TGF-beta2, ANG2, PDGFbb, MIP1b, I309, MDC, and VEGF, as detected by ELISA.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 1
gagaaatcca aagagcaaat gg                                                  22

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
agaatggaaa actggaatag g                                                   21

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
tcttcgatgc ttcggattcc                                                     20

<210> SEQ ID NO 4
<211> LENGTH: 21
<212> TYPE: DNA
<213> ORGANISM: Artificial Sequence
```

-continued

```
<220> FEATURE:
<223> OTHER INFORMATION: Oligonucleotide primer

<400> SEQUENCE: 4
gaattctcgg aatctctgtt g                                                 21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
ttacaagcag tgcagaaaac c                                                 21

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 6
agtaaacatt gaaaccacag cc                                                22

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
tctgcagctc tgtgtgaagg                                                   20

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 8
cttcaaaaac ttctccacaa cc                                                22

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 9
cccacgccac gctctcc                                                      17

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 10
tcctgtcagt tggtgctcc                                                    19
```